US008208504B2

(12) United States Patent  
Dantus et al.

(10) Patent No.: US 8,208,504 B2
(45) Date of Patent: Jun. 26, 2012

(54) LASER PULSE SHAPING SYSTEM

(75) Inventors: Marcos Dantus, Okemos, MI (US); Vadim V. Lozovoy, Holt, MI (US)

(73) Assignee: Board of Trustees Operation Michigan State University, East Lansing, MI (US)

( * ) Notice: Subject to any disclaimer, the term of this patent is extended or adjusted under 35 U.S.C. 154(b) by 700 days.

(21) Appl. No.: 12/264,519

(22) Filed: Nov. 4, 2008

(65) Prior Publication Data

US 2009/0122819 A1     May 14, 2009

Related U.S. Application Data

(60) Division of application No. 10/265,211, filed on Oct. 4, 2002, now Pat. No. 7,450,618, which is a continuation-in-part of application No. PCT/US02/02548, filed on Jan. 28, 2002.

(60) Provisional application No. 60/265,133, filed on Jan. 30, 2001.

(51) Int. Cl.
*H01S 3/10* (2006.01)

(52) U.S. Cl. .............. 372/22; 372/9; 372/25; 250/281; 250/282; 250/288; 359/237; 359/244; 359/245; 359/246; 359/247

(58) Field of Classification Search .............. 372/9, 22, 372/25; 250/281, 282, 288, 423; 359/237, 359/244–247, 267
See application file for complete search history.

(56) References Cited

U.S. PATENT DOCUMENTS

| 3,214,563 A | 10/1965 | Ford |
| 3,611,182 A | 10/1971 | Treacy |
| 3,919,881 A | 11/1975 | Metherell |
| 3,988,704 A | 10/1976 | Rice et al. |
| 4,167,662 A | 9/1979 | Steen |
| 4,288,691 A | 9/1981 | Horton |
| 4,394,780 A | 7/1983 | Mooradian |
| 4,477,905 A | 10/1984 | Sweeney |
| 4,512,660 A | 4/1985 | Goldberg |
| 4,621,006 A | 11/1986 | Terry et al. |
| 4,655,547 A | 4/1987 | Heritage et al. |

(Continued)

FOREIGN PATENT DOCUMENTS

EP 0605110 A2 7/1994

(Continued)

OTHER PUBLICATIONS

Fowles, "Introduction to Modern Optics," 1989, Dover 2e, pp. 2-19.

(Continued)

*Primary Examiner* — Tod T Van Roy
*Assistant Examiner* — Delma R Forde
(74) *Attorney, Agent, or Firm* — Harness, Dickey & Pierce, P.L.C.

(57) ABSTRACT

A laser system using ultrashort laser pulses is provided. In another aspect of the present invention, the system includes a laser, pulse shaper and detection device. A further aspect of the present invention employs a femtosecond laser and a spectrometer. Still another aspect of the present invention uses a laser beam pulse, a pulse shaper and a SHG crystal. In yet another aspect of the present invention, a multiphoton intrapulse interference phase scan system and method characterize the spectral phase of femtosecond laser pulses. Fiber optic communication systems, photodynamic therapy and pulse characterization tests use the laser system with additional aspects of the present invention.

35 Claims, 19 Drawing Sheets

U.S. PATENT DOCUMENTS

| | | | |
|---|---|---|---|
| 4,746,193 A | 5/1988 | Heritage et al. | |
| 4,772,854 A | 9/1988 | Silberberg | |
| 4,812,776 A | 3/1989 | Sasaki | |
| 4,819,239 A | 4/1989 | Sharp et al. | |
| 4,834,474 A | 5/1989 | George et al. | |
| 4,853,065 A | 8/1989 | Terry et al. | |
| 4,856,860 A | 8/1989 | Silberberg et al. | |
| 4,866,699 A | 9/1989 | Brackett et al. | |
| 4,913,934 A | 4/1990 | Sharp et al. | |
| 4,928,316 A * | 5/1990 | Heritage et al. | 398/199 |
| 4,999,840 A | 3/1991 | Negus | |
| 5,021,282 A | 6/1991 | Terry et al. | |
| 5,034,613 A | 7/1991 | Denk | |
| 5,048,029 A | 9/1991 | Skupsky et al. | |
| 5,054,027 A | 10/1991 | Goodberlet et al. | |
| 5,077,619 A | 12/1991 | Toms | |
| 5,095,487 A | 3/1992 | Meyerhofer et al. | |
| 5,130,994 A | 7/1992 | Madey et al. | |
| 5,132,512 A | 7/1992 | Sanders et al. | |
| 5,132,824 A | 7/1992 | Patel et al. | |
| 5,154,963 A | 10/1992 | Terry | |
| 5,166,818 A | 11/1992 | Chase et al. | |
| 5,239,607 A | 8/1993 | da Silva et al. | |
| 5,341,236 A | 8/1994 | Stappaerts | |
| 5,359,410 A | 10/1994 | Diels et al. | |
| 5,406,408 A | 4/1995 | Ellingson et al. | |
| 5,414,540 A | 5/1995 | Patel et al. | |
| 5,414,541 A | 5/1995 | Patel et al. | |
| 5,463,200 A | 10/1995 | James et al. | |
| 5,526,155 A | 6/1996 | Knox et al. | |
| 5,526,171 A * | 6/1996 | Warren | 359/285 |
| 5,530,544 A | 6/1996 | Trebino et al. | |
| 5,541,947 A | 7/1996 | Mourou et al. | |
| 5,585,913 A | 12/1996 | Hariharan et al. | |
| 5,589,955 A | 12/1996 | Amako et al. | |
| 5,615,673 A | 4/1997 | Berger et al. | |
| 5,631,758 A | 5/1997 | Knox et al. | |
| 5,636,050 A * | 6/1997 | Alfano et al. | 359/238 |
| 5,637,966 A | 6/1997 | Umstadter et al. | |
| 5,682,262 A * | 10/1997 | Wefers et al. | 359/305 |
| 5,684,595 A | 11/1997 | Kato et al. | |
| 5,689,361 A * | 11/1997 | Damen et al. | 359/284 |
| 5,704,700 A | 1/1998 | Kappel et al. | |
| 5,719,650 A | 2/1998 | Wefers et al. | |
| 5,734,503 A | 3/1998 | Szipocs et al. | |
| 5,754,292 A | 5/1998 | Kane et al. | |
| 5,759,767 A | 6/1998 | Lakowicz | |
| 5,774,213 A | 6/1998 | Trebino et al. | |
| 5,793,091 A | 8/1998 | Devoe | |
| 5,798,867 A | 8/1998 | Uchida et al. | |
| 5,822,097 A | 10/1998 | Tournois | |
| 5,828,459 A | 10/1998 | Silberberg | |
| 5,832,013 A | 11/1998 | Yessik et al. | |
| 5,883,309 A | 3/1999 | Vossiek et al. | |
| 5,936,732 A | 8/1999 | Smirl et al. | |
| 5,956,173 A | 9/1999 | Svelto et al. | |
| 5,956,354 A * | 9/1999 | Yan | 372/18 |
| 5,994,687 A | 11/1999 | Chanteloup et al. | |
| 6,002,480 A | 12/1999 | Izatt et al. | |
| 6,008,899 A | 12/1999 | Trebino et al. | |
| 6,042,603 A | 3/2000 | Fisher et al. | |
| 6,057,919 A | 5/2000 | Machida et al. | |
| 6,058,132 A | 5/2000 | Iso et al. | |
| 6,072,813 A | 6/2000 | Tournois | |
| 6,080,148 A | 6/2000 | Damasco et al. | |
| 6,081,543 A | 6/2000 | Liu et al. | |
| 6,111,251 A | 8/2000 | Hillenkamp | |
| 6,122,419 A | 9/2000 | Kurokawa et al. | |
| 6,130,426 A | 10/2000 | Laukien et al. | |
| 6,156,527 A | 12/2000 | Schmidt et al. | |
| 6,166,385 A | 12/2000 | Webb et al. | |
| 6,178,041 B1 | 1/2001 | Simon | |
| 6,184,490 B1 | 2/2001 | Schweizer | |
| 6,191,386 B1 | 2/2001 | Albright et al. | |
| 6,219,142 B1 | 4/2001 | Kane | |
| 6,259,104 B1 | 7/2001 | Baer | |
| 6,272,156 B1 | 8/2001 | Reed et al. | |
| 6,284,437 B1 * | 9/2001 | Kashyap | 430/321 |
| 6,288,782 B1 | 9/2001 | Worster | |
| 6,296,810 B1 | 10/2001 | Ulmer | |
| 6,316,153 B1 | 11/2001 | Goodman | |
| 6,327,068 B1 * | 12/2001 | Silberberg et al. | 359/239 |
| 6,337,606 B1 | 1/2002 | Brombaugh et al. | |
| 6,344,653 B1 | 2/2002 | Webb et al. | |
| 6,391,229 B1 | 5/2002 | Watanabe et al. | |
| 6,396,856 B1 | 5/2002 | Sucha et al. | |
| 6,402,898 B1 | 6/2002 | Brumer et al. | |
| 6,421,154 B1 * | 7/2002 | Diels et al. | 398/182 |
| 6,479,822 B1 | 11/2002 | Nelson et al. | |
| 6,480,656 B1 | 11/2002 | Islam et al. | |
| 6,498,801 B1 | 12/2002 | Dudelzak et al. | |
| 6,504,612 B2 | 1/2003 | Trebino | |
| 6,515,257 B1 | 2/2003 | Jain et al. | |
| 6,566,667 B1 | 5/2003 | Partlo et al. | |
| 6,573,493 B1 | 6/2003 | Futami et al. | |
| 6,577,782 B1 | 6/2003 | Leaird et al. | |
| 6,610,351 B2 | 8/2003 | Shchegolikhin et al. | |
| 6,610,977 B2 | 8/2003 | Megerle | |
| 6,621,613 B2 | 9/2003 | Silberberg et al. | |
| 6,625,181 B1 | 9/2003 | Oshemkov et al. | |
| 6,678,450 B1 | 1/2004 | Franson | |
| 6,697,196 B2 * | 2/2004 | Suzuki | 359/385 |
| 6,723,991 B1 | 4/2004 | Sucha et al. | |
| 6,753,957 B1 | 6/2004 | Graft et al. | |
| 6,757,463 B2 | 6/2004 | Hutchinson et al. | |
| 6,795,456 B2 | 9/2004 | Scaggs | |
| 6,795,777 B1 | 9/2004 | Scully et al. | |
| 6,801,318 B2 | 10/2004 | Fu et al. | |
| 6,801,551 B1 | 10/2004 | Delfyett et al. | |
| 6,804,000 B2 | 10/2004 | Roorda et al. | |
| 6,857,744 B2 | 2/2005 | Nakada et al. | |
| 6,879,426 B1 | 4/2005 | Weiner | |
| 6,885,325 B2 | 4/2005 | Omelyanchouk et al. | |
| 6,914,668 B2 | 7/2005 | Brestel et al. | |
| 6,915,040 B2 | 7/2005 | Willner et al. | |
| 6,930,779 B2 | 8/2005 | McGrew | |
| 6,963,591 B2 | 11/2005 | Tulloch et al. | |
| 7,033,519 B2 | 4/2006 | Taylor et al. | |
| 7,049,543 B2 | 5/2006 | Roos et al. | |
| 7,057,788 B2 | 6/2006 | Ohbayashi et al. | |
| 7,088,435 B2 | 8/2006 | Brestel et al. | |
| 7,096,125 B2 | 8/2006 | Padmanabhan et al. | |
| 7,105,811 B2 | 9/2006 | Dantus et al. | |
| 7,132,223 B2 | 11/2006 | Schroeder et al. | |
| 7,169,709 B2 | 1/2007 | Koide | |
| 7,170,030 B2 | 1/2007 | Haight et al. | |
| 7,170,598 B2 | 1/2007 | Walla et al. | |
| 7,256,885 B2 | 8/2007 | Silberberg et al. | |
| 7,276,103 B2 | 10/2007 | Wöste et al. | |
| 7,289,203 B2 | 10/2007 | Frankel | |
| 7,342,223 B2 | 3/2008 | Ohkubo et al. | |
| 7,348,569 B2 * | 3/2008 | Feurer et al. | 250/400 |
| 7,369,773 B2 * | 5/2008 | Weiner | 398/81 |
| 7,403,281 B2 | 7/2008 | Carron et al. | |
| 7,403,282 B2 | 7/2008 | Silberberg et al. | |
| 7,411,166 B2 | 8/2008 | Wolleschensky et al. | |
| 7,439,497 B2 | 10/2008 | Dantus et al. | |
| 7,450,618 B2 | 11/2008 | Dantus | |
| 7,567,596 B2 | 7/2009 | Dantus et al. | |
| 7,576,907 B1 * | 8/2009 | Bartels et al. | 359/298 |
| 7,583,710 B2 | 9/2009 | Dantus et al. | |
| 7,609,731 B2 | 10/2009 | Dantus et al. | |
| 7,826,051 B2 | 11/2010 | Silberberg et al. | |
| 7,973,936 B2 | 7/2011 | Dantus | |
| 7,989,731 B2 | 8/2011 | Bischoff et al. | |
| 2001/0015411 A1 | 8/2001 | Ohdaira et al. | |
| 2001/0015990 A1 | 8/2001 | Miyai | |
| 2001/0017727 A1 | 8/2001 | Sucha et al. | |
| 2002/0025490 A1 | 2/2002 | Shchegolikhin et al. | |
| 2002/0086245 A1 | 7/2002 | Zait et al. | |
| 2002/0097761 A1 | 7/2002 | Sucha et al. | |
| 2003/0063884 A1 | 4/2003 | Smith et al. | |
| 2003/0099264 A1 | 5/2003 | Dantus et al. | |
| 2003/0123051 A1 | 7/2003 | McGrew | |
| 2003/0194165 A1 | 10/2003 | Silberberg et al. | |
| 2003/0210400 A1 | 11/2003 | Joffre et al. | |
| 2004/0012837 A1 | 1/2004 | Kaplan et al. | |

| | | | |
|---|---|---|---|
| 2004/0021243 | A1 | 2/2004 | Shih et al. |
| 2004/0031906 | A1 | 2/2004 | Glecker |
| 2004/0058058 | A1 | 3/2004 | Shchegolikhin et al. |
| 2004/0089804 | A1 | 5/2004 | Dantus et al. |
| 2004/0128081 | A1 | 7/2004 | Rabitz et al. |
| 2004/0145735 | A1 | 7/2004 | Silberberg et al. |
| 2004/0155184 | A1 | 8/2004 | Stockman et al. |
| 2004/0233944 | A1 | 11/2004 | Dantus et al. |
| 2004/0240037 | A1 | 12/2004 | Harter |
| 2004/0263950 | A1 | 12/2004 | Fermann et al. |
| 2005/0017160 | A1 | 1/2005 | Wolleschensky et al. |
| 2005/0021243 | A1 | 1/2005 | Dantus et al. |
| 2005/0036202 | A1 | 2/2005 | Cohen et al. |
| 2005/0103759 | A1 | 5/2005 | Li et al. |
| 2005/0155958 | A1 | 7/2005 | Arai et al. |
| 2005/0161669 | A1 | 7/2005 | Jovanovich et al. |
| 2005/0185188 | A1 | 8/2005 | McGrew |
| 2005/0226287 | A1 | 10/2005 | Shah et al. |
| 2005/0230365 | A1 | 10/2005 | Lei et al. |
| 2005/0232313 | A1 | 10/2005 | Fermann et al. |
| 2005/0248758 | A1 | 11/2005 | Carron et al. |
| 2006/0000988 | A1 | 1/2006 | Stuart et al. |
| 2006/0006964 | A1 | 1/2006 | Huang et al. |
| 2006/0019171 | A1 | 1/2006 | Hosono et al. |
| 2006/0028655 | A1 | 2/2006 | Cordingley et al. |
| 2006/0032841 | A1 | 2/2006 | Tan et al. |
| 2006/0039419 | A1 | 2/2006 | Deshi |
| 2006/0051025 | A1 | 3/2006 | Mizuuchi et al. |
| 2006/0056468 | A1 | 3/2006 | Dantus et al. |
| 2006/0058683 | A1 | 3/2006 | Chance |
| 2006/0066848 | A1 | 3/2006 | Frankel |
| 2006/0071803 | A1 | 4/2006 | Hamburger et al. |
| 2006/0096426 | A1 | 5/2006 | Park |
| 2006/0096962 | A1 | 5/2006 | Park |
| 2006/0119743 | A1 | 6/2006 | Lin |
| 2006/0120412 | A1 | 6/2006 | Liu |
| 2006/0134004 | A1 | 6/2006 | Gellermann et al. |
| 2006/0169677 | A1 | 8/2006 | Deshi |
| 2006/0187974 | A1 | 8/2006 | Dantus |
| 2006/0207975 | A1 | 9/2006 | Ehrmann et al. |
| 2006/0207976 | A1 | 9/2006 | Bovatsek et al. |
| 2006/0243712 | A1 | 11/2006 | Haight et al. |
| 2006/0274403 | A1 | 12/2006 | Kaplan et al. |
| 2006/0285071 | A1 | 12/2006 | Erickson et al. |
| 2007/0034615 | A1 | 2/2007 | Kleine |
| 2007/0093970 | A1 | 4/2007 | Padmanabhan et al. |
| 2007/0103778 | A1 | 5/2007 | Kaplan et al. |
| 2008/0170218 | A1 | 7/2008 | Dantus et al. |
| 2008/0309931 | A1 | 12/2008 | Silberberg et al. |
| 2009/0188901 | A1 | 7/2009 | Dantus |
| 2009/0207869 | A1 | 8/2009 | Dantus et al. |
| 2009/0296744 | A1 | 12/2009 | Dantus et al. |
| 2011/0005090 | A1* | 1/2011 | Lee et al. ............... 33/1 PT |

FOREIGN PATENT DOCUMENTS

| | | |
|---|---|---|
| EP | 1742311 A1 | 1/2007 |
| JP | 11095051 A | 4/1999 |
| JP | 2000055781 A | 2/2000 |
| JP | 2001337301 A | 12/2001 |
| JP | 2002139716 A | 5/2002 |
| JP | 2003 155256 A | 5/2003 |
| WO | WO 99/57318 | 11/1999 |
| WO | WO 00/70647 | 11/2000 |
| WO | WO 01/54323 | 7/2001 |
| WO | WO-0231799 A1 | 4/2002 |
| WO | WO 02/061799 | 8/2002 |
| WO | WO-2004023413 A2 | 3/2004 |
| WO | WO 2005/088783 | 9/2005 |
| WO | WO-2005111677 A2 | 11/2005 |
| WO | WO-2006079083 A2 | 7/2006 |
| WO | WO-2006138442 A2 | 12/2006 |
| WO | WO-2007001308 A2 | 1/2007 |
| WO | WO-2007145702 A2 | 12/2007 |
| WO | WO-2009086122 A2 | 7/2009 |

OTHER PUBLICATIONS

Ogawa et al, Dependence of the Laser Two-Photon Ionization Process in Solution on the Laser Pulse Width, Analytical Chemistry, vol. 73, Mar. 20, 2001, pp. 2066-2069.

Zeek, Erik; "Pulse Shaping for High-Harmonic Generation;" Dissertation Submitted in Partial Fulfillment of the Requirements for the Degree of Doctor of Philosophy (Applied Physics) in the University of Michigan, 2000; 126 pages.

Baltuška, Andrius et al.; "Visible Pulse Compression to 4 fs by Optical Parametric Amplification and Programmable Dispersion Control;" Optics Letters, vol. 27, No. 5, Mar. 1, 2002, pp. 306-308.

"BNS Liquid Crystal Solutions Spatial Light Modulators 1 × 12,288 Linear Series," brochure, Apr. 2006, Boulder Nonlinear Systems, Inc., pp. 1-4.

"Shape Your Pulses. Control Your Experiment." advertisement, Laser Focus World, (Dec. 1997) p. 26, CRI, Inc.

Akozbek, N. et al.; "Continuum Generation of the Third-Harmonic Pulse Generated by an Intense Femtosecond IR Laser Pulse in Air;" Applied Physics B (Lasers and Optics), Springer-Verlag, Germany, vol. B77, No. 2-3, XP002476096; Sep. 2003, pp. 177-183.

Alexeev, I. et al., "Ultraviolet Light Generation by Intense Laser Filaments Propagating in Air," Conference on Lasers & Electro-Optics (CLEO), Baltimore, Maryland, USA, XP010876479; May 22-27, 2005, pp. 189-191.

Aviv Circular Dichroism Spectrometer, Model 400, Aviv Biomedical, Inc., http://www.avivbiomedical.com, Nov. 29, 2006; 2 pages.

Barry, Liam P., et al., "A High-Speed Optical Star Network Using TDMA and All-Optical Demultiplexing Techniques", IEEE Journal on Selected Areas in Communications, vol. 14, No. 5, (Jun. 1996), pp. 1030-1038.

Bender, Daniel A., et al., "Modified spectrum autointerferometric correlation (MOSAIC) for single-shot pulse characterization," Optics Letters, vol. 32, No. 19 (Oct. 1, 2007) Optical Society of America, pp. 2822-2824.

Brixner, T., et al., "Adaptive Shaping of Femtosecond Polarization Profiles," J. Opt. Soc. Am. B. vol. 20, No. 5, May 2003; pp. 878-881.

Brixner, T., et al., "Femtosecond Polarlization Pulse Shaping," Optics Letters, vol. 26, No. 8, Apr. 15, 2001; pp. 557-559.

Brown, E. J. et al.; "Femtosecond Transient-Grating Techniques: Population and Coherence Dynamics Involving Ground and Excited States;" J. Chem. Phys., vol. 110, No. 12, Mar. 22, 1999; pp. 5772-5788.

Brown, E. J. et al.; "Population and Coherence Control by Three-Pulse Four-Wave Mixing;" J. Chem. Phys., vol. 111, No. 9, Sep. 1, 1999; pp. 3779-3782.

Brown, E. J. et. al. "Ultrafast Rotational Anisotropy Measurements: Unidirectional Detection;" J. Phys. Chem. A, vol. 103, No. 16, 1999 pp. 2912-2916.

Brown, E. J. et. al. "Ultrafast Rotational Anisotropy Measurements; Strong-Field Nonlinear Saturation Effects;" J. Phys. Chem. A, vol. 105, No. 34, 2001; pp. 8004-8010.

Butcher, Steve, et al., "Multiphoton approach shapes ultrafast pulses," Pulse Shaping, (2006) Institute of Physics and IOP Publishing Ltd., 3 pages.

Choi, K-S et al.; "Charge Density Wave Caused by Reducing $ThSe_3$ by One Electron. Superstructure and Short-Range Order in $ATh_2Se_6$ (A = K, Rb) Studied by X-Ray Diffraction, Electron Diffraction, and Diffuse Scattering;" J. Am. Chem. Soc., vol. 120, No. 41, 1998; pp. 10706-10714.

Comstock, M. et al.; "Femtosecond Photon Echo Measurements of Electronic Coherence Relaxation Between the $X(^1Eg+)$ and $B(^3II_{0u}+)$ states of $I_2$ in the Presence of He, Ar, $N_2$, $O_2$, $C_3H_8$;" J. Chem. Phys., vol. 119, No. 13, Oct. 1, 2003; pp. 6546-6553.

Comstock, M. et al.; "Rotational Wavepacket Revivals for Phase Modulation of Ultrafast Pulses;" Chemical Physics Letters, 372, 2003; pp. 739-744.

Comstock, M. et al.; "Ultrafast Laser Induced Molecular Alignment and Deformation: Experimental Evidence From Neutral Molecules and From Fragment Ions;" J. Phys. Chem. A, vol. 107, No. 40, 2003; pp. 8271-8281.

Comstock, M. et al.; "Ultrafast Transient-Grating Study of Molecules After High Intensity Excitation;" in Ultrafast Phenomena XII, 2000; 2 pages.

Dan Oron et al.; "Single-Pulse Phase-Contrast Nonlinear Raman Spectroscopy"; Physical Review Letters, vol. 89, No. 27; Dec. 30, 2002; pp. 27300-1-273001-4.

Dantus, Marcos et al., "Stereoisomer Recognition by MS with Shaped Laser Pulses," American Chemical Society. Abstracts of paper. At the national meeting, American Chemical Society, Washington, D.C., U.S. vol. 231 (Mar. 26, 2006) pp. 1-ANYL, XP009082814, ISSN: 0065-7727, the whole document.

Dantus, Marcos et al.; "Femtosecond Laser Observations of Molecular Vibration and Rotation;" Nature, vol. 343, Feb. 22, 1990; pp. 737-739.

Dantus, Marcos et al.; "Femtosecond Real-Time Probing of Reactions. II. The Dissociation Reaction of ICN;" J. Chem. Phys., vol. 89, No. 10, Nov. 15, 1988; pp. 6128-6140.

Dantus, Marcos et al.; "Femtosecond Real-Time Probing of Reactions. V. The reaction of IHgI;" J. Chem. Phys., vol. 91, No. 12, Dec. 15, 1989; pp. 7437-7450.

Dantus, Marcos et al.; "Real-Time Femtosecond Probing of "Transition States" in Chemical Reactions;" J. Chem. Phys., vol. 87, No. 4, Aug. 15, 1987; pp. 2395-2397.

Dantus, Marcos et al.; "Ultrafast Spectroscopy;" Encyclopedia of Applied Physics, vol. 22, 1998; pp. 431-456.

Dantus, Marcos, et al., "MIIPS characterizes and corrects femtosecond pulses," Ultrafast Optical Systems, Laser Focus World, (May 2007) XP001539450, 4 pages.

Dantus, Marcos. "Laser Control of Chemical Reactions." Chemical & Engineering News, vol. 79, 2001; p. 191.

Dantus, Marcos; "Ahmed Zewail, Nobel Laureate in Chemistry;" European Photochemistry Association (EPA) Newsletter, No. 69, Jul. 2000; 5 pages.

Dantus, Marcos; "Femtosecond Laser Pulses: Principles and Experiments;" (Book Review) J. Am. Chem. Soc., vol. 121, No. 37, 1999; pp. 8677-8678.

Dela Cruz, J. M. et al.; "Coherent Control Improves Biomedical Imaging With Ultrashort Shaped Pulses;" Journal of Photochemistry and Photobiology A: Chemistry 180, Mar. 2006; pp. 307-313.

Dela Cruz, Johanna M., et al., "Multidimensional analysis with shaped femtosecond pulses: identification of conformational and geometric isomers and mixtures using mass spectrometry," American Chemical Society. Abstracts of paper. At the national meeting, American Chemical Society, Washington, D.C., U.S., vol. 230, (Aug. 28, 2005) p. U418, XP009082815, ISSN: 0065-7727, the whole document.

Dela Cruz, Johanna M., et al., "Quantitative mass spectrometric identification of isomers applying coherent laser control," Journal of Physical Chemistry A ACS USA, vol. 109, No. 38 (Sep. 29, 2005) pp. 8447-8450, XP002431289, ISSN: 1089-5639, figure 1.

Delfyett, Peter J., et al., "High-Power Ultrafast Laser Diodes", IEEE Journal of Quantum Electronics, vol. 28, No. 10, (Oct. 1992), pp. 2203-2219.

Delong, K.W., et al., "Frequency Resolved Optical Gating with the Use of 2nd-Harmonic Generation." Journal of Optical Society of America B-Optical Physics, 1994. 11 (11): pp. 2206-2215.

Dreischuh, A., Experimental Demonstraction of Pulse Shaping and Shortening by Spatial Filtering of an Induced-Phase-Modulated Probe Wave, IEEE Journal of Quantum Electronics, vol. 33, No. 3, (Mar. 1997), pp. 329-335.

Dugan, M.A., et al., "High-resolution acousto-optic shaping of unamplified and amplified femtosecond laser pulses", J. Opt. Soc. Am. B, vol. 14, No. 9, (Sep. 1997), pp. 2348-2358, Optical Society of America.

Efimov, A., et al., "Programmable shaping of ultrabroad-bandwidth pulses from a Ti:sapphire laser", Journal B/vol. 12, No. 10 (Oct. 1995) pp. 1968-1980, Optical Society of America.

Fermann, M.E., et al., "Additive-pulse-compression mode locking of a neodymium fiber laser", Optics Letters, vol. 16, No. 4, (Feb. 15, 1991), Optical Society of America.

Fetterman, et al., "Ultrafast pulse shaping: amplification and characterization", Optics Express, vol. 3, No. 10, (Nov. 9, 1998), pp. 366-375.

Fork, R.L., et al., "Compression of optical pulses to six femtoseconds by using cubic phase compensation", Optics Letters, (Jul. 1987), vol. 12, No. 7, Optical Society of America.

Fujimoto, Masatoshi, et al., "Programmable shaping of a subterawatt, femtosecond laser pulse by modulating the spectral phase of the preamplified pulse," Optics Communications, 280 (2007) ScienceDirect, pp. 404-407.

Galler, A., et al., "Pulse shaper assisted short laser pulse characterization," Applied Physics B90, Lasers and Optics (Jan. 2008) pp. 427-430.

Gallmann, L., et al., "Characterization of sub-6-fs optical pulses with spectral phase interferometry for direct electric-field reconstruction," Optics Letters, vol. 24, No. 18 (Sep. 15, 1999) p. 13140-1316.

Gomes, A.S.L., et al., "Optical fibre-grating pulse compressors", Tutorial Review, Optical and Quantum Electronics 20, (1988), pp. 95-112.

Grimberg, B. I. et al.; "Ultrafast Nonlinear Spectroscopic Techniques in the Gas Phase and Their Density Matrix Representation;" J. Phys. Chem. A, vol. 106, No. 5, Feb. 7, 2002; pp. 697-718.

Gross, P. et al.; "Femtosecond Photoassociation: Coherence and Implications for Control in Bimolecular Reactions;" J. Chem. Phys., vol. 106, No. 19, May 15, 1997; pp. 8013-8021.

Gunaratne, T. et al.; "Influence of Bandwidth and Phase Shaping on Laser Induced Breakdown Spectroscopy With Ultrashort Laser Pulses;" Chemical Physics Letters 423, Apr. 3, 2006; pp. 197-201.

Gunn, J M et al: "Polarization and phase control of remote surface-plasmon-mediated two-photo-induced emission and waveguiding" Nano Letters American Chem. SOC. USA, vol. 6, No. 12, Aug. 2006.

Haner, M., et al., "Generation of programmable, picosecond-resolution shaped laser pulses by fiber-grating pulse compression", Optics Letters, vol. 12, No. 6, (Jun. 1987), pp. 398-400, Optical Society of America.

Hanna, Sherif F. et al.; "Electronic-resonance-enhanced coherent anti-Stokes Raman spectroscopy of nitric oxide"; Applied Physics Letters; vol. 83, No. 9, Sep. 1, 2003; pp. 1887-1889.

Heritage, J.P., "Picosecond pulse shaping by spectral phase and amplitude manipulation", Optics Letters, vol. 10, No. 12, (Dec. 1985), pp. 609-611, Optical Society of America.

Jasco Comparison Proven Spectroscopy & Chromatography Technology, J-815 Circular Dichroism Spectropolarimeter, Jasco UK, http://www.jasco.co.uk/j800.asp, Nov. 29, 2006; 2 pages.

Jiang, et al. "Spectral line-by-line pulse shaping," Optics Letters, vol. 30, No. 12 (Jun. 15, 2005) Optical Society of America, pp. 1557-1559.

Jiang, et al., "Line-by-line pulse shaping control of optical arbitrary waveform generation," Optics Express, vol. 13, No. 25, (Dec. 12, 2005) Optical Society of America, pp. 10431-10439.

Kapteyn, Henry C. et al.; "A Comparison of Multipass Vs. Regenerative Ti:Sapphire Laser Amplifiers;" Kapteyn-Murnane Laboratories Inc., Boulder, CO, USA, www.kmlabs.com; (2003) 2 pages.

Kolenda, Jürgen, et al., "Pulse Shaping with the MIIPS-Process," Laser Technology, (Jan. 2008) Photonik International, p. 68.

Konorov, S.O., "Laser Breakdown with Millijoule Trains of Picosecond Pulses Transmitted through a Hollow-Core Photonic-Crystal Fiber", Laser Physics, vol. 13, No. 4, (2003) pp. 652-656.

Kosik, Ellen M., et al., "The effects of noise on ultrashort optical pulse measurement using SPIDER"; The Institute of Optics, University of Rochester, Rochester, NY; (2000) pp. 21-23.

Krausz, F., et al., "Generation of 33-fs optical pulses from a solid-state laser", Optics Letters, (Feb. 1, 1992), vol. 17, No. 3, Optical Society of America.

Lemoff, B.E., et al., "Quintic-phase-limited, spatially uniform expansion and recompression of ultrashort optical pulses", Optics Letters, vol. 18, No. 19, (Oct. 1, 1993), pp. 1651-1653, Optical Society of America.

Lim, Sang-Hyun et al.; "Single-Pulse Phase-Control Interferometric Coherent Anti-Stokes Raman Scattering Spectroscopy;" Physical Review A, 72, (Oct. 2005); pp. 041803-1-041803-4.

Link, Stephan et al.; "Optical Properties and Ultrafast Dynamics of Metallic Nanocrystals;" Annu. Rev. Phys. Chem. 54, 2003; pp. 331-369.

Liu, Yongqian, et al., "Terahertz Waveform Synthesis via Optical Pulse Shaping", IEEE Journal of Selected Topics in Quantum Electronics, (Sep. 1996), vol. 2, No. 3, pp. 709-719.

Lozovoy, V. V. et al.: "Multiphoton Intrapulse Interference. IV. Ultrashort Laser Pulse Spectral Phase Characterization and Compensation;" Optics Letters, vol. 29, No. 7, Apr. 1, 2004; pp. 775-777.

Lozovoy, V. V. et al.; "Cascaded Free-Induction Decay Four-Wave Mixing;" Chemical Physics 266, 2001, pp. 205-212.

Lozovoy, V. V. et al.; "Femtosecond Spectrally Dispersed Three-Pulse Four-Wave Mixing: The Role of Sequence and Chirp in Controlling Intramolecular Dynamics;" J. Raman Spectroscopy 31, 2000; pp. 41-49.

Lozovoy, V. V. et al.; "Photon Echo Pulse Sequences With Femtosecond Shaped Laser Pulses as a Vehicle for Molecule-Based Quantum Computation;" J. Chemical Physics Letters 351, Jan. 10, 2002; pp. 213-221.

Lozovoy, V. V. et al.; "Spectral Phase Optimization of Femtosecond Laser Pulses for Narrow-Band, Low-Background Nonlinear Spectroscopy;" Optics Express, vol. 13, No. 26, Dec. 26, 2005; pp. 10882-10887.

Lozovoy, V. V. et al.; "Systematic Control of Nonlinear Optical Processes Using Optimally Shaped Femtosecond Pulses;" ChemPhysChem, Wiley-VCH Verlag GmbH & Co. KGaA, Weinheim, 6, 2005; pp. 1970-2000.

Lozovoy, V. V. et al.; "The Role of Microscopic and Macroscopic Coherence in Laser Control;" Chemical Physics 267, 2001; pp. 99-114.

Lozovoy, V. V. et al.; "The Role of Pulse Sequences in Controlling Ultrafast Intramolecular Dynamics With Four-Wave Mixing;" Int. Rev. in Physical Chemistry, vol. 19, No. 4, 2000; pp. 531-552.

Lozovoy, V. V., et al., "Laser Control of Physicochemical Processes; Experiments and Applications," The Royal Society of Chemistry 2006, Annu. Rep. Prog. Chem, Sect. C, 102. www.rsc.org/annrepc (2006) pp. 227-258.

Lozovoy, V.V. et al; "What Role Can Four-Wave Mixing Techniques Play in Coherent Control?;" Advances in Multiphoton Processes and Spectroscopy 14; and Quantum Control of Molecular Reaction Dynamics, edited by R.J. Gordon and Y. Fujimura, World Scientific, Singapore, 2000; pp. 62-79.

Marvet, Una et al.; "Femtosecond Concerted Elimination of Halogen Molecules From Halogenated Alkanes;" Phys. Chem. Chem. Phys., 2, 2000; pp. 885-891.

Marvet, Una et al.; "Femtosecond Dynamics of Photoinduced Molecular Detachment From Halogenated Alkanes. I. Transition State Dynamics and Product Channel Coherence;" J. Chem. Phys., vol. 109, No. 11, Sep. 15, 1998.

Marvet, Una et al.; "Femtosecond Dynamics of Unimolecular and Unrestricted Bimolecular Reactions;" J. Phys. Chem. A, vol. 102, No. 23, 1998; pp. 4111-4117.

Marvet, Una et al.; "Femtosecond Observation of a Concerted Chemical Reaction;" Chemical Physics Letters, 256, Jun. 21, 1996; pp. 57-62.

Marvet, Una et al.; "Femtosecond Photoassociation Spectroscopy: Coherent Bond Formation;" Chemical Physics Letters, 245, Nov. 3, 1995; pp. 393-399.

Meshulach, D., et al., "Adaptive Compression of Femtosecond Pulses", presented at the Ultrafast Optics 1997 Conference, Aug. 1997, Monterey California (3 pages).

Midorikawa, Katsumi, et al., "Phase-Matched High-Order Harmonic Generation by Guided Intense Femtosecond Pulses," IEEE Journal of Selected Topics in Quantum Electronics, vol. 5, No. 6 (Nov./Dec. 1999) pp. 1475-1485.

Nisoli, M., et al., "Compression of high-energy laser pulses below 5fs", Optics Letters, (Apr. 15, 1997) vol. 22, No. 8, pp. 522-524, Optical Society of America.

Ogilvie, Jennifer P., et al., "Use of coherent control for selective two-photon fluorescence microscopy in live organisms," Optical Society of America (Jan. 2006) 8 pages.

Ohno, Kimihisa, et al., "Adaptive pulse shaping of phase and amplitude of an amplified femtosecond pulse laser by direct reference to frequency-resolved optical gating traces," J. Opt. Soc. Am. B vol. 19, No. 11 (Nov. 2002) pp. 2781-2790.

Pastirk, I. et al.; "2D (time-frequency) Femtosecond Four-Wave Mixing At $10^{14}$ W/cm$^2$: Molecular and Electronic Response;" Symposium on Optical Pulse and Beam Propagation III, Photonics West, 2001; 3 pages.

Pastirk, I. et al.; "Control and Characterization of Intramolecular Dynamics with Chirped Femtosecond Three-Pulse Four-Wave Mixing;" J. Phys. Chem. A, vol. 103, No. 49, Sep. 23, 1999; pp. 10226-10236.

Pastirk, I. et al.; "Femtosecond Ground State Dynamics of Gas Phase N2O4 and NO2," Chemical Physics letters, vol. 349, Nov. 23, 2001; pp. 71-78.

Pastirk, I. et al.; "Femtosecond Photo Echo and Virtual Echo Measurements of the Vibronic and Vibrational Coherence Relaxation Times of Iodine Vapor;" Chemical Physics Letters, vol. 333, Jan. 5, 2001; pp. 76-82.

Pastirk, I., et al., "Multidimensional Analytical Method Based on Binary Phase Shaping of Femtosecond Pulses," J. Phys. Chem. A, vol. 109, No. 11, Feb. 23, 2005; pp. 2413-2416.

Pastirk, I., et al., "No loss spectral phase correction and arbitrary phase shaping of regeneratively amplified femtosecond pulses using MIIPS," Optics Express, vol. 14, No. 20, (Oct. 2, 2006) pp. 9537-9543.

Pastrik, I. et al., "Sequences for Controlling Laser Excitation with Femtosecond Three-Pulse Four-Wave Mixing;" The Royal Society of Chemistry, vol. 113, 1999; pp. 401-424.

Pastrik, I. et al; "Quantum Control of the Yield of a Chemical Reaction;" J. Chem. Phys., vol. 108, No. 11, Mar. 15, 1998; pp. 4375-4378.

Peng, L. W. et al.; "Stepwise Solvation of the Intramolecular-Charge-Transfer Molecule $p$-(Dimethylamino)benzonitrile;" J. Phys. Chem., 91, 1987, p. 6162.

Perry, Michael D., et al., "Terawatt to Petawatt Subpicosecond Lasers", Articles, (May 13, 1994), vol. 264, Science.

PiStar Kinetic Circular Dichroism Spectrometer, http://www.phtophysics.com/pistar.php, Nov. 29, 2006; 3 pages.

Posthumus, J.H., "The dynamics of small molecules in intense laser fields," Reports on Progress in Physics, 67 (2004) Institute of Physics Publishing, pp. 623-665.

Quiroga-Teixeiro, M.L., et al., "Compression of optical solitons by conversion of nonlinear modes", J. Opt. Soc. Am. B, vol. 12, No. 6, (Jun. 1995), pp. 1110-1116, Optical Society of America.

QWPO-AS, Zero Order Waveplates—Air Spaced, Optical Components and Assemblies, www.cvilaser.com, published Nov. 21, 2005; pp. 8-9.

R. Wolleschensky et al.; "Characterization and Optimization of a Laser-Scanning Microscope in the Femtosecond Regime;" Applied Physics B 67, Lasers and Optics, 1998; pp. 87-94.

Reitze, D.H., et al., "Shaping of wide bandwidth 20 femtosecond optical pulses", Appl. Phys. Lett. 61 (11), (Sep. 14, 1992), pp. 1260-1262, American Institute of Physics.

Rodriguez, George, et al., "Coherent Ultrafast MI-FROG Spectroscopy of Optical Field Ionization in Molecular H2, N2, and O2," IEEE Journal on Selected Topics in Quantum Electronics, vol. 7, No. 4 (Jul./Aug. 2001) pp. 579-591.

Rosker, M. J. et al.; "Femtosecond Clocking of the Chemical Bond;" Science, vol. 241, Sep. 2, 1988; pp. 1200-1202.

Rosker, M. J. et al.; "Femtosecond Real-Time Probing of Reactions. I. The Technique;" J. Chem. Phys., vol. 89, No. 10, Nov. 15, 1988; pp. 6113-6127.

Sanders, A. W. et al.: "Observation of Plasmon Propagation, Redirection, and Fan-Out in Silver Nanowires" Nano Letters, American Chemical Society, Washington, DC, US, vol. 6, No. 8, Jun. 28, 2006, pp. 1822-1826, XP007901978, ISSN: 1530-6984.

ScanMail 10K—Scanna; Internet publication from Safer America; 2003.

Serbin, J., et al., "Femtosecond lasers as novel tool in dental surgery," applied surface science, 197-198 (2002) pp. 737-740.

Shimizu, Satoru, et al., "Spectral phase transfer for indirect phase control of sub-20-fs deep UV pulses," Optics Express, vol. 13, No. 17 (Aug. 22, 2005) pp. 6345-6353.

Siders, C.W., et al., "Blue-shifted third-harmonic generation and correlated self-guiding during ultrafast barrier suppression ionization of subatmospheric density noble gases," J. Opt. Soc. Am. B/vol. 13, No. 2 (Feb. 1996) pp. 330-335.

Spielmann, C., et al., "Ti: Sapphire Laser Produces Intense Sub-5-FS Pulses", Laser Focus World, May 97, vol. 33, Issue 5, p. 127.

Stockman, Mark I. et al.; "Coherent Control of Femtosecond Energy Localization in Nanosystems;" Physical Review Letters, vol. 88, No. 6, Feb. 11, 2002; pp. 067402-1-067402-4.

Surharev, Maxim et al.; "Coherent Control Approaches to Light Guidance in the Nanoscale;" The Journal of Chemical Physics 124, 2006; XP008086379; pp. 144707-1-144707-8.

Suzuki, Takayuki et al.; "Nontrivial Polarization Shaping of Femtosecond Pulses by Reference to the Results of Dual-Channel Spectral Interferomtry;" Applied Optics, vol. 43, No. 32, Nov. 10, 2004; pp. 6047-6050.

Szipöcs, Robert, et al., "Chirped multilayer coatings for broadband dispersion control in femtosecond lasers", Optics Letters, (Feb. 1, 1994), vol. 19, No. 3, Optical Society of America.

T.C. Weinacht et al.; "Toward Strong Field Mode-Selective Chemistry"; J. Phys. Chem. A, vol. 103, No. 49; 1999; pp. 10166-10168.

Tamaki, Y., "Phase-matched third-harmonic generation by nonlinear phase shift in a hollow fiber," Lasers and Optics Applied Physics B, vol. 67, (1998) pp. 59-63.

Ting, A., et al.; "Remote Atmospheric Breakdown for Standoff Detection by Using an Intense Short Laser Pulse," Applied Optics. Opt. Soc. America, USA, vol. 44, No. 25, XP002476098, Sep. 1, 2005; pp. 5315-5320.

Trebino, Rick, et al., "Using phase retrieval to measure the intensity and phase of ultrashort pulses: frequency-resolved optical gating", J. Opt. Soc. Am. A, vol. 10, No. 5, (May 1993), pp. 1101-1111, Optical Society of America.

Umstadter, D., et al., "Nonlinear Plasma Waves Resonantly Driven by Optimized Laser Pulse Trains", Physical Review Letters, vol. 72, No. 8, (Feb. 21, 1994), pp. 1224-1227, The American Physical Society.

Verluise, Frédéric, et al., "Arbitrary dispersion control of ultrashort optical pulses with acoustic waves," J. Opt. Soc. Am. B vol. 17, No. 1 (Jan. 2000) pp. 138-145.

von Vacano, Bernhard, et al., "Shaper-assisted collinear SPIDER: fast and simple broadband pulse compression in nonlinear microscopy," vol. 24, No. 5, (May 2007) J. Opt. Soc. Am. B, pp. 1091-1100.

Waner, M. J. et al.; "Imaging the Molecular Dimensions and Oligomerization of Proteins at Liquid/Solid Interfaces;" J. Phys. Chem. B, vol. 102, No. 9, 1998; pp. 1649-1657.

Warren, W.S., et al., "Coherent Control of Quantum Dynamics: The Dream is Alive", Articles, Science, (Mar. 12, 1993), vol. 259.

Wefers, Marc M., "Programmable phase and amplitude femtosecond pulse shaping", Optics Letters (Dec. 1, 1993), vol. 18, No. 23, pp. 2032-2034.

Wefers, Marc, et al., "Generation of high-fidelity programmable ultrafast optical waveforms", Optics Letters, (May 1, 1995), vol. 20, No. 9, Optical Society of America.

Weiner, "Encoding and decoding of femtosecond pulses", Optics Letters, (Apr. 1988), vol. 13, No. 4, Optical Society of America.

Weiner, A.M., "Enhancement of coherent charge oscillations in coupled quantum wells by femtosecond pulse shaping", J. Opt. Soc. Am. B, vol. 11, No. 12, (Dec. 1994), pp. 2480-2491, Optical Society of America.

Weiner, A.M., "Femtosecond Optical Pulse Shaping and Processing", Prog. Quant. Electr. (1995) vol. 19, pp. 161; 230-233.

Weiner, A.M., "Femtosecond pulse shaping using spatial light modulators," Review Article, Review of Scientific Instruments, vol. 71, No. 5 (May 2000) pp. 1929-1960.

Weiner, A.M., "High-resolution femtosecond pulse shaping", J. Opt. Soc. Am. B., vol. 5, No. 8, (Aug. 1988), pp. 1563-1572, Optical Society of America.

Weiner, A.M., "Programmable femtosecond pulse shaping by use of a multielement liquid-crystal phase modulator", Optics Letters, (Mar. 15, 1990), vol. 15, No. 6, pp. 326-328, Optical Society of America.

Weiner, A.M., "Spectral holography of shaped femtosecond pulses", Optics Letters, vol. 17, No. 3 (Feb. 1, 1992), pp. 224-226, Optical Society of America.

Weiner, A.M., et al., "Femtosecond multiple-pulse impulsive stimulated Raman scattering spectroscopy", J. Opt. Soc. Am. B., vol. 8, No. 6, (Jun. 1991), pp. 1264-1275.

Weiner, Andrew M., Programmable Shaping of Femtosecond Optical Pulses by Use of 128-Element Liquid Crystal Phase Modulator, (1992) vol. 28, No. 4, pp. 908-919, IEEE Journal of Quantum Electronics.

Wollenhaupt, M. et al.; "Femtosecond Laser Photoelectron Spectroscopy on Atoms and Small Molecules: Prototype Studies in Quantum Control;" Annu. Rev. Phys. Chem., 56, 2005; pp. 25-56.

Xu, B et al.; "Quantitative Investigation of the Multiphoton Intrapuse Interference Phase Scan Method for Simultaneous Phase Measurement and Compensation of Femtosecond Laser Pulses;" J. Opt. Soc. Am. B, vol. 23, No. 4, Apr. 2006; pp. 750-759.

Xu, J.H., et al., "Study of Pulse Compression from 1.5 μm Distributed Feedback Lasers by a Gires-Tournois Interferometer", Fiber and Integrated Optics, vol. 13, (1994), pp. 365-372.

Zhang, Q. et al.; "Concerted Elimination Dynamics From Highly Excited States;" Faraday Discussions, 108, 1997; pp. 63-80.

Zhang, Q. et al.; "Femtosecond Dynamics of Photoinduced Molecular Detachment From Halogenated Alkanes. II. Asynchronous Concerted Elimination of $I_2$ From $CH_2I_2$;" J. Chem. Phys., vol. 109, No. 11, Sep. 15, 1998; pp. 4428-4442.

Zhou, Jianping, et al., "Generation of 21-fs millijoule-energy pulses by use of Ti:sapphire", Optics Letters, vol. 19, No. 2, (Jan. 15, 1994), pp. 126-128, Optical Society of America.

"Coherent® Silhouette, Ultrafast Pulse Shaper," Key Features brochure. Web. Jan. 29, 2008 http://www.coherent.com/Lasers/index.cfm?Fuseaction=show.print&ID=1485.

"Coherent® Silhouette, Ultrafast Pulse Shaping and Measurement," brochure, (2007) 2 pages. Coherent, Inc.

Bonacina, Luigi, et al., "Multiobjective genetic approach for optimal control of photoinduced processes," Physical Review A. 76, The American Physical Society, (2007) pp. 023408-1 through 023408-5.

Bowlan, Pamela, et al., "Directly measuring the spatio-temporal electric field of focusing ultrashort pulses," Optics Express, vol. 15, No. 16 (2007) pp. 10219-10230.

Béjot, Pierre, et al., "Laser noise compression by filamentation at 400 nm in argon," Optics Express, vol. 15, No. 20 (Oct. 2007) pp. 13295-13309.

Chen, Bi-Chang, et al., "Characterization of a broadband pulse for phase controlled multiphoton microscopy by single beam SPIDER," Optics Letters, vol. 32, No. 16, Optical Society of America (Aug. 15, 2007) pp. 2411-2413.

Chung, Jung-Ho, "Ambiguity of Ultrashort Pulse Shapes Retrieved From the Intensity Autocorrelation and the Power Spectrum," IEEE Journal on Selected topics in Quantum Electronics, vol. 7, No. 4 (Jul./Aug. 2001) pp. 656-666.

Coello, Yves, "Interference without an interferometer: a different approach to measuring, compressing, and shaping ultrashort laser pulses," J. Opt. Soc. Am. B/vol. 25, No. 6 (Jun. 2008) pp. A140-A150.

Kubo, Atsushi, et al., "Femtosecond Imaging of Surface Plasmon Dynamics in a Nanostructured Silver Film," Nano Letters, vol. 5, No. 6 (2005) American Chemical Society, pp. 1123-1127.

Laarmann, T., et al., "Femtosecond pulse shaping as analytic tool in mass spectrometry of complex polyatomic systems," J Phys B-at Mol Opt 2008;41(7).

Lozovoy, Vadim V., et al., "Direct measurement of spectral phase for ultrashort laser pulses," Optics Express, vol. 16, No. 2 (Jan. 21, 2008) pp. 592-597.

May, Volkhard et al., "Theory of ultrafast nonresonant multiphoton transitions in polyatomic molecules: Basics and application to optimal control theory," J. Chem. Phys. 127 (2007) pp. 144102-1 through 144102-11.

Montgomery, Matthew A., "Elucidation of Control Mechanisms Discovered during Adaptive Manipulation of [Ru(dpb)3](PF6)2 emission in the Solution Phase," American Chemical Society, J. Phys. Chem. A, vol. 111, No. 8 (2007) pp. 1426-1433.

Nisoli, M., et al., "Generation of high energy 10 fs pulses by a new pulse compression technique," Appl. Phys. Lett., vol. 68, No. 20 (May 13, 1996) pp. 2793-2795.

Nuernberger, Patrick, "Femtosecond quantum control of molecular dynamics in the condensed phase," Invited Article, Physical Chemistry Chemical Physics, The Owner Societies, vol. 9 (2007) pp. 2470-2497.

Oron, Dan, et al., "Scanningless depth-resolved microscopy," Optics Express, vol. 13, No. 5 (Mar. 7, 2005).

Tada, Junji, "Adaptively controlled supercontinuum pulse from a microstructure fiber for two-photon excited fluorescence microscopy," Applied Optics, vol. 46, No. 15, (May 20, 2007) pp. 3023-3030.

Takasago, Kazuya, et al., "Design of Frequency-Domain Filters for Femtosecond Pulse Shaping," Part 1, No. 2A (Feb. 1996) pp. 624-629. Jpn. J. Appl. Phys.

Urbasch, Gunter, et al., "Distinctino of ortho- and para-Xylene by Femtosecond-Laser Mass Spectrometry," Communications, ChemPhysChem vol. 8 (2007) Wiley-VCH Verlag GmbH&Co. KGaA, Weinheim, pp. 2185-2188.

Wang, He, et al., "Generation of 0.5 mJ, few-cycle laser pulses by an adaptive phase modulator," Optics Express, vol. 16, No. 19 (Sep. 15, 2008) pp. 14448-14455.

Wnuk, Pawel, et al., "Coherent control and dark pulses in second harmonic generation," Optics Communications 272, ScienceDirect (2007) pp. 496-502.

Zang, Hegui, et al., "Study on Frequency-doubling Effect of the Dually Doped KTP Crystals," Journal of Synthetic Crystals vol. 29, No. 2 (May 2000).

Dong Gun Lee et al.; "Coherent Control of High-Order Harmonics with Chirped Femtosecond Laser Pulses"; Physical Review Letters, vol. 87, No. 24, Dec. 10, 2001; pp. 243902-1-243902-4.

M. Armstrong et al.; "Versatile seven-femtosecond pulse compressor of parametrically amplified pulses using adaptive optics: studies of the primary events in protein dynamics"; Applied Physics B 74 (Suppl), 2002; pp. S127-S132.

D.S. Chemla et al; "Ultrafast phase dynamics of coherent emission from excitons in GaAs quantum wells"; Physical Review B, vol. 50, No. 12, Sep. 15, 1995; pp. 8439-8453.

Jerome Tignon et al.; "Spectral Interferometry of Semiconductor Nanostructures"; IEEE Journal of Quantum Electronics, vol. 35, No. 4; Apr. 1999; pp. 510-522.

Arthur L. Smirl et al.; "Heavy-Hole and Light-Hole Quantum Beats in the Polarization State of Coherent Emission from Quantum Wells"; IEEE Journal of Quantum Electronics, vol. 35, No. 4; Apr. 1999; pp. 523-531.

John D. Hybl et al; "Two-dimensional Fourier transform electronic spectroscopy"; Journal of Chemical Physics, vol. 115, No. 14; Oct. 8, 2001; pp. 6606-6622.

C. Iaconis et al.; "Direct measurement of the two-point field correlation function"; Optics Letters, vol. 21, No. 21; Nov. 1, 1996; pp. 1783-1785.

A.M. Weiner et al.; "Femtosecond Pulse Sequences Used for Optical Manipulation of Molecular Motion"; Reports; Mar. 16, 1990; pp. 1317-1319.

Ch. Warmuth et al.; "Studying vibrational wavepacket dynamics by measuring fluorescence interference fluctuations"; Journal of Chemical Physics, vol. 112, No. 11; Mar. 15, 2000; pp. 5060-5069.

Ch. Warmuth et al.; "Molecular quantum dynamics in a thermal system: fractional wave packet revivals probed by random-phase fluorescence interferometry"; Journal of Chemical Physics, vol. 114, No. 22; Jun. 8, 2001; pp. 9901-9910.

G.G. Paulus et al.; "Absolute-phase phenomena in photoionization with few-cycle laser pulses"; Nature, vol. 414; Nov. 8, 2001; pp. 182-184.

Yaron Silberberg; "Physics at the attosecond frontier"; Nature, vol. 414, Nov. 29, 2001; pp. 494-495.

M. Hentschel et al.; "Attosecond metrology"; Nature, vol. 414; Nov. 29, 2001; pp. 509-513.

L. Lepetit et al.; "Linear techniques of phase measurement by femtosecond spectral interferometry for applications in spectroscopy"; J. Opt. Soc. Am. B, vol. 12, No. 12; Dec. 1995; pp. 2467-2474.

L. Lepetit et al.; "Two-dimensional nonlinear optics using Fourier-transform spectral interferometry"; Optics Letters, vol. 21, No. 8; Apr. 15, 1996; pp. 564-566.

K.C. Chu et al.; "Temporal interferometric measurement of femtosecond spectral phase"; Optics Letters, vol. 21, No. 22; Nov. 15, 1996; pp. 1842-1844.

W.J. Walecki et al.; "Characterization of the polarization state of weak ultrashort coherent signals by dual-channel spectral interferometry"; Optics Letters, vol. 22, No. 2; Jan. 15, 1997; pp. 81-83.

J.P. Likforman et al.; "Measurement of photon echoes by use of femtosecond Fourier-transform Spectral Interferometry"; Optics Letters, vol. 22, No. 14; Jul. 15, 1997; pp. 1104-1106.

Michel F. Emde et al.; "Spectral interferometry as an alternative to time-domain heterodyning"; Optics Letters, vol. 22, No. 17; Sep. 1, 1997; pp. 1338-1340.

X. Chen et al.; "Temporally and spectrally resolved amplitude and phase of coherent four-wave-mixing emission from GaAs quantum wells"; Physical Review B, vol. 56, No. 15; Oct. 15, 1997; pp. 9738-9743.

Christophe Dorrer; "Influence of the calibration of the detector on spectral interferometry"; J. Opt. Soc. Am. B; vol. 16, No. 7; Jul. 1999; pp. 1160-1168.

Allison W. Albrecht et al.; "Experimental distinction between phase shifts and time delays: Implications for femtosecond spectroscopy and coherent control of chemical reactions"; Journal of Chemical Physics, vol. 111, No. 24; Dec. 22, 1999; pp. 10934-10955.

Christophe Dorrer et al.; "Spectral resolution and sampling issues in Fourier-transform spectral interferometry"; J. Opt. Soc. Am. B, vol. 17, No. 10; Oct. 2000; pp. 1795-1802.

G. Roberts; "Abstract-Interference effects in femtosecond spectroscopy"; Philosophical Transactions of the Royal Society of London Series A—Mathematical Physical and Engineering Sciences; 360 (1794): 987-1021; May 15, 2002 (1 page).

B. Chatel et al.; "Role of quadratic and cubic spectral phases in ladder climbing with ultrashort pulses"; Physical Review A 70; 2004; pp. 053414-1-053414-10.

Richard S. Judson et al.; "Teaching Lasers to Control Molecules"; Physical Review Letters, vol. 68, No. 10; Mar. 9, 1992; pp. 1500-1503.

Michael Messina et al.; "Quantum control of multidimensional systems: Implementation within the time-dependent Hartree approximation"; J. Chem Phys. 104; Jan. 1996; pp. 173-182.

D.H. Schirrmeister et al; "Femtosecond pulse dependence of dissipation in molecular systems"; Chemical Physics Letters Dec. 4, 1998; pp. 383-390.

Herschel Rabitz et al.; "Optimal Control of Molecular Motion: Design, Implementation and Inversion"; Acc. Chem. Res., vol. 33, No. 8; 2000; pp. 572-578.

R. deVivie-Riedle et al.; "Design and interpretation of laser pulses for the control of quantum systems"; Applied Physics B; 2000; pp. 285-292.

Moshe Shapiro et al.; On the Origin of Pulse Shaping Control of Molecular Dynamics; J. Phys. Chem. A, vol. 105, No. 105; 2001; pp. 2897-2902.

Y.J. Yan et al.; "Pulse shaping and coherent Raman spectroscopy in condensed phases"; J. Chem. Phys 94 (2); Jan. 15, 1991; pp. 997-1001.

Bern Kohler et al.; "Mode-Locking Matter with Light"; J. Phys. Chem 1993, 97; pp. 12602-12608.

Jeffrey L. Krause et al.; "Optical control of molecular dynamics: Molecular cannons, reflectrons and wave-packet focusers"; J. Chem. Phys. 99(9); Nov. 1, 1993; pp. 6562-6578.

V. Engel et al; "Two-photon wave-packet interferometry"; J. Chem Phys. 100 (8); Apr. 15, 1994; pp. 5448-5458.

Jeffrey L. Krause et al.; "Quantum Control of Molecular Dynamics: The Strong Response Regime"; J. Phys. Chem; 1995, 99; pp. 13736-13747.

Jianwei Che et al.; "Detection and Control of Molecular Quantum Dynamics"; J. Phys. Chem.; 1995; pp. 14949-14958.

M. Sterling et al.; "Interrogation and control of condensed phase chemical dynamics with linearly chirped pulses: 12 in solid Kr"; J. Chem. Phys. 104; May 1, 1996; pp. 6497-6506.

Jianwei Che et al.; "Semiclassical Dynamics and Quantum Control in Condensed Phases: Application to 12 in a Solid Argon Matrix"; J. Phys. Chem. 1996, 100; pp. 7873-7883.

Jianshu Cao et al.; "A simple physical picture for quantum control of wave packet localization"; J. Chem Phys., 107; Aug. 1, 1997; pp. 1441-1450.

Kenji Mishima et al.; "A theoretical study on laser control of a molecular nonadiabatic process by ultrashort chirped laser pulses"; Journal of Chemical Physics, vol. 109., No. 5; Aug. 1, 1998; pp. 1801-1809.

H.A. Kim et al.; "Expanded concept of the adiabatic population transfer using dressed states"; Physical Review A, vol. 59, No. 2; Feb. 1999; pp. 1404-1407.

Jianshu Cao et al.; "Molecular pie pulses: Population inversion with positively chirped short pulses"; Journal of Chemical Physics, vol. 113, No. 5; Aug. 1, 2000; pp. 1898-1909.

A.J. Wurzer et al.; "Highly localized vibronic wavepackets in large reactive molecules"; Applied Phys. B 71, 2000; pp. 405-409.

F. Legare et al.; "Laser pulse control of Raman processes by chirped non-adiabatic passage"; Journal of Raman Spectroscopy; 2000; pp. 15-23.

Moshe Shapiro et al.; "Coherently Controlled Asymmetric Synthesis with Achiral Light"; Physical Review Letters, vol. 84, No. 8; Feb. 21, 2000; pp. 1669-1672.

Gabriel Turinici et al.; "Quantum wavefunction controllability"; Chemical Physics 267; 2001; pp. 1-9.

M. Gruebele; "Fully quantum coherent control"; Chemical Physics 267; 2001; pp. 33-46.

V.S. Malinovsky et al.; "General theory of population transfer by adiabatic rapid passage with intense, chirped laser pulses"; The European Physical Journal D 14; 2001; pp. 147-155.

Z.W. Shen et al.; "Selective preparation of ground state wave-packets: a theoretical analysis of femtosecond pump-dump-probe experiments on the potassium dimmer"; The European Physical Journal D 14; 2001; pp. 167-172.

Sanislav S. Bychkov et al.; "Laser coherent control of molecular chiral states via entanglement of the rotational and torsional degrees of freedom"; Journal of Raman Spectroscopy; 2002; pp. 962-973.

S.E. Harris; "Control of Feshbach resonances by quantum interference"; Physical Review A66; 2002; pp. 010701-1-010701-4.

John M. Jean et al.; "Application of a multilevel Redfield theory to electron transfer in condensed phases"; J. Chem. Phys. 96; Apr. 15, 1992; pp. 5827-5842.

Bjarne Amstrup et al.; "Control of HOD photodissociation dynamics via bond-selective infrared multiphoton excitation and a femtosecond ultraviolet laser pulse"; J. Chem. Phys., vol. 97, No. 11; Dec. 1, 1992; pp. 8285-8295.

L.D. Ziegler et al.; "Nonlinear polarization description of phase-locked pulse-pair spectroscopy"; J. Chem. Phys., vol. 97, No. 7; Oct. 1, 1992; pp. 4704-4713.

S. Meyer et al.; "Photoelectron distributions from femtosecond pump/probe excitation with chirped probe pulses"; Journal of Chemical Physics, vol. 108, No. 18; pp. 7631-7636.

V.M. Akulin et al.; "Laser Control of Atomic Motion inside Diatomic Molecules"; J. Phys. Chem. A, vol. 102, No. 23; 1998; pp. 4310-4320.

Jianshu Cao et al.; "Molecular Pi Pulse for Total Inversion of Electronic State Population"; Physical Review Letters, vol., 80, No. 7; Feb. 16, 1998; pp. 1406-1409.

Moshe Shapiro et al.; "Nonadiabatic wave packet dynamics: Experiment and theory in IBr"; Journal of Chemical Physics, vol. 110, No. 5; Feb. 1, 1999; pp. 2465-2473.

Zhenwen Shen et al.; "Pump-dump control and the related transient absorption spectroscopies"; Journal of Chemical Physics, vol. 110, No. 15; Apr. 15, 1999; pp. 7192-7201.

Kenji Mishima et al.; "Theoretical study on quantum control of photodissociation and photodesorption dynamics by femtosecond chirped laser pulses"; Journal of Chemical Physics, vol. 110, No. 16; Apr. 22, 1999; pp. 7756-7769.

H.S. Moon et al.; "Coherence control using the ratio of Rabi frequencies for complete coherent inversion in a four-level system"; J. Phys. B At. Mol. Phys. vol. 32; 1999; pp. 987-999.

Jeffrey A. Cina; "Nonlinear wavepacket interferometry for polyatomic molecules"; Journal of Chemical Physics, vol. 113, No. 21; Dec. 1, 2000; pp. 9488-9496.

F. Gelmukhanov et al.; "Dynamics of two-photon absorption by molecules and solutions"; J. Opt. Soc. Am. B, vol. 19, No. 5, May 2002; pp. 937-945.

Philip H. Bucksbaum; "Ultrafast control"; Nature magazine, vol. 421; Feb. 6, 2003; pp. 593-594. Kuhn & Weyn SR2 Sep. 4, 2001.

Christopher J. Bardeen et al.; "Effec of Pulse Shape on the Efficiency of Multiphoton Processes: Implications for Biological Microscopy"; Journal of Biomedical Optics, vol. 4, No. 3; Jul. 1999; pp. 362-367.

T. Hornung et al.; "Optimal control of one- and two-photon transitions with shaped femtosecond pulses and feedback"; Applied Physics B 71; 2000; pp. 277-284.

T. Brixner et al.; "Photoselective adaptive femtosecond quantum control in the liquid phase"; Nature magazine, vol. 414; Nov. 2001; pp. 57-60.

B.J. Pearson et al.; "Coherent control using adaptive learning algorithms"; Physical Review A, vol. 63; 2001; pp. 063412-1-063412-12.

Jennifer L. Herek et al.; "Quantum control of energy flow in light harvesting"; Nature magazine, vol. 417; May 30, 2002; pp. 533-535.

Nirit Dudovich et al.; "Single-pulse coherently controlled nonlinear Raman spectroscopy and microscopy"; Nature magazine, vol. 418; Aug. 1, 2002; pp. 512-514.

T. Brixner et al.; "Liquid-phase adaptive femtosecond quantum control: Removing intrinsic intensity dependencies"; Journal of Chemical Physics, vol. 118, No. 8; Feb. 22, 2003; pp. 3692-3701.

R. Netz et al.; "Observation of Selectivity of Coherent Population Transfer Induced by Optical Interference"; Physical Review Letters, vol. 90, No. 6; Feb. 14, 2003; pp. 063001-1-063001-4.

D.W. Schumacher et al.; "Phase Dependence of Intense Field Ionization"; Physical Review A, vol. 54, No. 5; Nov. 1996; pp. 4271-4278.

Christopher J. Bardeen et al.; "Feedback quantum control of molecular electronic population transfer"; Chemical Physics Letters 280; 1997; pp. 151-158.

Christopher J. Bardeen et al.; "Quantum Control of Population Transfer in Green Fluorescent Protein by Using Chirped Femtosecond Pulses"; J. Am. Chem. Soc., vol. 120, No. 50; 1998; 13023-13027.

Doron Meshulach et al.; "Coherent quantum control of two-photon transitions by a femtosecond laser pulse"; Nature magazine, vol. 396; Nov. 19, 1998; pp. 239-242.

A. Baltuska et al.; "Attosecond control of electronic processes by intense light fields"; Nature magazine, vol. 421; Feb. 6, 2003; pp. 611-615.

D.J. Maas et al.; "Population transfer via adiabatic passage in the rubidium quantum ladder system"; Physical Review A, vol. 59, No. 2; Feb. 1999; pp. 1374-1381.

Zohar Amitay et al.; "Phase-tailoring molecular wave packets to time shift their dynamics"; Chemical Physics 267; 2001; pp. 141-149.

T.C. Weinacht et al.; "Coherent learning control of vibrational motion in room temperature molecular gases"; Chemical Physics Letters 344; 2001; pp. 333-338.

R. van Leeuwen et al.; "Manipulation of differential electron yields via autoionizing wave-packet control"; Physical Review A, vol. 63; 2001; pp. 033403-1-033403-5.

Dan Oron et al.; "Quantum control of coherent anti-Stokes Raman processes"; Physical Review A, vol. 65; 2002; pp. 043408-1-043408-4.

Nirit Dudovich et al.; "Coherent Transient Enhancement of Optically Induced Resonant Transitions"; Physical Review Letters, vol. 88, No. 12; Mar. 25, 2002; pp. 123004-1123004-4.

Jerome Degert et al.; "Realization of a Time-Domain Fresnel Lens with Coherent Control"; Physical Review Letters, vol. 89, No. 20; Nov. 11, 2002; pp. 203003-1-203003-4.

M. Wollenhaupt et al.; "Interferences of Ultrashort Free Electron Wave Packets"; Physical Review Letters, vol. 89, No. 17; Oct. 21, 2002; pp. 173001-1-173001-4.

R. Teets et al.; "Coherent Two-Photon Excitation by Multiple Light Pulses"; Physical Review Letters, vol. 38, No. 14; Apr. 4, 1977; lags. 760-764.

R.R. Jones; "Multiphoton Ionization Enhancement Using Two Phase-Coherent Laser Pulses"; Physical Review Letters, vol. 75, No. 8; Aug. 21, 1995; pp. 1491-1494.

D.J. Maas et al.; "Vibrational ladder climbing in NO by ultrashort infrared laser pulses"; Chemical Physics Letters 270; May 16, 1997; pp. 45-49.

Christopher J. Bardeen et al.; "Quantum control of I2 in the gas phase and in condensed phase solid Kr matrix"; J. Chem. Phys., vol. 106, No. 20; May 22, 1997; pp. 8486-8503.

D.J. Maas et al.; Vibrational ladder climbing in NO by (sub)picosecond frequency-chirped infrared laser pulses'; Chemical Physics Letters 290; 1998; pp. 75-80.

Vladislav V. Yakovlev et al.; "Chirped pulse enhancement of multiphoton absorption in molecular iodine"; Journal of Chemical Physics, vol. 108, No. 6, Feb. 8, 1998; pp. 2309-2313.

Radoslaw Uberna et al.; "Phase and amplitude control in the formation and detection of rotational wave packets in the E1Eg state of Li2"; Journal of Chemical Physics, vol. 108, No. 22; pp. 9259-9274.

John M. Papanikolas et al.; "Erratum: Manipulation of rovibrational wave packet composition in the Li2 E(Eg) shelf state using intermediate state selection and shaped femtosecond laser pulses"; J. Chem Phys. 107, 4172; 1997; p. 10830.

T.C. Weinacht et al.; "Measurement of the Amplitude and Phase of a Sculpted Rydberg Wave Packet"; Physical Review Letters; vol. 80, No. 25; Jun. 22, 1998; pp. 5508-5511.

Radoslaw Uberna et al.; "Phase control of wavepacket dynamic using shape femtosecond pulses"; Faraday Discuss, vol. 113; 1999; pp. 385-400.

Mohamed Aziz Bouchene et al.; "Wavepacket interferometry with chirped pulses"; J. Phys. B At. Mol. Opt. Phys. 32; 1999; pp. 5167-5177.

D.J. Maas et al.; "Rotational interference in vibrational ladder climbing in NO by chirped infrared laser pulses"; Physical Review A, vol. 60, No. 2; Aug. 1999; pp. 1351-1362.

R. van Leeuwen et al.; "Coherent Control of the Energy and Angular Distribution of Autoionized Electrons"; Physical Review Letters, vol. 82, No. 14; Apr. 5, 1999; pp. 2852-2855.

Celine Nicole et al.; "Saturation of wave-packet interferences: Direct observation of spin precession in potassium atoms"; Physical Review A, vol. 60, No. 3; Sep. 1999; pp. R1755-R1758.

Mohamed Aziz Bouchene et al.; "Interplay between wave packet interferences and second harmonic generation"; Optics Communications 181; 2000; pp. 327-336.

Radoslaw Uberna et al.; "Ultrafast spectroscopy of wavelength-dependent coherent photoionization cross sections of Li2 wave packets in the E1Eg state: The role of Rydberg states"; Journal of Chemical Physics, vol. 114, No. 23; Jun. 15, 2001; pp. 10311-10320.

Lorenzo Pesce et al.; "Quantum dynamics simulation of the ultrafast photoionization of Li2"; Journal of Chemical Physics, vol. 114, No. 3; Jan. 15, 2001; pp. 1259-1271.

M.F. DeCamp et al.; "Dynamics and coherent control of high-amplitude optical phonons in bismuth"; Physical Review B, vol. 64; 2001; pp. 092301-1-092301-3.

J. Ahn et al.; "Quantum Phase Retrieval of a Rydberg Wave Packet Using a Half-Cycle Pulse"; Physical Review Letters, vol. 86, No. 7; Feb. 12, 2001; pp. 1179-1182.

Sebastien Zamith et al.; "Observation of Coherent Transients in Ultrashort Chirped Excitation of an Undamped Two-Level System"; Physical Review Letters, vol. 87, No. 3; Jul. 16, 2001; pp. 033001-1-033001-4.

Hans U. Stauffer et al.; "Simultaneous phase control of Li2 wave packets in two electronic states"; Journal of Chemical Physics, vol. 116, No. 3; Jan. 15, 2002; pp. 946-954.

Joshua B. Ballard et al.; "Optimization of wave packet coefficients in Li 2 using an evolutionary algorithm: The role of resonant and nonresonant wavelengths"; Journal of Chemical Physics, vol. 116, No. 4; Jan. 22, 2002; pp. 1350-1360.

Elizabeth Mirowski et al.; "Effect of nonresonant frequencies on the enhancement of quantum beat amplitudes in rovibrational states of Li2: The role of state spacing"; Journal of Chemical Physics, vol. 117, No. 24; Dec. 22, 2002; pp. 11228-11238.

S.N. Pisharody et al.; "Phase-controlled stair-step decay of autoionizing radial wave packets"; Physical Review A, vol. 65; 2002; pp. 033418-1-033418-10.

R. Netz et al.; "Coherent population dynamics of a three-level atom in spacetime"; Physical Review A, vol. 65; pp. 043406-1-043406-12.

Joshua B. Ballard et al.; "Simultaneous control of time-dependent population transfer dynamics and wave-packet quantum interferences in Li2 by shaped ultrafast pulses"; Physical Review A 66; 2002; pp. 043402-1-043402-7.

Dan Oron et al.; "Narrow-Band Coherent Anti-Stokes Raman Signals from Broad-Band Pulses"; Physical Review Letters, vol. 88, No. 6; Feb. 11, 2002; pp. 063004-1-063004-4.

M.M. Salour et al.; "Observation of Ramsey's Interference Fringes in the Profile of Doppler-Free Two-Photon Resonances"; Physical Review Letters, vol. 38, No. 14; Apr. 4, 1977; pp. 757-760.

N. F. Scherer et al.; "Time resolved dynamics of isolated molecular systems studied with phase-locked femtosecond pulse pairs"; J. Chem Phys. vol. 93, No. 1; Jul. 1, 1990; pp. 856-857.

J.S. Melinger et al.; "Adiabatic population inversion in I2 vapor with picosecond laser pulses"; J. Chem Phys. vol. 95, No. 3; Aug. 1, 1991; pp. 2210-2213.

J.J. Gerdy et al.; "Femtosecond selective control of wave packet population"; Chemical Physics Letters, vol. 171, No. 1/2; Jul. 27, 1990; pp. 1-4.

Norbert F. Scherer et al.; "Fluorescence-detected wave packet interferometry: Time resolved molecular spectroscopy with sequences of femtosecond phase-locked pulses"; J. Chem. Phys., vol. 95, No. 3; Aug. 1, 1991; pp. 1487-1511.

N. F. Scherer et al.; "Fluorescence-detected wave packet interferometry. II. Role of rotations and determination of the susceptibility"; J. Chem. Phys., vol. 96, No. 6; Mar. 15, 1992; pp. 4180-4194.

L.D. Noordam et al.; "Redistribution of Rydberg States by Intense Picosecond Pulses"; Physical Review Letters, vol. 68, No. 10; Mar. 9, 1992; pp. 1496-1499.

J.S. Melinger et al.; "Generation of Narrowband Inversion with Broadband Laser Pulses"; vol. 68, No. 13; Mar. 30, 1992; pp. 2000-2003.

B. Broers et al.; "Efficient Population Transfer in a Three-Level Ladder System by Frequency-Swept Ultrashort Laser Pulses"; Physical Review Letters, vol. 69, No. 14; Oct. 5, 1992; pp. 2062-2065.

R.R. Jones et al.; "Ramsey Interference in Strongly Driven Rydberg Systems"; Physical Review Letters, vol. 71, No. 16; Oct. 18, 1993; pp. 2575-2578.

J.F. Christian et al.; "Rubidium electronic wavepackets probed by a phase-sensitive pump-probe technique"; Optics Communications, vol. 103, No. 1/2; Nov. 1, 1993; pp. 79-84.

J.S. Melinger et al.; "Adiabatic population transfer with frequency-swept laser pulses"; J. Chem. Phys. vol. 101, No. 8; Oct. 15, 1994; pp. 6439-6454.

P. Balling et al.; "Interference in climbing a quantum ladder system with frequency-chirped laser pulses"; Physical Review A, vol. 50, No. 5; Nov. 1994; pp. 4276-4285.

D.W. Schumacher et al.; "Phase Dependence of Intense Field Ionization: A Study Using Two Colors"; Physical Review Letters, vol. 73, No. 10; Sep. 5, 1994; pp. 1344-1347.

L. Marmet et al.; "Observation of Quasi-Landau Wave Packets"; Physical Review Letters, vol. 72, No. 24; Jun. 13, 1994; pp. 3779-3782.

Valerie Blanchet et al.; "One-color coherent control in Cs2 Observation of 2.7 fs beats in the ionization signal"; Chemical Physics Letters, vol. 233; Feb. 25, 1995; pp. 491-499.

R.R. Jones et al.; "Bound-state interferometry using incoherent light"; J. Phys. B 28 At. Mol. Opt. Phys.; 1995; pp. L405-L411.

D.W. Schumacher et al.; "Programmable cesium Rydberg wave packets"; Physical Review A, vol. 52, No. 6; Dec. 1995; pp. 4719-4726.

R.R. Jones; "Interference Effects in the Multiphoton Ionization of Sodium"; Physical Review Letters, vol. 74, No. 7; Feb. 13, 1995; pp. 1091-1094.

Bern Kohler et al.; "Quantum Control of Wave Packet Evolution with Tailored Femtosecond Pulses"; Physical Review Letters, vol. 74, No. 17; Apr. 24, 1995; pp. 3360-3363.

M. Ovchinnikov et al.; "Quantum interference in resonant Raman spectra of I2 in condensed media"; J. Chem. Phys., vol. 106, No. 13; Apr. 1, 1997; pp. 5775-5778.

Richard M. Williams et al.; "Compositional control of rovibrational wave packets in the E(1Eg) "shelf" state of Li2 via quantum-state-resolved intermediate state selection"; J. Chem. Phys. vol. 106, No. 20; May 22, 1997; pp. 8310-8323.

John M. Papanikolas et al.; "Manipulation of rovibrational wave packet composition in the Li2 E(1Eg) shelf state using intermediate state selection and shaped femtosecond laser pulses"; J. Chem. Phys., vol. 107, No. 11; Sep. 15, 1997; pp. 4172-4178.

Valerie Blanchet et al.; "Temporal Coherent Control in Two-Photon Transitions: From Optical Interferences to Quantum Interferences"; Physical Review Letters, vol. 78, No. 14; Apr. 7, 1997; pp. 2716-2719.

R. Zadoyan et al.; "Wavepacket diagnosis with chirped probe pulses"; Chemical Physics, vol. 233; 1998; pp. 353-363.

M.A. Bouchene et al.; "Temporal coherent control induced by wave packet interferences in one and two photon atomic transitions"; The European Physical Journal D, vol. 2; 1998; pp. 131-141.

Valerie Blanchet et al.; "Temporal coherent control in the photoionization of Cs2: Theory and experiment"; Journal of Chemical Physics, vol. 108, No. 12; Mar. 22, 1998; pp. 4862-4876.

R.A. Bartels et al.; "Nonresonant Control of Multimode Molecular Wave Packets at Room Temperature"; Physical Review Letters, vol. 88, No. 3; Jan. 21, 2002; pp. 033001-1 through 033001-4.

T. Brixner et al.; "Abstract—Femtosecond quantum control"; Advances in Atomic, Molecular, and Optical Physics, vol. 46; 46: 1-54; 2001 (1 page).

T. Brixner et al.; "Abstract—Photoselective adaptive femtosecond quantum control in the liquid phase"; Nature; 414 (6859): 57-60; Nov. 1, 2001 (1 page).

B. Dayan et al.; "Coherent control with broadband squeezed vacuum"; arXiv:quant-ph/0302038 v1; Feb. 5, 2003 (4 pages).

B. Dayan et al.; "Two Photon Absorption and Coherent Control with Broadband Down-Converted Light"; Physical Review Letters, vol. 93, No. 2; Jul. 9, 2004; pp. 023005-1023005-4.

B. Dayan et al.; "Nonlinear Interactions with an Ultrahigh Flux of Broadband Entangled Photons"; Physical Review Letters, PRL 94; Feb. 4, 2005, 2004; pp. 043602-1-043602-4.

N. Dudovich et al.; "Single-pulse coherent anti-Stokes Raman spectroscopy in the fingerprint spectral region"; J. of Chem. Phys., vol. 118, No. 20; May 22, 2003; pp. 9208-9215.

D. Oron et al.; "Femtosecond Phase-and-Polaration Control for Background-Free Coherent Anti-Stokes Raman Spectroscopy"; Physical Review Letters, vol. 90, No. 91; May 30, 2003; pp. 213902-1-213902-4.

N. Dudovich et al.; "Quantum Control of the Angular Momentum Distribution in Multiphoton Absorption Processes"; Physical Review Letters, vol. 93, No. 10; Mar. 12, 2004; pp. 103003-1-103003-4.

D. Oron et al.,; "All-optical processing in coherent nonlinear spectroscopy"; Physical Review A 70; 2004; pp. 023415-1-023415-4.

J.G. Underwood et al.,; "Switched Wave Packets: A Route to Nonperturbative Quantum Control"; Physical Review Letters, vol. 90, No. 22; Jun. 6, 2003; pp. 223001-1-223001-4.

M. Renard et al.; "Controlling ground-state rotational dynamics of molecules by shaped femtosecond laser pulses"; Physical Review A 69; 2004; 043401-1-043401-6.

A. Powe et al.; "Molecular Fluorescence, Phosphorescence, and Chemiluminescence Spectrometry"; Anal. Chem., vol. 76, No. 15; Aug. 15, 2004; pp. 4614-4634.

D. Abramavicius et al.; "Disentangling multidimensional femtosecond spectra of excitons by pulse shaping with coherent control"; J. of Chem. Phys., vol. 120, No. 18; May 8, 2004; pp. 8373-8378.

M.C. Chen et al.; "Coherent control multiphoton processes in semiconductor saturable Bragg reflector with freezing phase algorithm"; Appl. Phys. B 80; 2005; pp. 333-340.

W. Wohlleben et al.; "Coherent Control for Spectroscopy and Manipulation of Biological Dynamics"; Chem. Phys. Chem., 6; 2005; pp. 850-857.

T. Okada et al.; "Optical control of two-photon excitation efficiency of α-perylene crystal by pulse shaping"; Amer. Inst. of Phys., vol. 121, No. 13; Oct. 1, 2004; pp. 6386-6391.

V. Prokhorenko et al.; "Coherent control of the population transfer in complex sovated molecules at weak excitation. An experimental study"; The J. of Chem. Phys., 122; 2005; 184502-1-184502-11.

A. Prakelt et al.; "Phase control of two-photon transition with shaped femtosecond laser-pulse sequences"; Physical Review A 70; 2004; pp. 063407-1-06407-10.

B.J. Pearson et al.; "Control of Raman Lasing in the Nonimpulsive Regime"; Physical Review Letters, vol. 92, No. 24; Jun. 18, 2004; pp. 243003-1-243003-4.

Derryck T. Reid; "Algorithm for Complete and Rapid Retrieval of Ultrashort Pulse Amplitude and Phase from a Sonogram"; IEEE Journal of Quantum Electronics; vol. 35, No. 11, Nov. 1999; pp. 1584-1589.

I.G. Cormack et al.; "Rapid measurement of ultrashort-pulse amplitude and phase from a two-photon absorption sonogram trace"; J. Opt. Soc. Am. B; vol. 18, No. 9, Sep. 2001; pp. 1377-1382.

E. Tokunaga et al.; "Frequency-domain interferometer for femtosecond time-resolved phase spectroscopy"; Optics Letters, vol. 17, No. 16; Aug. 15, 1992, pp. 1131-1133.

Victor Wong et al.; "Analysis of ultrashort pulse-shape measurement using linear interferometers"; Optics Letters, vol. 19, No. 4; Feb. 15, 1994; pp. 287-289.

Victor Wong et al.; "Linear filter analysis of methods for ultrashort-pulse-shape measurements"; J. Opt.Soc. Am. B, vol. 12, No. 8; Aug. 1995; pp. 1491-1499.

David M. Jonas et al.; "Femtosecond Wavepacket Spectroscopy: Influence of Temperature, Wavelength and Pulse Duration"; J. Phys. Chem.; 1995; pp. 2594-2608.

J. Peatross et al.; "Temporal decorrelation of short laser pulses"; J. Opt. Soc. Am. B, vol. 15, No. 1; Jan. 1998; pp. 216-222.

McGraw-Hill Encyclopedia of Science & Technology, 6th Ed.; "Mass spectrometry"; 1987; pp. 492-502 (12 pages).

Ocean Optics Inc.; "HR4000 High-resolution Spectrometer" http://oceanoptics.com/products/hr4000.asp; Jun. 25, 2005 (p. 1 of 4-p. 4 of 4).

Ocean Optics Inc.; "USB2000 Miniature Fiber Optic Spectrometer" http://oceanoptics.com/products/usb2000.asp; Jun. 25, 2005 (p. 1 of 7-p. 6 of 7).

Ocean Optics Inc.; "S2000 Miniature Fiber Optic Spectrometer" http://oceanoptics.com/products/s2000.asp; Jun. 25, 2005 (p. 1 of 4-p. 4 of 4).

M. Schurenberg et al.; "Abstract—Laser desorption/ionization mass spectrometry of peptides and proteins with particle suspension matrixes"; Analytical Chemistry; 71 (1): 221-229; Jan. 1, 1999 (1 page).

F. Hillenkamp et al.;"Abstract—Matrix-assisted laser desorption/ionisation, an experience"; International Journal of Mass Spectrometry; 200 (1-3): 71-77; Dec. 25, 2000 (1 page).

M.O. Scully, et al.; "Fast CARS: Engineering a laser spectroscopic technique for rapid identification of bacterial spores"; PNAS; vol. 99, No. 17; Aug. 20, 2002; pp. 10994-11001.

K.D. Belfield et al.; "Multiphoton-absorbing organic materials for microfabrication, emerging optical applications and non-destructive three-dimensional imaging"; J. of Phys. Organic Chem., 13; 2000; pp. 837-849.

B. Natarajan et al.; "Abstract-Innovative pulse shaping for high-performance wireless TDMA"; IEEE Communications Letters; 5 (9): 372-374; Sep. 2001 (1 page).

A. Pe're et al.; Optical Code-Division Multiple Access Using Broad-Band Parametrically Generated Light; J. of Lightwave Tech.; vol. 22, No. 6; Jun. 2004; pp. 1463-1471.

J.J. Garcia-Ripoll et al.; "Speed Optimized Two-Qubit Gates with Laser Coherent Control Techniques for Ion Trap Quantum Computing"; Physical Review Letters, vol. 91, No. 15; Oct. 10, 2003; pp. 157901-1-157901-4.

J. Ahn et al.; "Information Storage and Retrieval Through Quantum Phase"; Science Magazine, vol. 287; Jan. 21, 2000; pp. 463-465.

Greg Taft et al.; "Measurement of 10-fs Laser Pulses"; IEEE Journal of Selected Topics in Quantum Electronics, vol. 2, No. 3, Sep. 1996; pp. 575-585.

Daniel J. Kane et al.; "Simultaneous measurement of two ultrashort laser pulses from a single spectrogram in a single shot"; Optical Society of America; vol. 14, No. 4, Apr. 1997; pp. 935-943.

Peter J. Delfyett et al.; "Joint Time-Frequency Meaurements of Mode-Locked Semiconductor Diode Lasers and Dynamics Using Frequency-Resolved Optical Gating"; IEEE Journal of Quantum Electronics, vol. 35, No. 4, Apr. 1999; pp. 487-500.

David N. Fittinghoff et al.; "Frequency-Resolved Optical Gating Measurement of Ultrashort Pulses Passing Through a High Numerical Aperture Objective"; IEEE Journal of Quantum Electronics, vol. 35, No. 4, Apr. 1999; pp. 479-486.

Andrius Baltuska et al.; "Second-Harmonic Generation Frequency-Resolved Optical Gating in the Single-Cycle Regime"; IEEE Journal of Quantum Electronics, vol. 35, No. 4, Apr. 1999; pp. 459-478.

Hilary K. Eaton et al.; "Investigating Nonlinear Femtosecond Pulse Propagation with Frequency-Resolved Optical Gating"; IEEE Journal of Quantum Electronics, vol. 35, No. 4, Apr. 1999; pp. 451-458.

Craig W. Siders et al.; "Multipulse Interferometric Frequency-Resolved Optical Gating"; IEEE Journal of Quantum Electronics, vol. 35, No. 4, Apr. 1999; pp. 432-440.

Atsushi Yabushita et al.; "SHG FROG and XFROG methods for phase/intensity characterization of pulses propagated through an absorptive optical medium"; Optics Communications; Oct. 15, 2001; pp. 227-232.

Roger G.M.P. Koumans et al.; "Time-Resolved Optical Gating Based on Dispersive Propagation: A New Method to Characterize Optical Pulses"; IEEE Journal of Quantum Electronics, vol. 36, No. 2, Feb. 2000; pp. 137-144.

Daniel J. Kane et al.; "Convergence test for inversion of frequency-resolved optical gating spectrograms"; Optics Letters, vol. 25, No. 16, Aug. 15, 2000; pp. 1216-1218.

Julie A. Gruetzmacher et al.; "Time and Frequency-Gated FID: a New Approach to Study the Vibrational Dephasing of Water"; Ultrafast Phenomena XII, 66; pp. 530-532.

Juan L.A. Chilla et al.; "Analysis of a Method of Phase Measurement of Ultrashort Pulses in the Frequency Domain"; IEEE Journal of Quantum Electronics, vol. 27, No. 5, May 1991; pp. 1228-1235.

David N. Fittinghoff et al.; "Noise sensitivity in frequency-resolved optical-gating measurements of ultrashort pulses"; J. Opt. Soc. Am. B, vol. 12, No. 10, Oct. 1995; pp. 1955-1967.

Noriaki Tsurumachi et al.; "Interferometric observation of femtosecond free induction decay"; Optics Letters, vol. 19, No. 22, Nov. 15, 1994; pp. 1867-1869.

C. Dorrer et al.; "Characterization of chirped-pulse amplification systems with spectral phase interferometry for direct electric-field reconstruction"; Applied Physics B 70 (Suppl.), 2000; pp. S77-S84.

C. Radzewicz et al.; "A poor man's FROG"; Optics Communications, Dec. 15, 2000; pp. 329-333.

C. Dorrer et al.; "Spatio-temporal characterization of the electric field of ultrashort optical pulses using two-dimensional shearing interferometry"; Applied Physics B74 (Suppl.), 2002; pp. S209-S217.

K.H. Hong et al.; "Time-frequency analysis of chirped femtosecond pulses using Wigner distribution function"; Applied Physics B74 (Suppl), 2002; pp. S231-S236.

Christophe Dorrer et al.; "Accuracy criterion for ultrashort pulse characterization techniques: application to spectral phase interferometry for direct electric field reconstruction"; Appl. Phys. B 74, vol. 19, No. 5, May 2002 ; pp. 1019-1029.

Kazunori Naganuma et al; "General Method for Ultrashort Light Pulse Chirp Measurement"; IEEE Journal of Quantum Electronics, vol. 25, No. 5; Jun. 1989; pp. 1225-1233.

Y. Ding et al.; "Time-Domain Image Processing Using Dynamic Holography"; IEEE Journal of Selected Topics in Quantum Electronics, vol. 4, No. 2; Mar./Apr. 1998; pp. 332-341.

Chris Iaconis et al; "Self-Referencing Spectral Interferometry for Measuring Ultrashort Optical Pulses"; IEEE Journal of Quantum Electronics, vol. 35, No. 4; Apr. 1999; pp. 501-509.

Jung-Ho Chung et al.; "Ambiguity of Ultrashort Pulse Shapes Retrieved From the Intensity Autocorrelation and the Power Spectrum"; IEEE Journal on Selected Topics of Quantum Electronics, vol. 7, No. 4; Jul./Aug. 2001; pp. 656-666.

V. Kabelka et al.; "Time-frequency imaging of a single ultrashort light pulse from anularly resolved autocorrelation"; Optics Letters, vol. 20, No. 1; Jun. 1, 1995; pp. 1301-1303.

Paul R. Bolton et al.; "Propagation of intense, ultrashort laser pulses through metal vapor: refraction-limited behavior for single pulses"; J. Opt. Soc. Am. B, vol. 13, No. 2; Feb. 1996; pp. 336-346.

Jun-Koo Rhee et al.; "Real-time dispersion analyzer of femtosecond laser pulses with use of a spectrally and temporally resolved upconversion technique"; J. Opt. Soc. Am. B, vol. 13, No. 8; Aug. 1996; pp. 1780-1785.

Marco A. Krumbugel et al.; "Direct ultrashort-pulse intensity and phase retrieval by frequency-resolved optical gating and a computational neural network"; Optics Letters, vol. 21, No. 2; Jan. 15, 1996; pp. 143-145.

David N. Fittinghoff et al.; "Measurement of the intensity and phase of ultraweak, ultrashort laser pulses"; Optics Letters, vol. 21, No. 12; Jun. 15, 1996; pp. 884-886.

T. Feurer et al.; "Measuring the temporal intensity of ultrashort laser pulses by triple correlation"; Appl. Phys. B; 1998; pp. 163-168.

Alfred Kwok et al.; "Frequency-Resolved Optical Gating Using Cascaded Second-Order Nonlinearities"; Journal of Selected Topics in Quantum Electronics, vol. 4, No. 2; Mar./Apr. 1998; pp. 271-277.

Daniel J. Kane; "Real-Time Measurement of Ultrashort Laser Pulse Using Principal Component Generalized Projection"; IEEE Journal of Selected Topics in Quantum Electronics; vol. 4, No. 2; Mar./Apr. 1998; pp. 278-284.

Scott A. Diddams et al.; "Characterizing the Nonlinear Propagation of Femtosecond Pulses in Bulk Media"; IEEE Journal of Selected Topics in Quantum Electronics, vol. 4, No. 2; Mar./Apr. 1998; pp. 306-316.

Michael J. Stimson et al.; "Noisy-light correlation functions by frequency resolved optical gating"; J. Opt. Soc. Am. B, vol. 15, No. 2; Feb. 1998; pp. 505-514.

J. W. Nicholson et al.; "Full-field characterization of femtosecond pulses by spectrum and cross-correlation measurements"; Optics Letters, vol. 24, No. 23; Dec. 1, 1999; pp. 1774-1776.

F. Romstad et al.; "Measurement of Pulse Amplitude and Phase Distortion in a Semiconductor Optical Amplifier: from Pulse Compression to Breakup"; IEEE Photonics Technology Letters, vol. 12, No. 12; Dec. 2000; pp. 1674-1676.

Tzu-Ming Liu et al.; "Triple-optical autocorrelation for direct optical pulse-shape measurement"; Applied Physics Letters, vol. 81, No. 8; Aug. 19, 2002; pp. 1402-1404.

Yoshihiro Takagi et al.; "Multiple- and single-shot autocorrelator based on two-photon conductivity in semiconductors"; Optics Letters, vol. 17, No. 9; May 1, 1992; pp. 658-660.

Thomas J. Dunn et al.; "Experimental Determination of the Dynamics of a Molecular Nuclear Wave Packet via the Spectra of Spontaneous Emission"; Physical Review Letters, vol. 70, No. 22; May 31, 1993; pp. 3388-3391.

A.N. Naumov et al.; "Frequency-time and time-space mappings for single-shot coherent four-wave mixing with chirped pulses and broad beams"; Journal of Raman Spectroscopy, 2001; pp. 960-970.

E.T.J. Nibbering et al.; "Spectral determination of the amplitude and the phase of intense ultrashort optical pulses"; J. Opt. Soc. Am. B, vol. 13, No. 2; Feb. 1996; pp. 317-329.

Victor Wong et al.; "Ultrashort-pulse characterization from dynamic spectrograms by iterative phase retrieval"; J. Opt. Soc. Am. B, vol. 14, No. 4; Apr. 1997; pp. 944-949.

Sarah M. Gallagher et al.; "Heterodyne detection of the complete electric field of femtosecond four-wave mixing signals"; J. Opt. Soc. Am. B, vol. 15, No. 8; Aug. 1998; pp. 2338-2345.

C. Dorrer et al.; "Single-shot real-time characterization of chirped-pulse amplification systems by spectral phase interferometry for direct electric-field reconstruction"; Optics Letters, vol. 24, No. 22; Nov. 15, 1999; pp. 1644-1646.

C. Dorrer; "Implementation of spectral phase interferometry for direct electric-field reconstruction with a simultaneously recorded reference interferogram"; Optics Letters, vol. 24, No. 21; Nov. 1, 1999; pp. 1532-1534.

C.Y. Chien et al.; "Single-shot chirped-pulse spectral interferometry used to measure the femtosecond ionization dynamics of air"; Optics Letters, vol. 25, No. 8; Apr. 15, 2000; pp. 578-580.

J.W. Nicholson et al.; "Unbalanced third-order correlations for full characterization of femtosecond pulses"; Optics Letters, vol. 25, No. 24; Dec. 15, 2000; pp. 1801-1803.

Sergey Yeremenko et al.; "Frequency-resolved pump-probe characterization of femtosecond infrared pulses"; Optics Letters, vol. 27, No. 13; Jul. 1, 2002; pp. 1171-1173.

J. M. Dudley, et al.; "Direct measurement of pusle distortion near the zero-disperson wavelength in an optical fiber by frequency-resolved optical gating"; Optics Letters, vol. 22, No. 7; Apr. 1, 1997; 457-459.

M.C. Chen et al.; "Freezing phase scheme for fast adaptive control and its application to characterization of femtosecond coherent optical pulses reflected from semiconductor saturable absorber mirrors"; J. Opt. Soc. Am. B, vol. 22, No. 5; May 2005; pp. 1134-1142.

I. Amat-Roldan et al.; "Measurement of electric field by interferometric spectral trace observation"; Optics Letters, vol. 30, No. 9; May 1, 2005; pp. 1063-1065.

I. Amat-Roldan et al.; "Starch-based second-harmonic-generated colinear frequency-resolved optical gating pulse characterization at the focal plane of a high-numerical-aperture lens"; Optics Letters, vol. 29, No. 19; Oct. 1, 2004; pp. 2282-2284.

Gregory D. Goodno et al.; "Ultrafast heterodyne-detected transient-grating spectroscopy using diffractive optics"; Optical Society of America, vol. 15, No. 6, Jun. 1998; pp. 1791-1794.

L. Misoguti et al.; "Generation of Broadband VUV Light Using Third-Order Cascaded Processes"; Physical Review Letters, vol. 87, No. 1, Jul. 2, 2001; pp. 013601-1-0136014.

D. Zeidler et al.; "Amplification of tailored white-light continuum"; Applied Physics, B74 (Suppl), 2002; pp. S51-S56.

T. Brixner et al.; "Generation and characterization of polarization-shaped femtosecond laser pulses"; Applied Physics B74 (Suppl), 2002; pp. S133-S144.

Jeffrey L. Krause et al.; "Creating and Detecting Shaped Rydberg Wave Packets"; Physical Review Letters, vol. 79, No. 25; Dec. 22, 1997; pp. 4978-4981.

S. Backus et al.; "16-fs, 1-µ J ultraviolet pulses generated by third-harmonic conversion in air"; Optics Letters, vol. 21, No. 9; May 1, 1996; pp. 665-667.

Julie A. Gruetzmacher et al.; "Few-cycle mid-infrared pulse generation, characterization and coherent propagation in optically dense media"; Review of Scientific Instruments, vol. 73, No. 6; Jun. 2002; pp. 2227-2236.

T. Kobayashi et al.; "Tunable visible and near-infrared pulse generator in a 5 fs regime"; Appl. Phys. B 70 (Suppl); 2000; pp. S239-S246.

A. Poppe et al; "Few-cycle optical waveform synthesis"; Applied Physics B 72; 2001; pp. 373-376.

Peifang Tian et al.; "Ultrafast measurement of two-photon absorption by loss modulation"; Optics Letters, vol. 27, No. 18; Sep. 15, 2002; pp. 1634-1636.

M. Hentschel et al.; "Generation of 0.1-TW optical pulses with a single-stage Ti:sapphire amplifier at a 1-kHz repetition rate"; Appl. Phys. B 70 [Suppl.]; 2000; pp. S161-S164.

Photogen Technologies, Inc., "Photogen-Technology"; www.photogen.com/body/tech_body.html; Dec. 20, 2001 (19 pages).

W.M. Sharman et al.; "Photodynamic therapeutics: basic principles and clinical applications"; DDT, vol. 4, No. 11; Nov. 1991; pp. 507-517.

Allison Albrecht Ferro et al.; "Complete femtosecond linear free induction decay, Fourier algorithm for dispersion relations and accuracy of the rotating wave approximation"; Journal of Chemical Physics, vol. 114, No. 10; Mar. 8, 2001; pp. 4649-4656.

J.P. Ogilvie et al.; "Fourier transform measurement of two-photon excitation spectra: applications to microscopy and optimal control"; Optics Letters, vol. 30, No. 8; Apr. 15, 2005; pp. 911-913.

D. Lalovic et al.; "Quantum mechanics in terms of non-negative smoothed Wigner functions"; Physical Review A, vol. 46, No. 3; Aug. 1, 1992; pp. 1206-1212.

Christopher J. Bardeen et al.; "Using time-dependent rate equations to describe chirped pulse excitation in condensed phases"; Chemical Physics Letters 302; 1999; pp. 405-410.

Yu-Chen Shen et al.; "What can short-pulse pump-probe spectroscopy tell us about Franck-Condon dynamics?"; Journal of Chemical Physics, vol. 110. No. 20; May 22, 1999; pp. 9793-9806.

M. Ovchinnikov et al; "Semiclassical molecular dynamics computation of spontaneous light emission in the condensed phase: Resonance Raman spectra"; Journal of Chemical Physics, vol. 114, No. 16; Apr. 22, 2001; pp. 7130-7143.

S. Yeremenko et al.; "The criterion of pulse reconstruction quality based on Wigner representation"; Applied Physics B 70 (Suppl); 2000; pp. S109-S117.

David C. Clary; "Quantum Theory of Chemical Reaction Dynamics"; Science, vol. 279, Mar. 20 1998; p. 1879.

B.D. Fainberg; "Diagram Technique for Nonlinear Optical Spectroscopy in the Fast Electronic Dephasing Limit"; Journal of the Chinese Chemical Society, 47; 2000; pp. 579-582.

Chantal Daniel et al.; "Deciphering the Reaction Dynamics Underlying Optimal Control Laser Fields"; Science Magazine, vol. 299; Jan. 24, 2003; pp. 536-539.

T. Witte et al.; "Controlling molecular ground-state dissociation by optimizing vibrational ladder climbing"; Journal of Chemical Physics, vol. 118, No. 5; Feb. 1, 2003; pp. 2021-2024.

R.J. Levis et al.; "Closing the Loop on Bond Selective Chemistry Using Tailored Strong Field Laser Pulses"; The Journal of Physical Chemistry, vol. 106, No. 27; Jul. 11, 2002; pp. 6427-6444.

Mustafa Demirplak et al.; "Optical control of molecular dynamics in a liquid"; Journal of Chemical Physics, vol. 116, No. 18; May 8, 2002; pp. 8028-8035.

M. Bergt et al.; "Time-resolved organometallic photochemistry Femtosecond fragmentation and adaptive control of CpFe(CO)2X (X=C1,Br,1)"; Journal of Organometallic Chemistry 661; 2002; pp. 199-209.

Ben R. Torralva et al; "Mechanisms for laser control of chemical reactions"; Journal of Modern Optics, vol. 49, No. 3/4; 2002; pp. 593-625.

N. H. Damrauer et al.; "Control of bond-selective photochemistry in CH2BrCl using adaptive femtosecond pulse shaping"; The European Physical Journal D, 20, 2002; pp. 71-76.

L. Windhorn et al.; "Molecular dissociation by mid-IR femtosecond pulses"; Chemical Physics Letters 357, May 3, 2002; pp. 85-90.

Robert J. Levis et al.; "Selective Bond Dissociation and Rearrangement with Optimally Tailored, Strong-Field Laser Pulses"; Science Magazine, vol. 292; Apr. 27, 2001; pp. 709-713.

T. Brixner et al.; "Problem complexity in femtosecond quantum control"; Chemical Physics 267; 2001; pp. 241-246.

O.M. Sarkisov et al.; "Control of elementary chemical reactions by femtosecond light pulses"; Quantum Electronics, vol. 31, No. 6; 2001; pp. 483-488.

Julie A. Mueller et al.; "Competing isomeric product channels in the 193 nm photodissociation of 2-chloropropene and in the unimolecular dissociation of the 2-propenyl radical"; Journal of Chemical Physics, vol. 114, No. 10; Mar. 8, 2001; pp. 4505-4521.

Chantal Daniel et al.; "Analysis and control of laser induced fragmentation processes in CpMn(CO)3"; Chemical Physics 267; 2001; pp. 247-260.

A. Glass et al.; "Control of the photodissociation of CsCl"; Applied Physics B 71; 2000; pp. 267-276.

T. Frohnmeyer et al.; "Femtosecond pump-probe photoelectron spectroscopy on Na2: a tool to study basic coherent control schemes"; Applied Physics B 71; 2000; pp. 259-266.

M. Bergt et al.; "Controlling the Femtochemistry of Fe(CO)5"; J. Phys. Chem. A, vol. 103, No. 49; 1999; pp. 10381-10387.

A. Assion et al.; "Coherent control by a single phase shaped femtosecond laser pulse"; Chemical Physics Letters 259; Sep. 13, 1996; pp. 488-494.

Langchi Zhu et al.; "Coherent Laser Control of the Product Distribution Obtained in the Photoexcitation of HI"; Science Magazine, vol. 270; Oct. 6, 1995; pp. 77-80.

Yu-hui Chiu et al.; "Vibrational mode effects, scattering dynamics and energy disposal in reaction of C2H2 with methane"; J. Chem. Phys., vol. 102, No. 3; Jan. 15, 1995; pp. 1199-1216.

J.S. Keller et al.; "Selective bond fission in methyl mercaptan at 193 nm via radial derivative coupling between the 21A" and 11A" adiabatic electronic states"; J. Chem. Phys. vol. 96, No. 6; Mar. 15, 1992; pp. 4324-4329.

I. Bar et al.; "Mode-selective bond fission: Comparison between the photodissociation of HOD (0,0,1) and HOD (1,0,0)"; J. Chem. Phys. vol. 95, No. 5; Sep. 1, 1991; pp. 3341-3346.

Michael J. Bronikowski et al.; "Bond-specific chemistry: OD:OH product ratios for the reactions H+HOD(100) and H+HOD(001)"; J. Chem. Phys., vol. 95, No. 11; Dec. 1, 1991; pp. 8647-8648.

I. Bar et al.; "Direct observation of preferential bond fission by excitation of a vibrational fundamental: Photodissociation of HOD (0,0,1)"; J. Chem. Phys., vol. 93, No. 3; Aug. 1, 1990; pp. 2146-2148.

R.L. VanderWal et al.; "Selectively breaking the O-H bond in HOD"; J. Chem. Phys., vol. 92, No. 1; Jan. 1, 1990; pp. 803-805.

Neil Shafer et al.; "Isotope effect in the photodissociation of HDO at 157.5 nm"; J. Chem. Phys., vol. 90, No. 11; Jun. 1, 1989; pp. 6807-6808.

L.J. Butler et al.; "The electronic state-selective photodissociation of CH2BrI at 248, 210 and 193 nm"; J. Chem. Phys. vol. 86, No. 4; Feb. 15, 1997; pp. 2051-2074.

L.J. Butler et al.; "Bond selective photochemistry in CH2BrI through electronic excitation at 210 nm"; J. Chem. Phys., vol. 84, No. 7; Apr. 1, 1986; pp. 4104-4106.

David J. Tannor et al.; "Control of selectivity of chemical reaction via control of wave packet evolution"; J. Chem. Phys., vol. 83, No. 10; Nov. 15, 1985; pp. 5013-5018.

Christopher J. Bardeen et al.; "Quantum Control of NaI Photodissociation Reaction Product States by Ultrafast Tailored Light Pulses"; J. Phys. Chem. A, vol. 101, No. 20; 1997; pp. 3815-3822.

V.A. Apkarian; 'Comment on "Time-resolved laser induced harpoon reactions"'; J. Chem. Phys. vol. 106, No. 12; Mar. 22, 1997; pp. 5298-5299.

R.B. Vrijen et al.; "Limitations on quantum ladder climbing in complex systems"; Physical Review A, vol. 56, No. 3; Sep. 1997; pp. 2205-2212.

Lutfur R. Khundkar et al.; "Ultrafast Molecular Reaction Dynamics in Real-Time: Progress Over a Decade"; Annu. Rev. Phys. Chem., 1990; pp. 15-60.

Stuart A. Rice; "Optical control of reactions"; Nature magazine, vol. 403; Feb. 3, 2000; pp. 496-497.

Richard N. Zare; "Laser Control of Chemical Reactions"; Science magazine, vol. 279; Mar. 20, 1998; pp. 1875-1879.

Stuart A. Rice; "Active Control of Molecular Dynamics: Coherence versus Chaos"; Journal of Statistical Physics, vol. 101, Nos. 1/2; 2000; pp. 187-212.

Herschel Rabitz et al.; "Whither the Future of Controlling Quantum Phenomena?"; Science magazine, vol. 288; May 5, 2000; pp. 824-828.

Yuri T. Mazurenko; "Spectral Holography and Spectral Nonlinear Optics of Ultrashort Pulses"; Journal of the Chinese Chemical Society, vol. 47, No. 4A; 2000; pp. 679-683.

Marcos Dantus; "Coherent Nonlinear Spectroscopy: From Femtosecond Dynamics to Control"; Annu. Rev. Phys. Chem. 2001; pp. 639-679, C1-C7.

Stuart A. Rice; "Interfering for the good of a chemical reaction"; Nature magazine; vol. 409; Jan. 18, 2001; pp. 422-426.

Wolfgang Kiefer et al.; "Femtosecond time-resolved spectroscopy of elementary molecular dynamics"; Naturwissenschaften; 2002; pp. 250-258.

Alois Renn et al.; "Multidimensional Holography by Persistent Spectral Hole Burning"; The Journal of Physical Chemistry A, vol. 106, No. 13; Apr. 4, 2002; pp. 3045-3060.

T.C. Weinacht et al.; "Using feedback for coherent control of quantum systems"; Journal of Optics B: Quantum and Semiclassical Optics; 2002; pp. R35-R52.

Niels E. Henriksen; "Laser control of chemical reactions"; Chem. Soc. Rev. 3137 42; 2002; pp. 37-42.

Stuart A. Rice et al.; "Active control of product selection in a chemical reaction: a view of the current scene"; Phys. Chem. Chem. Phys.; 2002; pp. 1683-1700.

Allen J. Bard et al.; "Holy Grails in Chemistry"; American Chemical Society, vol. 28, No. 3; Mar. 1995.

Marcos Dantus; "Ultrafast Probing and Control of Molecular Dynamics: Beyond the Pump-Probe Method"; pp. 169-188. Kuhn & Weyh SRZ Sep. 4, 2001.

Bern Kohler et al.; "Controlling the Future of Matter"; Acc. Chem. Res., vol. 28, No. 3; 1995; pp. 133-140.

M.R. Fetterman et al.; "Propagation of Complex Laser Pulses in Optically Dense Media"; The American Physical Society, Physical Review Letters, vol. 82, No. 20, May 17, 1999; pp. 3984-3987.

D. Yelin et al.; "Adaptive femtosecond pulse compression"; Optics Letters, vol. 22, No. 23, Dec. 1, 1997; pp. 1793-1795.

A.V. Sokolov; "Subfemtosecond compression of periodic laser pulses"; Optics Letters, vol. 24, No. 17, Sep. 1, 1999; pp. 1248-1250.

H.S. Eisenberg et al.; "Phase Defects in Self-Focusing of Ultrashort Pulses"; Physical Review Letters, vol. 83, No. 3, Jul. 19, 1999; pp. 540-543.

D.M. Villeneuve et al.; "Using frequency-domain manipulation of stretched femtosecond laser pulses to create fast rise and fall times on picosecond pulses"; Applied Physics B74 (Suppl), 2002; pp. S157-S161.

Dai-Sik Kim et al.; "Femtosecond-pulse distortion in quantum wells"; Appl. Phys B 74, vol. 48. No. 24; Dec. 15, 1993; pp. 17902-17905.

Anthony P. Peirce et al.; "Optimal control of quantum-mechanical systems: Existence, numerical approximation and applications"; Physical Review A, vol. 37, No. 12; Jun. 15, 1988; pp. 4950-4964.

J.M. Geremia et al.; "Incorporating physical implementation concerns into closed loop quantum control experiments"; Journal of Chemical Physics, vol. 113, No. 24; Dec. 22, 2000; pp. 10841-10848.

Thomas Hornung et al.; "Teaching optimal control theory to distill robust pulses even under experimental constraints"; Physical Review A, vol. 65; 2002; pp. 021403-1-021403-4.

Jianshu Cao et al.; "Intrapulse Dynamical Effects in Multiphoton Processes: Theoretical Analysis"; J. Phys. Chem. A; vol. 102, 1998; pp. 4284-4290.

Amichay Vardi et al.; "Laser catalysis with pulses"; Physical Review A, vol. 58, No. 2; Aug. 1998; pp. 1352-1360.

Kazuya Takasago et al.; "Evaluation of Femtosecond Pulse Shaping with Low-Loss Phase-Only Masks"; IEEE Journal of Selected Topics in Quantum Electronics, vol. 4, No. 2; Mar./Apr. 1998; pp. 346-352.

M.E. Fermann et al.; "Shaping of ultrashort optical pulses by using an integrated acousto-optic tunable filter"; Optics Letters, vol. 18, No. 18; Sep. 15, 1993; pp. 1505-1507.

V.L. da Silva et al.; "Nonlinear pulse shaping and causality"; Optics Letters, vol. 18, No. 8; Apr. 15, 1993; pp. 580-582.

E. Zeek et al.; "Adaptive pulse compression for transform-limited 15-fs high-energy pulse generation"; Optics Letters, vol. 25, No. 8; Apr. 15, 2000; pp. 587-589.

A. Apolonski et al.; "Controlling the Phase Evolution of Few-Cycle Light Pulses"; Physical Review Letters, vol. 85, No. 4; Jul. 24, 2000; pp. 740-743.

Christophe Dorrer et al.; "Phase Amplitude Coupling in Spectral Phase Modulation"; IEEE Journal of Selected Topics in Quantum Electronics, vol. 4, No. 2; Mar./Apr. 1998; pp. 342-345.

David J. Jones et al.; "Carrier-Envelope Phase Control of Femtosecond Mode-Locked Lasers and Direct Optical Frequency Synthesis"; Science magazine, vol. 288; Apr. 28, 2000; pp. 635-639.

Vladimir Kalosha et al.; "Generation of Single Dispersion Precompensated 1-fs Pulses by Shaped-Pulse Optimized High-Order Stimulated Raman Scattering"; Physical Review Letters, vol. 88, No. 10; Mar. 11, 2002; pp. 103901-1-13901-4.

Donna Strickland et al.; "Compression of Amplified Chirped Optical Pulses"; Optics Communications; vol. 55, No. 6; Oct. 15 1985; pp. 447-449.

H. Wang et al.; "Abstract-20-fs pulse shaping with a 512-element phase-only liquid crystal modulator"; IEEE Journal of Selected Topics in Quantum Electronics; 7 (4): 718-727; Jul./Aug. 2001 (1 page).

L. Xu et al.; "Abstract-Programmable chirp compensation for 6-fs pulse generation with a prism-pair-formed pulse shaper"; IEEE Journal of Quantum Electronics; 36 (8): 893-899; Aug. 2000 (1 page).

CVI Laser Corporation; "TNM-2 Negative Group Velocity Dispersion Mirrors"; www.cvilaser.com/ultra-fast; Jan. 13, 2002 (2 pages).

H. Takada et al.; "Large-ratio stretch and recompression of sub-10-fs pulses utilizing dispersion managed devices and a spatial light modulator"; Appl. Phys. B 74 [Suppl.]; 2002; pp. S253-S257.

N. Karasawa et al.; "Optical pulse compression to 5.0 fs by by use only a spatial light modulator for phase compensation"; J. Opt. Soc. Am. B, vol. 18, No. 11; Nov. 2001; pp. 1742-1746.

C.P.J. Barty et al.; "Generation of 18-fs, multiiterawatt pulses by regenerative pulse shaping and chirped-pulse amplification"; Optics Letters, vol. 21, No. 9; May 1, 1996; pp. 668-670.

Marcos Dantus; GeneticAlgorithm-v4.nb to simulate an adaptive genetic algorithm;Oct. 2001; pp. 1-7.

M. Hacker et al.; "Iterative Fourier transform algorithm for phase-only pulse shaping"; Optics Express, vol. 9, No. 4, Aug. 13, 2001; pp. 191-199.

T. Brixner et al.; "Feedback-controlled optimization of amplified femtosecond laser pulses"; Applied Physics B 68; 1999; pp. 281-284.

A. Efimov et al.; "Minimization of dispersion in an ultrafast chirped pulse amplifier using adaptive learning"; Appl. Phys. B 70 (Suppl); 2000; pp. S133-S141.

D. Zeidler et al.; "Evolutionary algorithms and their application to optimal control studies"; Physical Review A, vol. 64; 2001; pp. 023420-1-023420-13.

C. Rangan et al.; "Optimally shaped terahertz pulses for phase retrieval in a Rydberg-atom data register"; Physical Review A, vol. 64; 2001; pp. 033417-1-033417-5.

T. Tanabe et al.; "Compensation for a Transfer Function of a Regenerative Amplifier to Generate Accurately Shaped Ultrashort Pulses in Both the Amplitude and Phase"; IEE J. of Selected Topics in QUantum Elecronics, vol. 10, No. 1; Jan./Feb. 2004; pp. 221-228.

Hosseini, S. Abbas et al.; "Coherent control of multiphoton transitions with femtosecond pulse shaping"; Physical Review A; pp. 033410-1-033410-7.

Yan, Y.J. et al.; "Electronic dephasing, vibrational relaxation, and solvent friction in molecular nonlinear optical line shapes"; J. Chems. Phys.; Oct. 15, 1988; pp. 5160-5176.

Meshulach, M. et al.; "Coherent quantum control of multiphoton transitions by shaped ultrashort optical pulses" Phys. Rev. A 60; 1999; pp. 1287-1292.

Weinacht, T.C. et al.; "Controlling the shape of a quantum wavefunction"; Nature, vol. 397; Jan. 1999; pp. 233-235.

Buist, A.H. et al.; "Probing microscopic chemical environments with high-intensity chirped pulses"; Optics Letters 24; 1999; pp. 244-246.

Broers, B. et al.; "Large interference effects of small chirp observed in two-photon absorbtion"; Opt. Commun. 91; 1992; p. 57-61.

Broers, B. et al.; "Diffraction and focusing of spectral energy in multiphoton processes"; Phys Rev. A 46; 1992; p. 2749-2756.

Walowicz, K.A. et al.; "Multiphoton Intrapulse Interference 1: Control of Multiphoton Processes in Condensed Phases"; J. Phys. Chem A 106 (41); Oct. 17, 2002; pp. 9369-9373.

Zheng, Z. et al.; "Coherent control of second harmonic generation using spectrally phase coded femtosecond waveforms"; Chem. Phys. 267; 2001; pp. 161-171.

Clara et al.; "Femtoscond laser mass spectroscopy of ferrocenes: Photochemical stabilization by bridged cyclopentadienyl rings?"; International Journal of Mass Spectrometry, Elsevier Science Publishers, vol. 203, No. 1-3; Dec. 26, 2000; pp. 71-81.

Bucksbaum, Philip; "An atomic dimmer switch"; Nature; Nov. 19, 1998; vol. 396; pp. 217-219.

Dela Cruz, J.M. et al.; "Multiphoton Intrapulse Interference 3: Probing Microscopic Chemical Environments"; J. Phys. Chem. A 2004, 108; pp. 53-58.

Goswami, D.; "Optical pulse shaping approaches to coherent control"; Physics Reports 374; 2004; pp. 385-481.

Leibfried, D. et al.; "Quantum information with trapped ions at NIST"; Journal of Modern Optics; vol. 50, No. 6/7; Apr.-May 2003; pp. 1115-1129.

Lozovoy, V.V.; "Multiphoton intrapulse interference. II. Control of two- and three-photon laser induced fluorescence with shaped pulses"; J. Chem. Phys. 118 (7); Feb. 15, 2005; pp. 3187-3196.

Roy, I. et al; "Ceramic-based nanoparticles entrapping water-soluble photosensitizing drugs: A novel drug carrier system for photodynamic therapy"; J. Am. Chem. Soc. 125; 2003; pp. 7860-7865.

VandenBout, D.A. et al.; "Discrete intensity jumps and intramolecular electronic energy transfer in the spectroscopy of single conjugated polymer molecules"; Science 277; 1997; pp. 1074-1077.

Paye, J.; "How to Measure the Amplitude and Phase of an Ultrashort Light Pulse with an Autocorrelator and a Spectrometer"; IEEE Journal of Quantum Electronics, vol. 30, No. 11; Nov. 1994; pp. 2693-2697.

Kovtoun et al.; "Mass-Correlated Pulsed Extraction: Theoretical Analysis and Implementation With a Linear matrix-Assisted laser Desorption/Ionization Time of Flight Mass Spectrometer"; Journal of the American Society for Mass Spectrometry, Elsevier Science Inc; vol. 11, No. 10; Oct. 2000; pp. 841-853.

Cumpston, B.H. et al.; "New Photopolymers based on Two-Photon Absorbing Chromophores and Application to Three-Dimensional Microfabricaton and Optical Storage"; Mat. Res. Soc. Symp. Proc; vol. 488; 1998; pp. 217-225.

Cumpston,B.H. et al.; "Two-photon polymerization initiators for three-dimensional optical data storage and microfabrication"; Letters to Nature; vol. 398; Mar. 4, 1999; pp. 51-54.

Lu, Y.M. et al.; "Highly sensitive two-photon chromophores applied to three dimensional lithographic microfabrication: design, synthesis and characterization towards two-photon absorbtion cross section"; J. Mater Chem. 14(1); 2004; pp. 75-80.

Postnikova, B.J. et al.; "Towards nanoscale three-dimensional fabrication using two-photon initiated polymerization and near-field excitation"; Microelectron. Eng. 69 (2-4); Sep. 2003; pp. 459-465.

Sun, H.B. et al.; "Two-photon laser precision microfabrication and its applications to micronano devices and systems"; J. Lightwave Technol. 21(3); Mar. 2003; pp. 624-633.

Mitra et al.; "Nonlinear Limits to the Information Capacity of Optical Fibre Communications"; Nature; vol. 411; Jun. 28, 2001; pp. 1027-1030.

Brattke, S. et al.; "Generation of Photon Number States on Demand via Cavity Quantum Electrodynamics"; Phys. Rev. Lett.; vol. 86; Apr. 16, 2001; pp. 3534-3537.

Goswami, D.; "Ultrafast Pulse Shaping Approaches to Quantum Computing"; Indian Institute of Technology; Dec. 24, 2003 (8 pages).

Xu, C. et al.;"Two photon optical beam induced current imaging throughout backside of integrated circuits"; Appl. Phys. Lett. 71; 1997; pp. 2578-2580.

Yang, W. et al.; "High-ratio Electro-optical Data Compression for Massive Accessing Networks Using AOM-based Ultrafast Pulse Shaping"; Journal of Optical Communications; vol. 22, No. 1; 2001; pp. 694-697.

Kane, Daniel J. et al.; "Single-shot measurement of the intensity and phase of an arbitrary ultrashort pulse by using frequency-resolved optical gating"; Optics Letters, vol. 18, No. 10; May 15, 1993; pp. 823-825.

Kane, Daniel J. et al.; "Single-shot measurement of the intensity and phase of a femtosecond UV laser pulse with frequency-resolved optical gating"; Optics Letters, vol. 19, No. 14; Jul. 15, 1994; pp. 1061-1063.

Clement, Tracy Sharp et al.; "Single-Shot measurement of the amplitude and phase of ultrashort laser pulses in the violet"; Optics Letters, vol. 20, No. 1; Jan. 1, 1995; pp. 70-72.

Kohler, Bern et al.; "Phase and intensity characterization of femtosecond pulses from a chirped-pulse amplifier by frequency-resolved optical gating"; Optics Letters, vol. 20, No. 5; Mar. 1, 1995; pp. 483-485.

Sweetser, John N. et al.; "Transient-grating frequency-resolved optical gating"; Optics Letters, vol. 22, No. 8; Apr. 15, 1997; pp. 519-521.

Trebino, Rick et al.; "Measuring ultrashort laser pulses in the time-frequency domain using frequency-resolved optical gating"; Rev. Sci. Instrum. 68 (9); Sep. 1997; pp. 3277-3295.

Dudley, John M. et al.; "Complete Characterization of Ultrashort Pulse Sources at 1550 nm"; IEEE Journal of Quantum Electronics, vol. 35, No. 4; Apr. 1999; pp. 441-450.

Trebino, Rick et al.; "The Dilemma of Ultrashort-Laser-Pulse Intensity and Phase Measurement and Applications"; IEEE Journal of Quantum Electronics, vol. 35, No. 4; Apr. 1999; pp. 418-420.

Cormack, I.G. et al.; "Practical measurement of femtosecond optical pulses using time-resolved optical gating"; Optics Communications 194; Jul. 15, 2001; pp. 415-424.

Chu, K.C. et al.; "Direct measurement of the spectral phase of femtosecond pulses"; Optics Letters, vol. 20, No. 8; Apr. 15, 1995; pp. 904-906.

Sullivan, A. et al.; "Quantitative investigation of optical phase-measuring techniques for ultrashort pulse lasers"; J. Opt. Soc. Am. B, vol. 13, No. 9; Sep. 1996; pp. 1965-1978.

Baltuska, Andrius et al.; "Amplitude and phase characterization of 4.5-fs pulses by frequency-resolved optical gating"; Optics Letters, vol. 23, No. 18; Sep. 15, 1998; pp. 1474-1476.

Gallmann, L. et al.; "Techniques for the characterization of sub-10-fs optical pulses: a comparision"; Appl. Phys. B 70 (Suppl): 2000; pp. S67-S75.

Anderson, M.E. et al.; "The effects of noise on ultrashort-optical-pulse measurement using SPIDER"; Appl. Phys. B 70 (Suppl); 2000; pp. S85-S93.

Nicholson, J.W. et al; "Noise sensitivity and accuracy of femtosecond pulse retrieval by phase and intensity from correlation and spectrum only (PICASO)"; J. Opt. Soc. Am. B; vol. 19, No. 2; Feb. 2002; pp. 330-339.

Dorrer, Christophe et al.; "Precision and consistency criteria in spectral phase interferometry for direct electric-field reconstruction"; J. Opt. Soc. Am. B, vol. 19, No. 5; May 2002; pp. 1030-1038.

Walmsley, Ian A. et al.; "Characterization of the electric field of ultrashort optical pulses"; J. Opt. Soc. Am. B., vol. 13, No. 11; Nov. 1996; pp. 2453-2463.

Lange, H. Rudiger et al.; "Reconstruction of the Time Profile of Femtosecond Laser Pulses through Cross-Phase Modulation"; IEEE Journal of Selected Topics in Quantum Electronics, vol. 4, No. 2; Mar./Apr. 1998; pp. 295-300.

Iaconis, C. et al.; "Direct Interferometric Techniques for Characterizing Ultrashort Optical Pulses"; IEEE Journal of Selected Topics in Quantum Electronics, vol. 4, No. 2; Mar./Apr. 1998; pp. 285-294.

Iaconis, C. et al.; "Spectral phase interferometry for direct electric-field reconstruction of ultrashort optical pulses"; Optics Letters, vol. 23, No. 10, May 15, 1998; pp. 792-794.

Dietrich, P. et al.; "Determining the absolute carrier phase of a few-cycle laser pulse"; Optics Letters, vol. 25, No. 1, Jan. 1, 2000; pp. 16-18.

Reid, D.T. et al.; "Amplitude and phase measurement of mid-infrared femtosecond pulses by using cross-correlation frequency-resolved optical gating"; Optics Letters, vol. 25, No. 19, Oct. 1, 2000; pp. 1478-1480.

Michelmann, K. et al.; "Measurement of the Page function of an ultrashort laser pulse"; Optics Communications; Oct. 15, 2001, pp. 163-170.

Gallmann, L. et al.; "Spatially resolved amplitude and phase characterization of femtosecond optical pulses"; Optics Letters, vol. 26, No. 2; Jan. 15, 2001; pp. 96-98.

Kakehata, Masayuki et al.; "Single-shot measurement of carrier-envelope phase changes by spectral interferometry"; Optics Letters, vol. 26, No. 18; Sep. 15, 2001; pp. 1436-1438.

Geindre, J.P. et al.; "Single-shot spectral interferometry with chirped pulses"; Optics Letters, vol. 26, No. 20; Oct. 15, 2001; pp. 1612-1614.

Dorrer, C. et al.; "Direct space-time characterization of the electric fields of ultrashort optical pulses"; Optics Letters, vol. 27, No. 7; Apr. 1, 2002; pp. 548-550.

Trebino, R. et al; "Measuring Ultrashort Laser Pulses Just Got a Lot Easier!"; Optics & Photonics News; Jun. 2001; pp. 22-25.

Zheng, Z. et al. "Spectral phase correlation of coded femtosecond pulses by second-harmonic generation in thick nonlinear crystals"; Opt. Lett. 25; 2000; pp. 984-986.

Spielmann, C. et al.; "Ultrabroadband Femtosecond Lasers"; IEEE Journal of Quantum Electronics; vol. 30, No. 4; Apr. 1994; pp. 1100-1114.

Yelin, D. et al.; "Laser scanning third-harmonic-generation microscopy in biology"; Optics Express; vol. 5, No. 8; Oct. 11, 1999; pp. 169-175.

Zipfel, W.R. et al; "Nonlinear magic: multiphoton microscopy in the biosciences"; Natire Biotechnology, 121 (11); Nov. 2003; pp. 1369-1377.

Larson, D.R. et al.; "Water soluble quantum dots for multiphoton imaging in vivo"; Science 300: May 30, 2003; pp. 1434-1436.

Osborn, D.L. et al.; "Spectral and intensity dependence of spatially resolved two-photon conductivity defects on a GaAsP photodiode"; J. Appl. Phys 89; 2001; pp. 626-633.

Pastirk, I. et al; "Selective two-photon microscopy with shaped femtosecond pulses"; Opt. Express 11; 2003; pp. 1695-1701.

Drexler W. et al.; "In vivo ultrahigh-resolution optical coherence tomography"; Optics Letters, vol. 24, No. 17; Sep. 1, 1999; pp. 1221-1223.

Hasan, T. et al.; "Photodynamic Therapy of Cancer"; Chapter 40 in Holland Frei Cancer Medicine; BC Dekker Inc.; 2003; (55 pages).

Sharman, W.M. et al.: "Targeted photodynamic therapy via receptor mediated delivery systems"; Adv. Drug Delivery Rev. 56(1); Jan. 2004; pp. 53-76.

Assion, A. et al; "Control of Chemical Reactions by Feedback-Optimized Phase-Shaped Femtosecond Laser Pulses"; Science Magazine, vol. 282; Oct. 30, 1998; pp. 919-922.

Warren, W.S.; "Chemistry with photons"; Science, vol. 262; Nov. 12, 1993; pp. 1008-1009.

Chilla, Juan L.A. et al.; "Direct determination of the amplitude and the phase of femtosecond light pulses"; Optics Letters; vol. 16, No. 1; Jan. 1, 1991; pp. 39-41.

Kim, D.S. et al; "Femtosecond pulse distortion in GaAs quantum wells and its effect on pump-probe or four-wave-mixing experiments"; Physical Review B; vol. 50, No. 24; Dec. 15, 1994; pp. 18240-18249.

Kaindl, Robert A. et al.; "Generation, shaping, and characterization of intense femtosecond pulses tunable from 3 to 20 μm"; J. Opt. Soc. Am. B; vol. 17, No. 12; Dec. 2000; pp. 2085-2094.

Panasenko, Dmitriy et al.; "Single-shot sonogram generation for femtosecond laser pulse diagnostics by use of two-photon absorbtion in a silicon CCD camera"; Optics Letters; vol. 27, No. 16; Aug. 15, 2002; pp. 1475-1477.

Baltuska, Andrius et al.; "Visible pulse compression to 4 fs by optical parametric amplification and programmable dispersion control"; Optics Letters; vol. 27, No. 5; Mar. 1, 2002; pp. 306-308.

Meshulach D. et al.; "Adaptive ultrashort pulse compression and shaping"; Optics Communications 138; 1997; pp. 345-348.

Brixner, T. et al.; "Feedback-controlled femtosecond pulse shaping"; Appl. Phys. B 70 (Suppl); 2000; pp. S119-S124.

Stobrawa, G. et al.; "A new high-resolution femtosecond pulse shaper"; Appl. Phys. B 72; 2001; pp. 627-630.

Hacker, M. et al.; "Frequency doubling of phase-modulated, ultrashort laser pulses"; Appl. Phys. B 73; 2001; pp. 273-277.

Weiner, Andrew M. et al.; "Femtosecond Pulse Shaping for Synthesis, Processing and Time-to-Space Conversion of Ultrafast Optical Waveforms"; IEEE Journal of Selected Topics in Quantum Electronics; vol. 4, No. 2; Mar./Apr. 1998; pp. 317-331.

Dudovich, N. et al; "Transform-limited pulses are not optimal for resonant multiphoton transitions"; Phys. Rev. Lett. 86; 2001; pp. 47-50.

Hillegas, C.W. et al.; "Femtosecond laser pulse shaping by use of microsecond radio-frequency pulses"; Optics Letters; vol. 19, No. 10; May 15, 1994; pp. 737-739.

Weiner, A.M. et al.; "Programmable Shaping of Femtosecond Optical Pulses by Use of 128-Element Liquid Crystal Phase Modulator"; IEEE Journal of Quantum Electronics; vol. 28, No. 4; Apr. 1992; pp. 908-920.

Matuschek. N.; "Back-side-coated chirped mirrors with ultra-smooth broadband dispersion characteristics"; Applied Physics B 71; Sep. 6, 2000; pp. 509-522.

Ding. Y.; "Femtosecond pulse shaping by dynamic holograms in photorefractive multiple quantum wells"; Optics Letters; vol. 22, No. 10; May 15, 1997; pp. 718-720.

Imeshev, G. et al. "Engineeable femtosecond pulse shaping by second-harmonic generation with Fourier synthetic quasi-phase-matching gratings"; Optics Letters; vol. 23, No. 11; Jun. 1, 1998; pp. 864-866.

Tull, J.X. et al.; "High-Resolution, Ultrafast Laser Pulse Shaping and Its Applications"; Advances in Magnetic and Optical Resonance; vol. 20; 1997; pp. 1-65.

Weiner, A.M.; "Femtosecond pulse shaping using spatial light modulators"; Rev. Sci. Instrum. vol. 71(5); 2000; pp. 1929-1960.

Schreier, F. et al.; "Femtosecond pulse shaping with a stratified diffractive structure"; Optics Communications 185; 2000; pp. 227-231.

Bhattacharya, N. et al.; "Implementation of Quantum Search Algorithm using Classical Fourier Optics"; Phys. Rev. Lett.; vol. 88. No. 13; Apr. 1, 2002; p. 137901-1-137901-4.

Baumert, T. et al. "Femtosecond pulse shaping by an evolutionary algorithm with feedback"; Appl. Phys. B 65; 1997; pp. 779-782.

Hornung, Thomas et al.; "Adapting optimum control theory and using learning loops to provide experimentally feasible shaping mask patterns"; Journal of Chemical Physics; vol. 115, No. 7; Aug. 15, 2001; pp. 3105-3111.
Meshulach, D. et al.; "Adaptive real-time femtosecond pulse shaping"; J. Opt. Soc. Am. B; vol. 15, No. 5; May 1998; pp. 1615-1619.
Zeidler, D. et al.; "Adaptive compression of tunable pulses from a non-colinear-type OPA to below 16 fs by feedback-controlled pulse shaping"; Appl. Phys. B 70 (Suppl); 2000; pp. S125-S131.
Comstock et al.; "Multiphoton intrapulse interference 6; binary phase shaping"; Optics Express Opt. Soc. America USA, vol. 12, No. 6, Mar. 22, 2004; pp. 1061-1066.
Hu et al.; "A New Nonlinear Optical Crystal-BaAlBO3F2(BABF)"; Japanese Journal of Applied Physics, vol. 41, No. 10B, Part 2, Oct. 15, 2002; pp. L1131-L1133.
Weiner et al.; "Shaping of femtosecond pulses using phase-only filters designed by simulated annealing"; Journal of the Optical Society of America A (Optics and Image Science) USA, vol. 10, No. 5, May 1993; pp. 1112-1120.
M. Dantus et al., "Experimental Coherent Laser Control of Physicochemical Processes", Chem. Rev. 2004, 104, pp. 1813-1859.
Dela Cruz, J. et al., "Use of coherent control methods through scattering biological tissue to achieve functional imaging," PNAS, vol. 101, No. 49, Dec. 7, 2004, pp. 16996-17001.
Weiner, A.M. et al. "Generation of terahertz-rate trains of femtosecond pulses by phase-only filtering," Optics Letters, vol. 15, No. 1, Jan. 1, 1990, pp. 51-53.
M. Hacker et al., "Iterative Fourier Transform Algorithm for Phase-Only Pulse Shaping", Optics Express, vol. 9, No. 4, Aug. 13, 2001, pp. 191-199.
R. Bartels et al., "Shaped-Pulse Optimization of Coherent Emission of High-Harmonic Soft X-Rays", 2000 Macmillan Magazines Ltd., Nature, vol. 406. Jul. 13, 2000, pp. 164-166.
H. Zou, C. Zhou, Femtosecond Pulse Shaping with Space-to-Time Conversion Based on Planar Optics, Optik Optics, ScienceDirect, 2006/2007, pp. 5-8.
S. Zhang, X. Zhang, J. Huang, L. Deng, Z. Sun, W. Zhang, Z. Wang, Z. Xu, R.Li, Coherent Enhancement of Broadband Frequency Up-Conversion in BBO Crystal by Shaping Femtosecond Laser Pulses, Optics Communications, ScienceDirect, 2006/2007, pp. 559-563.
Y. Oishi, A. Suda, F. Kannari, K. Midorikawa, Intense Femtosecond Pulse Shaping Using a Fused-Silica Spatial Light Modulator, Optics Communications, ScienceDirect, 2006/2007, pp. 305-309.
B. Xu, Y. Coello, V.Lozovoy, D. Harris; M. Dantus, Pulse Shaping of Octave Spanning Femtosecond Laser Pulses, Optics Express, vol. 14, No. 22, Oct. 30, 2006, six pages.
F.M. Reinert, M. Ninck, W. Lüthy, T. Feurer, Shaping a Femtosecond Pulse with a Programmable Thermo-Optically Driven Phase Modulator, Optics Express, vol. 15, No. 7, Apr. 2, 2007, six pages.
H. Miao, A. Weiner, C. Langrock, R. Roussev, M. Fejer, Sensing and Compensation of Femtosecond Waveform Distortion Induced by All-Order Polarization Mode Dispersion at Selected Polarization States, Optics Letters, vol. 32, No. 4, Feb. 15, 2007, pp. 424-426.
S. Nath, D. Urbanek, S. Kern, M. Berg, High-Resolution Raman Spectra with Femtosecond Pulses: An Example of Combined Time- and Frequency-Domain Spectroscopy, Physical Review Letters, 2006, pp. 267401-1 to 267401-4.
Feurer, T., et al.; "Coherent Control Over Collective Polariton Excitations: The Dawn of Polaritonics;" 2002 Thirteenth International Conference on Ultrafast Phenomena, Technical Digest (Tops vol. 72); Opt. Soc. America; XP008086358; pp. 541-545.
Sato, Masamichi, et al.; "Adaptive Pulse Shaping of Femtosecond Laser Pulses in Amplitude and Phase Through a Single-Mode Fiber by Referring to Frequency-Resolved Optical Gating Patterns;" Jpn. J. Appl. Phys., vol. 41 (2002); Part 1 No. 6A, Jun. 2002; XP-002436366; pp. 3704-3709.
Gee, S., et al.; "Ultrashort Pulse Generation by Intracavity Spectral Shaping and Phase Compensation of External-Cavity Modelocked Semiconductor Lasers;" IEEE Journal of Quantum Electronics, vol. 36, No. 9, Sep. 2000; XP-002462407; pp. 1035-1040.
Scaffidi, J., et al.; "Spatial and Temporal Dependence of Interspark Interactions in Femtosecond-Nanosecond Dual-Pulse Laser-Induced Breakdown Spectroscopy;" Applied Optics, vol. 43, No. 27, Sep. 20, 2004; XP-002462408; pp. 5243-5250.
Pfeiffer, W., et al.; "Ultrafast Spatio-Temporal Near-Field Control;" IEEE 2005 European Quantum Electronics Conference, 0-7803-8973-5/05; p. 169 (1 page).
Kroner, D. et al.; "Asymmetric Laser Excitation in Chiral Molecules: Quantum Simulations for a Proposed Experiment, Chemical Physics Letters;" Elsevier Netherland, vol. 372, No. 1-2, Apr. 22, 2003, pp. 242-248.
Hoki, K. et al.; "Locally Designed Pulse Shaping for Selective Preparation of Enantiomers fromtheir Racemate;" Journal of Chemical Physics, New York, NY, US, vol. 114, No. 4, Jan. 22, 2001, pp. 1575-1581.
Bychkov S. S. et al.; "Laser Synthesis of Chiral Molecules in Isotropic Racemic Media;" Journal of Experimental and Theoretical Physics, Nauka/Interperiodica, MO, vol. 93, No. 1, Jul. 1, 2001, pp. 24-32.
Hoki, K. et al.; "Selective Preparation of Enantiometers from a Racemate by Laser Pulses: Model Simulation for Oriented Atropisomers with Coupled Rotations and Torsions;" Chemical Physics Elsevier Netherlands, vol. 267, No. 1-3, Jun. 1, 2001, pp. 59-79.
Brixner T., et al.; "Quantum Control by Ultrafast Polarization Shaping;" Phys Rev Lett., vol. 92, No. 20, May 21, 2004, pp. 208301-1.
Thanopulos I. et al.; Laser-Driven Coherent Manipulation of Molecular Chirality, Chemical Physics Letters Elsevier Netherlands, vol. 390, No. 1-3, May 21, 2004, pp. 228-235.
Atabek, O., et al.; Intense Laser Control of the Chemical Bond, Theochem Elsevier Netherlands, vol. 493, Dec. 15, 1999, pp. 89-101.
Pelfang Tian et al.; "Femtosecond Phase-Coherent Two-Dimensional Spectroscopy;" Science American Assoc. Adv. Sci. USA, vol. 300, No. 5625, Jun. 6, 2003, pp. 1553-1555.
Motzkus, M.; "Open and Loop Control of Complex Molecules with Shaped fs Pulses;" 2003 International Conference Physics and Control, Proceedings (Cat. No. 03EX708), IEEE Piscataway, NJ, USA, vol. 3, 2003, p. 746.
Ma R., et al.; "Intense Femtosecond Laser Field-Induced Coulomb Fragmentation of C2H4;" International Journal of Mass Spectrometry, Elsevier, Amsterdam, NL, vol. 242, No. 1, Mar. 15, 2005, pp. 43-48.
Wu, C. et al.; "Mass and Photoelectron Spectrometer for Studying Field-Induced Ionization of Molecules;" International Journal of Mass Spectrometry, Elsevier Science Publishers, Amsterdam, NL, vol. 216, No. 3, May 15, 2002, pp. 249-255.
Chen, Jr. et al.; "Femtosecond Laser-Induced Dissociative Ionization and Coulomb Explosion of Ethanol;"International Journal of Mass Spectrometry, Elsevier, Amsterdam, NL, vol. 241, No. 1, Feb. 15, 2005, pp. 25-29.
Wu, Chengyin et al.; "Laser-Induced Dissociation and Explosion of Methane and Methanol;" J. Phys. B. At. Mol. Opt. Phys; Journal of Physics B: Atomic, Molecular and Optical Physics, Jun. 14, 2002, vol. 35, No. 11, pp. 2575-2582.
Tomizawa H. et al.; "Development of Automatically Optimizing System of Both Spatial and Temporal Beam Shaping for UV-Laser Pulse;" Proceedings of the SPIE—The International Society for Optical Engineering SPIE—Int. Soc. Opt. Eng USA, vol. 5481, No. 1, 2004, pp. 47-55.
Yu, Huang et al.; "Application of Adaptive Feedback Loop for Ultra-Violet Femtosecond Pulse Shaper Control;" Optics Express Opt. Soc. America USA, vol. 14, No. 21, Oct. 2006.
Roth, M. et al.; "Acousto-Optic Femtosecond Pulse Shaping in the Ultraviolet, Lasers and Electro-Optics;" (Cleo). Conference in Baltimore, MD, USA, Piscataway, NJ, USA, IEEE, May 22-27, 2005, pp. 2244-2246.
Roth, M. et al.; "Acousto-Optical Shaping of Ultraviolet Femtosecond Pulses;" Applied Physics B; Lasers and Optics, Springer-Verlag, BE, vol. 80, No. 4-5, Apr. 1, 2005, pp. 441-444.
Brixner, T., A. Oehrlein, M. Strehle, and G. Gerber "Feedback-controlled femtosecond pulse shaping" Applied Physics B 70 [Suppl.], S119-S124 (2000).

O'Shea, Patrick, Mark Kimmel, Xun Gu, and Rick Trebino "Highly simplified device for ultrashort-pulse measurement" Optics Letter/ vol. 26, No. 12 / Jun. 15, 2001.

Zheng, Z. and A.M. Wolfe "Coherent control of second harmonic generation using spectrally phase coded femtosecond waveforms" Chemical Physics 267 (2001) 161-171 (Received Aug. 31, 2000).

Zeek, E. et al., "Pulse Compression by Use of Deformable Mirrors," Optics Letters, OSA, Optical Society of America, vol. 24, No. 7, Apr. 1, 1999, pp. 493-495.

Sardesai, H et al. "A Femtosecond Code-Division Multiple-Access Communication System Test Bed," Journal of Lightwave Technology, IEEE Service Center, vol. 16, No. 11, Nov. 1, 1998, p. 1953-1964.

Foing, J.P. et al. "Femtosecond Pulse Phase Measurement by Spectrally Resolved Up-Conversion—Application to Continuum Compression," IEEE J. Quantum Electron. 28, 2285 (1992).

Rhee, T.K. et al. "Chirped-Pulse Amplification of 85-Fs Pulses at 250 Khz with 3rd-Order Dispersion Compensation by Use of Holographic Transmission Gratings," Opt. Lett. 19, 1550 (1994).

Albrecht, T.F. et al. "Chirp Measurement of Large-Bandwidth Femtosecond Optical Pulses Using 2-Photon Absorption," Opt. Commun. 84, 223 (1991).

Ranka et al., "Autocorrelation Measurement of 6-fs Pulses Based on the Two-Photon-induced Photocurrent in a GaAsP Photodiode," Opt. Lett. 22 (17), 1344-1346 (1977).

Rivet, S. et al., "Complete pulse characterization: measurements of linear and nonlinear properties" Opt. Commun. 181, 425-435 (2000).

Weiner, A.M. "Ultrafast Optics" Chapter 3 entitled "Ultrafast-Pulse Measurement Methods" (pp. 85-146), (2009).

Dantus, Marcos et al. "Two-photon microscopy with Sub-8fs laswer pulse" PDPA Frontiers in Optics/Laser Science XXVI; Oct. 24-28, 2010, pp. 1-18.

Eramo, R. et al. "Third-harmonic generation in positively dispersive gases with a novel cell", vol. 33, No. 9, Applied Optics, Mar. 20, 1994, pp. 1691-1696.

* cited by examiner

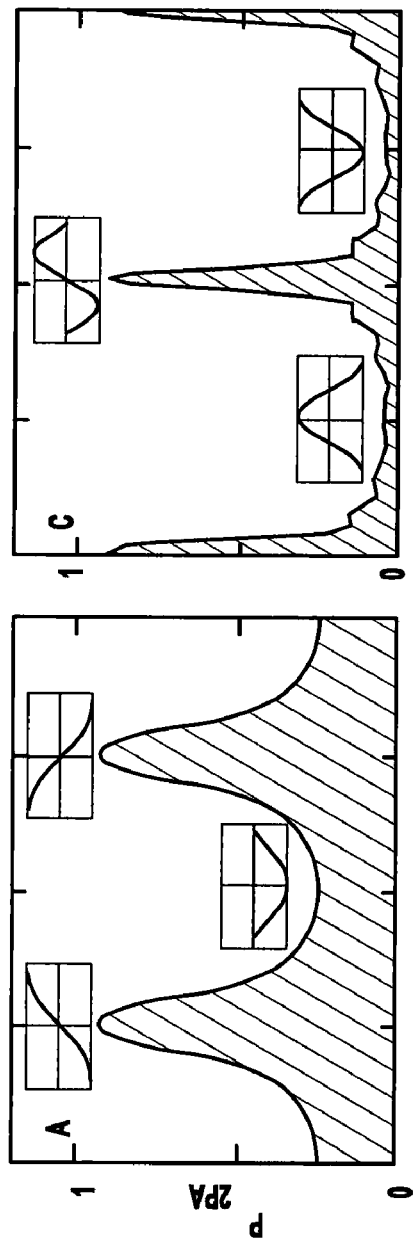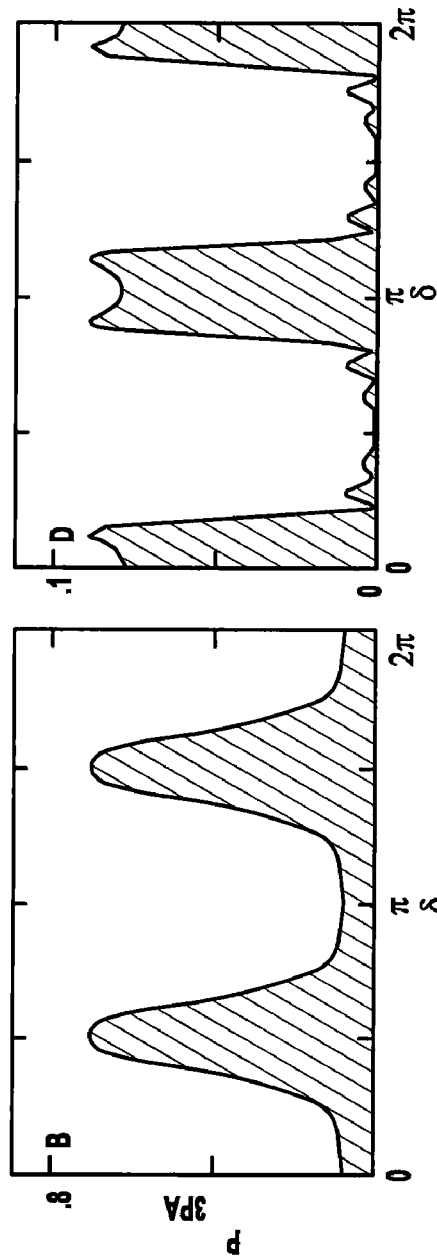
Figure - 3A
Figure - 3B
Figure - 3C
Figure - 3D

☐ one vs. ▨ multiphoton

>1000 : 1                    1 : 0.6

▨ two vs. ▨ multiphoton

>1000 : 1                    1 : 4

▨ two vs. ▨ three photon 1.4 : 1                      1 : 2.2

LASER PULSE SHAPING SYSTEM

CROSS REFERENCE TO RELATED APPLICATIONS

This application is a divisional of U.S. patent application Ser. No. 10/265,211, filed Oct. 4, 2002, U.S. Pat. No. 7,450,618, which is a continuation-in-part of PCT/US02/02548, filed Jan. 28, 2002, claiming priority to U.S. provisional application Ser. No. 60/265,133, filed Jan. 30, 2001, which are all incorporated by reference herein.

BACKGROUND AND SUMMARY OF THE INVENTION

The present invention generally relates to a laser system and more particularly to a laser system using ultrashort laser pulses with phase modulation.

Commercially practical femtosecond lasers have been unavailable until recently. For example, lasers which can generate 10 femtosecond or less laser pulse durations have traditionally been extremely expensive, required unrealistically high electrical energy consumption (for extensive cooling, by way of example) and depended on laser dyes that had to be replenished every month thereby leading to commercial impracticality. The efficiency of sub-10 femtosecond lasers was not practical until the year 2000 because of the prior need for dyes and flash lamps instead of YAG and Ti: Sapphire crystals pumped by light or laser emitting diodes.

Ultrashort pulses are prone to suffer phase distortions as they propagate through or reflect from optics because of their broad bandwidth. There have been recent experimental attempts to shape the phase of ultrashort pulses since shaped pulses have been shown to increase the yield of certain chemical reactions and multiphoton excitation.

Conventional pulse characterization is typically done by one of the following methods. Autocorrelation is a simple traditional method that yields only the pulse duration. Furthermore, frequency resolved optical gating (hereinafter "FROG") is a known method which yields phase and amplitude following iterative analysis of the time-frequency data. Interferometric methods such as DOSPM and spectral phase interferometry (hereinafter "SPIDER") yield phase and amplitude from frequency resolved Interferometric data; these are very complex and expensive but reliably provide the required information. Both FROG and SPIDER methods require some type of synchronous autocorrelation setup. In the case of the FROG method, autocorrelation is used to provide a time axis while a spectrometer provides the frequency domain information. In the case of the SPIDER method, the ultrashort pulse is split into three beams during autocorrelation; the pulse in one of the beams is stretched to provide the shear reference, while the other two pulses are cross-correlated with the stretched pulse at different times. The output is sent to a spectrometer where the interference in the signal is used to reconstruct the electric field. This extra synchronous autocorrelation step adds time and cost in addition to necessitating highly skilled operators. Limitations with prior devices and methods are discussed in R. Trebino et al., "Measuring Ultrashort Laser Pulses," *Optics & Photonics News* 23 (June 2001). Moreover, the Grenouille method requires a setup consisting of a Fresnel biprism, a doubling cryst and lenses that need to be specifically chosen for a particular pulse duration and wavelength, making this method less flexible.

In accordance with the present invention, a laser system using ultrashort laser pulses is provided. In another aspect of the present invention, the system includes a laser, pulse shaper and detection device. A further aspect of the present invention employs a femtosecond laser and a spectrometer. Still another aspect of the present invention uses a laser beam pulse, a pulse shaper and a SHG crystal. In yet another aspect of the present invention, a multiphoton intrapulse interference phase scan (hereinafter "MIIPS") system and method characterize the spectral phase of femtosecond laser pulses. In another aspect of the present invention, a system employs electromagnetic pulse shaping design to take advantage of multiphoton intrapulse interference. Fiber optic communication systems, photodynamic therapy and pulse characterization tests use the laser system with additional aspects of the present invention.

The laser system of the present invention is advantageous over conventional constructions since the MIIPS aspect of the present invention employs a single beam which is capable of retrieving the magnitude and sign of second and third order phase modulation directly, without iteration or inversion procedures. Thus, the MIIPS system is much easier to set up and use, thereby creating a much less expensive system which is more accurate than conventional systems and methods. Furthermore, the MIIPS system of the present invention avoids the inaccuracies of the prior FROG, SPIDER and DOSPM methods due to environmental effects such as wind, humidity and the like. The present invention MIIPS system utilizes the full bandwidth which works best with shorter laser beam pulses, such as femtosecond pulses; this is in contrast to the mere single frequency optimization of some convention devices. The present invention MIIPS system overcomes the traditional need for slower picosecond pulses for space-time correlation corrections due to inherent time delays created with prior synchronous use of multiple matched pulses, a first pump or fundamental pulse and another reference second harmonic pulse, caused by the pulse passage through a pulse shaping crystal. Additionally, the present invention advantageously uses one or more pre-stored comparison values for pulse signal decoding at a communications receiver such that the second reference pulse (and corresponding time delay correlation) are not necessary. The present invention also improves the encoding-decoding functionality of pulses by adding considerably more information to each pulse by obtaining the entire phase function directly from a phase scan. Intrapulse interferences of the present invention causes self separation (for example, inherent communication signal routing address differentiation) thereby allowing use of inexpensive receivers in an asynchronous manner, in other words, without the need for synchronous detection such as by traditional autocorrelation or interferometers. Additional advantages and features of the present invention will become apparent from the following description and appended claims, taken in conjunction with the accompanying drawings.

BRIEF DESCRIPTION OF THE DRAWINGS

FIGS. 2A-2C are schematic and graphical representations of two photon and three photon induced fluorescence employed with the system, wherein FIG. 2B is a schematic representation of the pulse spectrum (dashed line) and the phase (solid line);

FIGS. 3A-3D are sets of two and three photon absorption probability simulations and the laser beam pulse shapes employed, while

DETAILED DESCRIPTION OF THE PREFERRED EMBODIMENTS

System with Transmissive and Active Pulse Shaper

Figure 1:
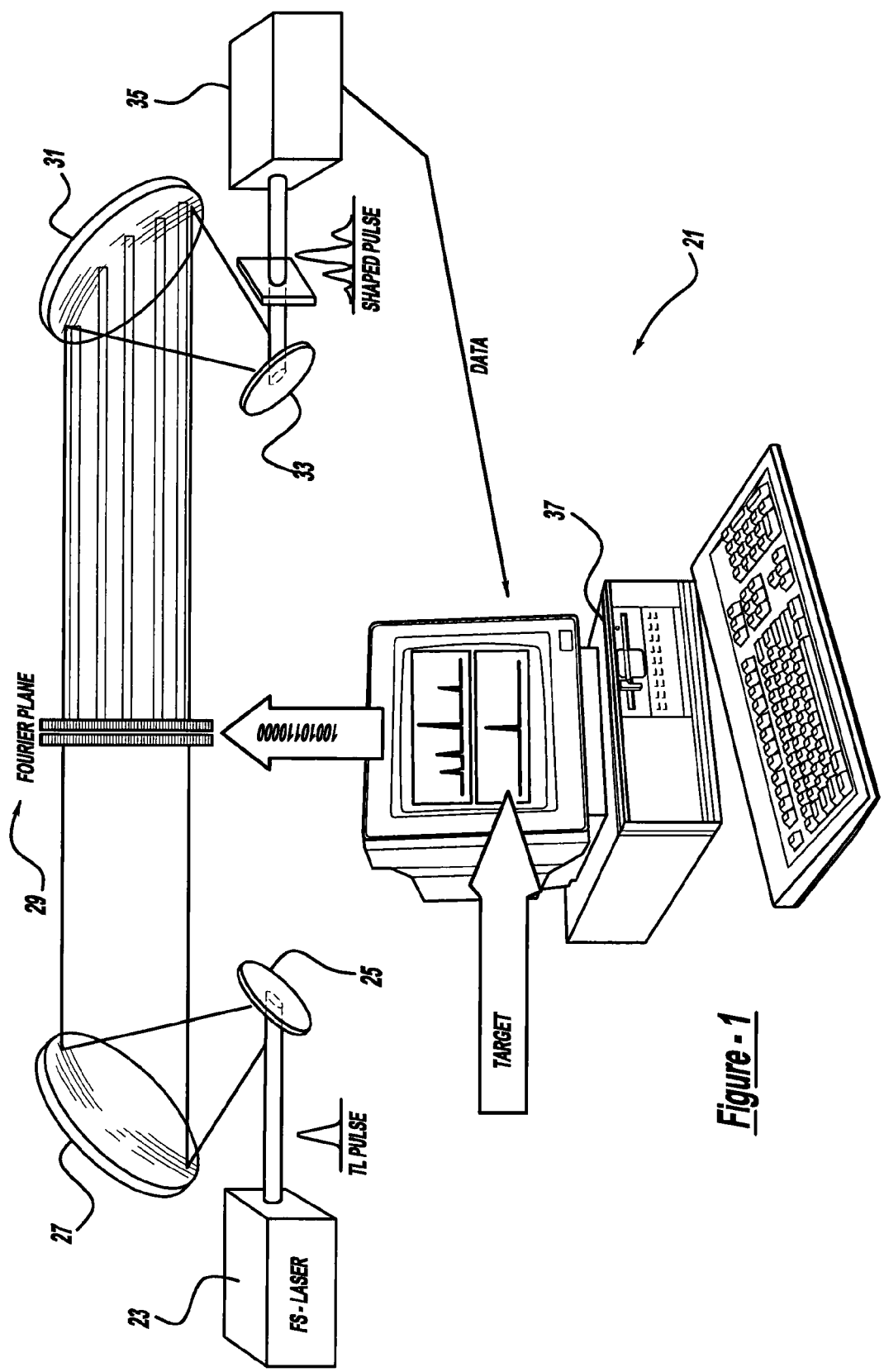
FIG. 1 is a diagrammatic view showing a first preferred embodiment of a laser system of the present invention.

The first preferred embodiment of a laser system 21 using ultrashort laser pulses of the present invention is generally shown in FIG. 1. System 21 includes a femtosecond laser 23, an upstream grating 25, an upstream convex mirror 27, a laser beam pulse shaper 29, a downstream concave mirror 31, a downstream grating 33, a detection device 35, and a personal computer 37. Personal computer 37 has a microprocessor based electrical control system, memory, an output screen, a data storage device, an input keyboard, and a removable disk. More specifically, the detection device is a spectrometer 39. Bursts or pulses of a laser beam 43 are emitted from laser 23, through the optics 25, 27, 31 and 33, as well as through pulse shaper 29 for detection and sensing by spectrometer 39 for further evaluation, analysis, comparison and subsequent control by personal computer 37.

The laser is preferably an ultra-short femtosecond laser that can deliver high peak intensity (with a typical peak greater than $10^{10}$ watts/cm$^2$) which preferably emits laser beam pulses of less than 100 femtosecond duration, and more preferably at or less than 50 femtoseconds, and for certain applications even more preferably at or less than 10 femtosecond duration, for each pulse burst or shot. The intense optical pulses that are required to modify material are formed in a Kerr-Lens modelocked titanium sapphire oscillator. Such lasers are capable of producing hundreds of nanometers of coherent bandwidth, although only about 50 nm are typically used. The output may be amplified in a 1 kHz regenerative chirped pulsed amplifier. The output pulse is typically 100 fs long with a central wavelength of 800 nm and total pulse energy of 0.1 to 1 mJ. Preferred lasers include: the Kapteyn and Murnane femtosecond laser oscillator, which can produce less than 15 fs pulses at 100 MHz; the Hurricane model from Spectra Physics Inc., which is diode pumped and gives 0.8 mJ per pulse with sub-50 fs pulses at 1 kHz; and the CPA-2001+ model from Clark-MXR Inc., which gives 1.3 mJ per pulse with sub-150 fs pulses at 1 kHz, pumping a Clark-MXR Inc. non-collinear parametric amplifier (hereinafter "NOPA") which produces 0.2 mJ per pulse, and is capable of generating sub-20 fs pulses. This NOPA system can even produce pulses between 10 fs and 4.5 fs.

A Fourier plane pulse shaper is preferably used with the present invention for the transmissive construction illustrated with this embodiment. Ultra-fast laser pulses contain from one to fifty optical cycles, and last only a few femtoseconds. This is much faster than most current electronics and therefore shaping with fast time gates is very difficult. On the other hand, as a consequence of the uncertainty principle, the optical spectrum spans tens to hundreds of nanometers. Such a large bandwidth is relatively easy to measure and to filter, and there are several techniques to shape the spectrum in the frequency domain, and thereby shape the temporal pulse upon recompression.

In order to access the frequency domain and the individual frequency components that comprise the pulse, a geometric arrangement is employed, using two back-to-back spectrometers. The spectrometers are especially designed to introduce no net temporal dispersion: that is, all colors pass through the spectrometers within the same amount of time. The first spectrometer (including grating 25 and mirror 27) spreads the unshaped pulse spectrum along a line according to its dispersion function y($\alpha$). The light intercepts spatial amplitude and phase mask pulse shaper 29 at this point. The mask output then forms the entrance to a second spectrometer (including grating 33 and mirror 31) which recombines the colors into a single shaped pulse.

The heart of pulse shaper 29 is the programmable 256 pixel liquid-crystal mask (consisting of two overlapping 128 pixel liquid crystal arrays) that is placed at the Fourier plane. For the applications envisioned herein, the mask must be capable of shifting the phase of individual frequencies. For alternate embodiment pulse shapers, a different electronically programmable mask that is capable of controlling phase has been demonstrated: a liquid crystal display (hereinafter "LCD"), an acousto-optic modulator (hereinafter "AOM"), a deformable mirror, and a permanently deformed mirror. A LCD pulse shaper can be obtained from CRI Co. and has a modulator electronic driver.

The AOM consists of an anti-reflection coated Tellurium Dioxide (TeO2) crystal with a piezo electric transducer glued onto one end. The central frequency of the acoustic wave is $\alpha c/2\pi$=200 MHz. The acoustic velocity vs in the crystal is 4.2 km/s and the light pulse spends less than 10 ps in the crystal, so the acoustic wave moves less than 0.002$\lambda$ acoustic during the transit of the light field through the crystal. Since the acoustic wave is essentially frozen as the optical pulse travels through the crystal, the complex amplitude of the acoustic wave traveling through the crystal in the y direction, A(t)cos αct=A(y/vs)cos αct, is mapped onto the optical field E(α) as it passes through the AOM. If some of the dispersed optical field encounters a weak acoustic wave, that frequency is attenuated; if the acoustic wave carrier is shifted by phase angle ø, that phase shift is imposed on the optical field. This pulse shaper has a total efficiency of about 20% including the diffraction efficiency of the AOM and the diffraction efficiency of the gratings. The diffracted light is used and the undiffracted "zero order" beam is blocked, to allow full modulation of both amplitude and phase in the shaped beam. The shaped beam than has the form $$E_{shaped}(\omega) = E_{input}(\omega) \times \alpha(\omega) \times e^{i\phi(\omega)t} \quad [1]$$

where $a(\omega)e^{i\phi(\omega)t} = A[y(\omega)/v_s]$; α is the frequency, and e is a constant.

Fixed pulse shaping optics, such as chirped mirrors, can also be employed as will be discussed further hereinafter with regard to FIG. 20.

The transform limited pulses (hereinafter "TL"), having all their frequencies in phase, are fed into the pulse shaper where curved mirror 27 focuses the spectrum onto Fourier plane 29. Changes in the phase ø and amplitude A of the spectral components indicated by the computer are used to tailor the laser pulse before reconstruction with second curved mirror 31 and grating 33. Once compressed, the shaped pulse is directed to spectrometer 39 for evaluation. The Fourier transform relationship between the time and the frequency domain allows us to calculate the necessary mask to create a certain shaped pulse. These calculations are based on $$f(v) = \frac{1}{2\pi} \int_{\infty}^{0} f(t) e^{i2\pi vct} dt \quad [2]$$

and $$f(t) = \int_{\infty}^{0} f(v) e^{-i2\pi vct} dv \quad [3]$$

where v is the frequency in wave numbers, t is the time, and c is the speed of light.

In this embodiment, the phase and amplitude masks of the pulse shaper are controlled by the computer wherein the laser pulse shape takes a dynamic role. The microprocessor within personal computer 37 will then control laser 23, receive an essentially real time feedback input signal from spectrometer 39, and then perform calculations, comparisons and evaluations, and possibly automatic variation of subsequent pulse shapes. These automated steps can be substituted with manual user calculations and decisions if desired based on personal computer outputs.

System with Reflective Pulse Shaper

Figure 15:
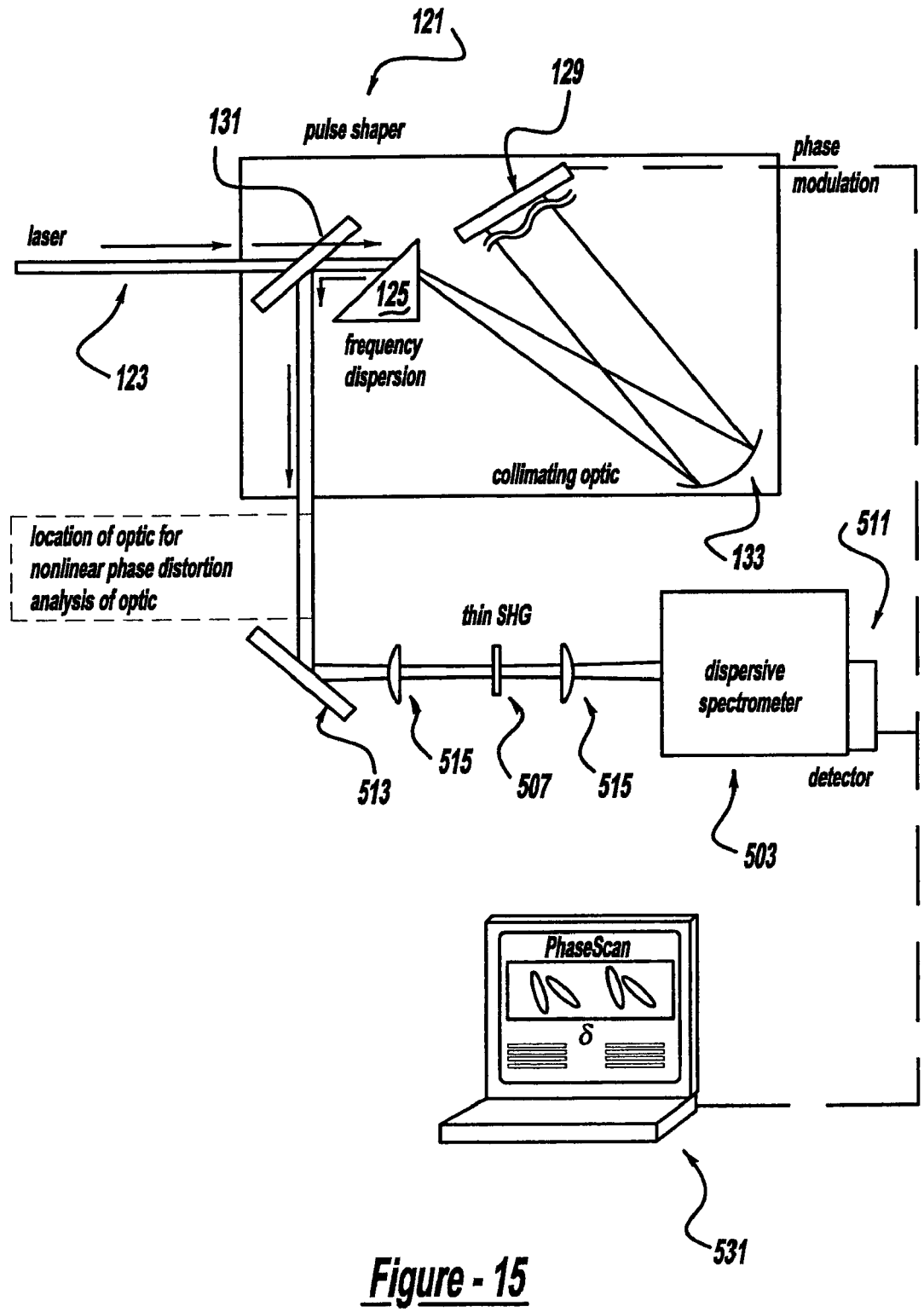
FIG. 15 is a diagrammatic view showing a sixth preferred embodiment of the system of the present invention for use with pulse characterization.

A reflective pulse shaping system 121, employed with a sixth preferred embodiment of the present invention is shown in FIG. 15, and includes a femtosecond laser 123, an upstream prism 125, a partially cylindrical or partially spherical mirror 133, a pulse shaping mirror 129 at the Fourier plane, and an offset or pickoff mirror 131. Upstream prism 125 initially acts to disperse the colors of the emitted laser beam pulse while mirror 133 serves to focus, collimate and redirect this dispersed laser beam pulse toward pulse shaping mirror 129. Pulse shaping mirror 129 has either a predetermined or fixed pulse shaping surface or a computer controlled deformable mirror.

Figure 20:
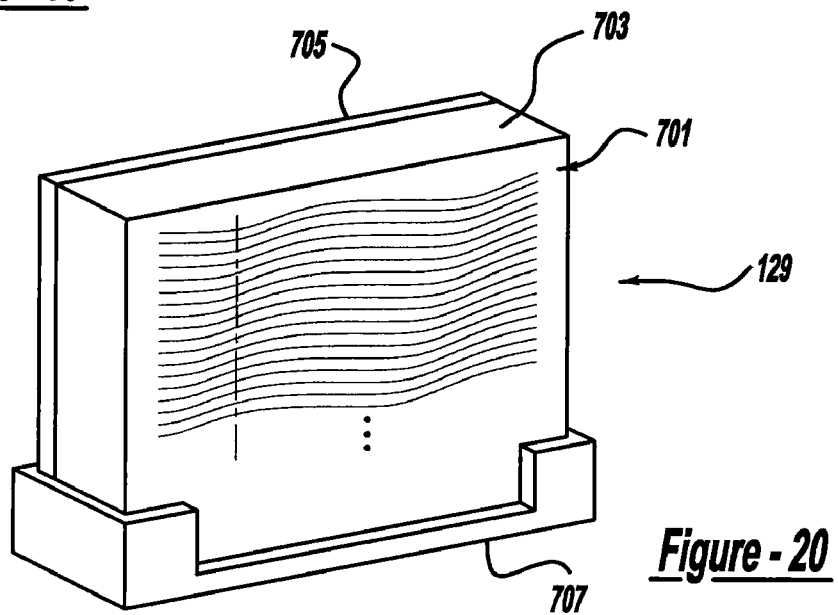
FIG. 20 is a perspective view showing a preferred embodiment of a fixed, two-dimensional shaper employed in the present invention system.

For the fixed pulse shaper, as shown in FIG. 20, the patterned shaping surface has, for example, a sinusoidal profile along the direction of frequency dispersion. If the profile is slanted then the vertical axis provides different phase modulation that can be used for a single shot pulse characterization or decoding in a communications application. The surface modulation wave forms are schematically shown as 701. Inexpensive replicas can be achieved by injection molding with polymers such as pmma substrate 703 and reflection coated or anti-reflection coated depending if it is used in reflection or transmission mode respectively. The physical characteristic or shape of the actual pulse shaping surface is predetermined through optimization experimentation for the intended use and intended laser beam input; each row (or column) of the shaped wave is displaced or offset in phase from the immediately adjacent rows or shaped wave form patterns. Cosine, stepped or other wave form patterns can also be used. A silver coating 705 is applied to the front side of substrate 703 if used as a reflective pulse shaper as preferred with this embodiment. Alternately, anti-reflective coatings are applied to substrate 703 if fixed pulse shaper 129 is used as a transmissive optic. Substrate 703 can be removably snapped into a receptacle 707 and replaced by differently configured wave form patterns for different pulse phases and uses. After the desired mirror surface shape is known for the intended use, the less expensive, fixed shape mirror can be employed to reduce equipment costs for actual production systems. Also, the computer and optimization program are not required for these types of known set up and known applications after the initial determination is conducted. Pulse shaping with a permanently shaped optic to achieve specific tailoring of the phase of a fs laser pulse. The optic can be reflective or transitive. Motion of the optic can be use to cause the phase function to scan from odd to even. This setup can be used to encode and decode the phase of fs laser pulse.

Pulse shaper 129 thereby reshapes the laser beam pulse to now include one or more certain characteristic, reflects it back through the same prism and mirror in reverse order, and in an offset or time-delayed manner. Offset mirror 131 subsequently reflects the shaped laser beam toward the receiver, which can be a spectrometer, fiber optic sensor/switch, or a targeted tissue specimen, as will be discussed in greater detail hereinafter. It is further envisioned that an in-line optical system can be used, such as that disclosed with the first preferred embodiment, however, the pulse shaper at the Fourier plane would be replaced by a phase mask shaper having a transmissive optic with a predetermined coefficient of refraction, or a polarizing-type sine mask on a transparent substrate. Also, a polymer-doped glass or blend of polymer sheets that are capable of retarding the phase of the laser beam pulse wave or otherwise varying a wavelength, timing or shaping characteristic of same can be employed.

Alternately, certain optics can be used such as a backside coated, chirped mirror having multiple dichroic layers, which would be satisfactory for pulse shaping without dispersive optics and without the need for a Fourier plane. An acceptable chirped mirror is disclosed in Matuschek, et al, "Back-side-coated Chirped Mirrors with Ultra-smooth Broadband Dispersion Characteristics," *Applied Physics B*, pp. 509-522 (2000). A negative dispersion mirror from CVI Laser Corp., part no. TNM2-735-835-1037 is another suitable example. A rotatable wheel having multiple different chirped mirrors, each with specific pulse shaping characteristics, can also be used to provide a discrete number of predetermined shaped pulses.

Optical Coherence Tomography

Figure 6:
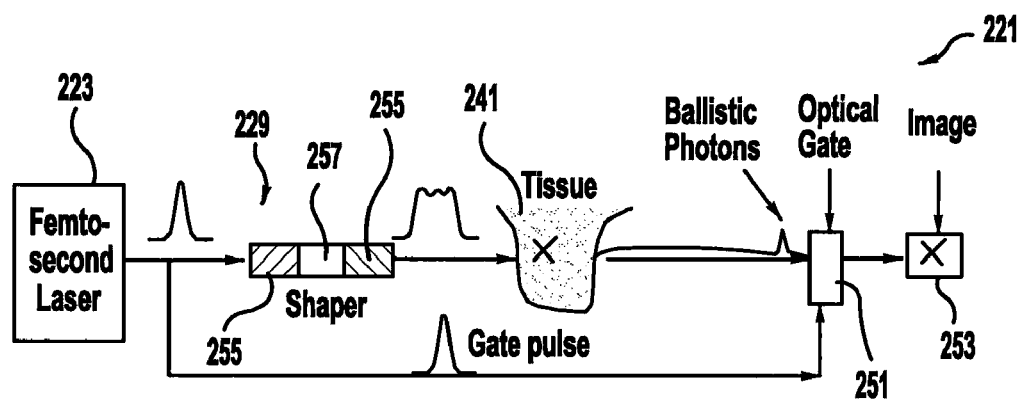
FIG. 6 is a diagrammatic view showing second and third preferred embodiments of the present invention system applied to optical coherence tomography and photodynamic therapy.

A second preferred embodiment of the present invention uses a laser system 221 for laser excitation or ionization with Optical Coherence Tomography ("OCT"). In general, FIG. 6 illustrates the OCT application of system 221 wherein there is a femtosecond laser 223, a laser beam shaper 229, a human or animal tissue specimen 241, an optical gate 251 and an image 253. Laser 223 emits a laser beam pulse shorter than 1 picosecond. Shaper 229 is made of three parts; two dispersive elements 255 which sandwich a phase mask element 257. Shaper 229 essentially prevents multiphoton excitation which can damage the person's or animal's DNA, as will be discussed in more detail as follows. An unshaped laser beam pulse is used to gate the ballistic photons to render the image for tomography use. Optical gating can be accomplished by up-conversion in a frequency doubling crystal or with a kerr-gate in liquid carbon disulphide. The construction of system 221 as illustrated supposes transmission imaging; the same end result can alternately be accomplished with back scattered imaging. Image 253 could be viewed like an x-ray-type image of the internal organs of the human or animal specimen but without harmful three photon exposure. The use of the shaped pulse in OCT provides for an increase in laser intensity for better imaging while preventing the damaging effects caused by multiphoton excitation of healthy tissue. The MIIPS process discussed hereinafter can be advantageously used to activate different dyes and other compounds within a human or animal tissue, to achieve compound specific or functional OCT or microscopy.

Photodynamic Therapy

A third preferred embodiment of the present invention uses a system also shown as 221 for laser excitation or ionization with photodynamic therapy ("PDT"). In general, FIG. 6 also illustrates the PDT application of system 221, but optical gate 251 and image 253 are not required. Shaper 229 allows two photon excitation but essentially prevents three photon excitation. Shaper 229 enhances the laser induced activity of a therapeutic agent which prevents damage of healthy tissue. Use of laser beam pulse shaping of the present invention should provide superior control and results for PDT applications as compared to those practically possible with conventional methods as disclosed, for example, in U.S. Pat. No. 6,042,603 entitled "Method for Improved Selectivity in Photo-Activation of Molecular Agents" which issued to Fisher et al. on Mar. 28, 2000, and is incorporated by reference herein. Alternately, the pulse shaper can be tuned to target cancerous cells for multiphoton gene therapy or destruction, with or without the presence of a therapeutic agent, without damaging healthy tissue. The MIIPS process discussed hereinafter can be advantageously used to activate only certain pharmaceuticals or chemicals, or used to allow the laser pulse to enter human or animal tissue to a known depth, based on the phase tuning and associated nonlinear spectrum tuning of the laser beam pulse.

Control of Nonlinear Optical Processes

As applied to all of the applications herein, selective control of one and multiphoton processes in large molecules, including proteins, is possible using a simple pulse shaping method that is based on taking maximum advantage of the multiphoton intrapulse interference caused in short pulses with large bandwidths. The results show an extraordinary level of control that is robust and sample independent, with contrast ratios near two orders of magnitude (clearly visible with the naked eye). Such large contrast ratios allow for more precise cancellation control of undesired photons and other laser beam characteristics, such that nonlinear transitions induced by each pulse are controlled. Because simple phase functions can be incorporated into a passive optical component such as mirror 129 (see FIG. 15), these applications do not require the complexity and expense of computer controlled pulse shapers after initial set up, although systems can still be employed.

Figure 2A:
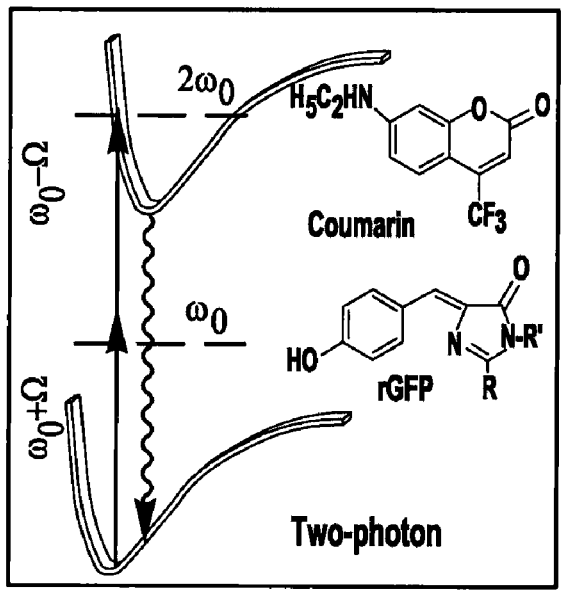
Figure 2B:
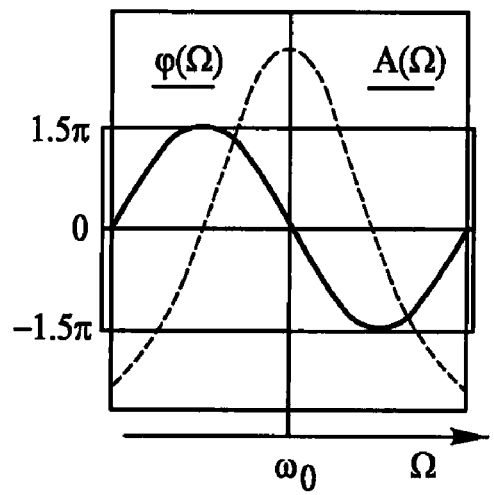
Figure 2C:
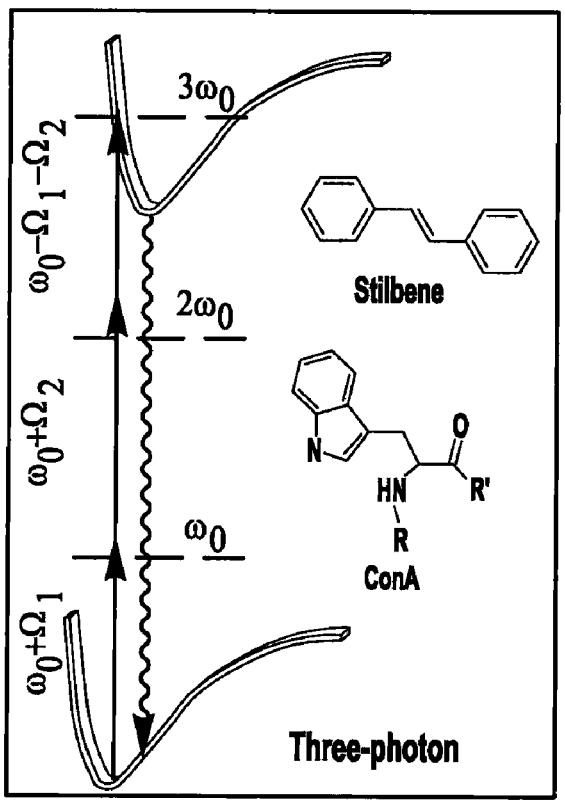

The underlying concept of the system and associated method are shown in FIGS. 2A-2C. Multiphoton transitions are optimized when the central bandwidth of the laser pulse $\omega_0$, is some fraction (half for two-photons, a third for three-photons, etc.) of the total energy of the transition as illustrated in FIGS. 2A and 2C. For ultrafast pulses, when the bandwidth is large, different frequency components ($\omega_0 \pm \Omega$) of the pulse can interfere, thereby reducing the probability for multiphoton excitation. Referring to FIG. 2B, the spectrum of the ultrafast laser pulse with amplitude $A(\Omega)$ is plotted as a function of detuning from the central frequency. A phase mask $\phi(\Omega)$ can be imprinted on the pulse such that the phase of each frequency component $\Omega$ acquires a specific value. The effect of pulse shaping on the probability for two-photon absorption (hereinafter "2PA") can be calculated as follows:

$$P_{2PA} \propto \left| \int_{-\infty}^{\infty} A(\Omega)A(-\Omega)\exp[i\{\phi(\Omega) + \phi(-\Omega)\}]\, d\Omega \right|^2 \qquad [4]$$

and for three-photon absorption ("3PA"), a similar formula can be derived as follows:

$$P_{3PA} \propto \left| \int_{-\infty}^{\infty}\int_{-\infty}^{\infty} A(\Omega_1)A(\Omega_2)A(-\Omega_1-\Omega_2)\exp[i\{\phi(\Omega_1) + \phi(\Omega_2) + \phi(-\Omega_1-\Omega_2)\}]\, d\Omega_1\, d\Omega_2 \right|^2 \qquad [5]$$

where amplitudes and phases are introduced for two different detuning values $\Omega_1$ and $\Omega_2$, as shown in FIG. 2C. One photon transitions are not affected by the phase of the pulses, however, exclusive one photon excitation is difficult to achieve at high photon flux due to the onset of multiphoton processes.

A schematic representation of two photon and three photon induced fluorescence is illustrated in FIGS. 2A and 2B, respectively. The vertical arrows represent ultrafast pulses that induce the two and three photon transitions. Because of their broad bandwidth, ultrafast pulses contain photons that are detuned from the central wavelength $\omega_o$ by an amount $\Omega$. Referring again to FIG. 2C, ultrafast laser pulses are shaped using a sine function phase mask across the pulse spectrum underlying the dashed curve while the structures of the chromophores are also shown.

Example 1

The experiments in all of the following examples were carried out using an amplified titanium sapphire laser producing 50 fs pulses. The pulses were shaped using a spatial light modulator (hereinafter "SLM") at the Fourier plane of a zero-dispersion two grating arrangement. The two independent modulator plates, based on liquid crystal technology in the SLM (128 pixels each), were calibrated so that only phase delays were introduced without changes to the output spectrum, intensity, and polarization. The shaped pulses centered at 809 nm were characterized by second harmonic generation frequency resolved optical gating. When all phases were set to zero, laser pulses were near transform limited. Unless indicated otherwise, measurements were made with pulse energies of 0.4 µJ/pulse at the sample. Experiments were carried out by setting the phase function equal to a sinusoid, as shown in FIG. 2B, in the 779-839 nm spectral range. Emission from one photon or multiphoton induced processes from various samples was measured as a function of δ, the phase shift of the mask across the spectrum. The maximum phase advancement or retardation was 1.5π.

Equations 4 and 5 can be used to calculate the expected signal for two and three photon processes as a function of δ. These calculations are graphed in FIGS. 3A-3H for sinusoidal phase functions having a half (FIGS. 3A and 3B) or a full (FIGS. 3C and 3D) period across the entire phase mask. The calculated probability for two photon and three photon transitions peaks at half integer values of π in FIGS. 3A and 3B, while the calculated probability for two photon and three photon transitions peaks at integer values of π in FIGS. 3C and 3D. The shape of the phase function, where maxima and minima in the probability are achieved, is indicated as inserts.

Experimental data were obtained with the phase functions used for the calculations in FIGS. 3A-3D. In these experiments, the two and three photon emission from large organic molecules is detected as a function of δ. Although the model described by equations 4 and 5 assumes two level systems, FIGS. 3E-3H experimentally demonstrate that this principle can be applied to complex systems having a manifold of vibrational states broadened by the presence of a solvent. It is noteworthy that the peaks and valleys predicted by equations 4 and 5 are observed in the experimental data; essentially, the intensity maxima are found when the phase function is anti-symmetric with respect to the central wavelength of the pulse and minima when it is symmetric.

Figure 3E:
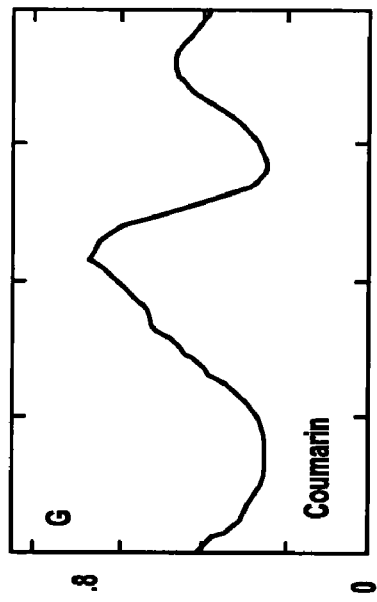
FIGS. 3E-3H are experimental results.
Figure 3G:
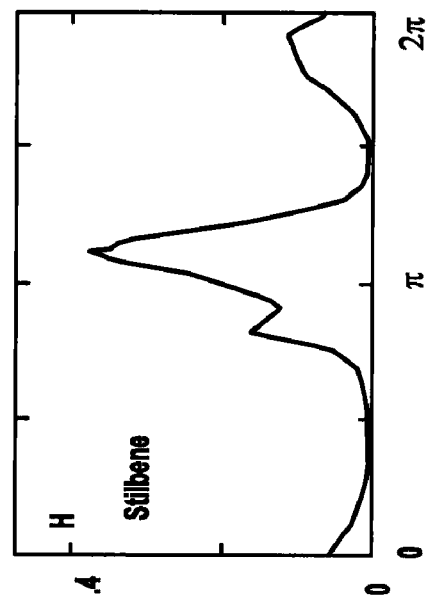
Figure 3F:
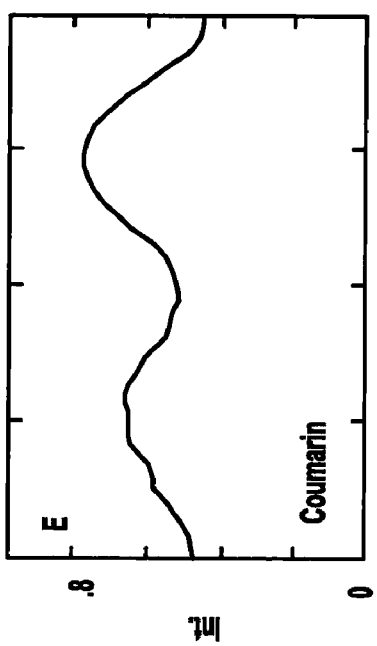
Figure 3H:
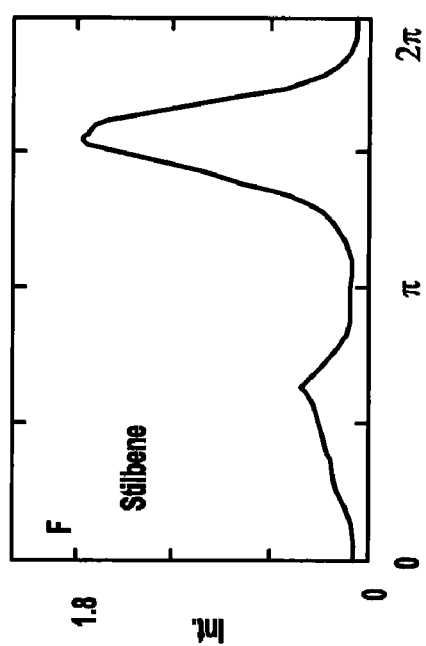

More specifically, theoretical and experimental phase-mask control of two and three photon induced fluorescence is shown in FIGS. 3A-3H. Equations 4 and 5 predict that as the phase mask is translated by an amount δ, the probability of two (hereinafter "$P_{2PA}$") and three photon transitions (hereinafter "$P_{3PA}$") is modulated, as illustrated in FIGS. 3A-3D, for a half period sine mask (FIGS. 3A and 3B) and a full period sine mask (FIGS. 3C and 3D). Transform limited pulses yield a maximum value of 1. The small inserts in FIGS. 3A and 3C display the phase function at specific positions where maximum and minimum values of fluorescence take place (FIGS. 3E-3H) wherein experimental two and three photon laser induced fluorescence measured for Coumarin and Stilbene, respectively, as a function of phase mask position δ are shown. The phase masks used for these experiments were the same as those used in the calculations. Thus, the pulse shaping masks can be predetermined or fixed in shape based on calculations, experiments or learning program values for known equipment and known specimens.

Example 2

Figure 4A:
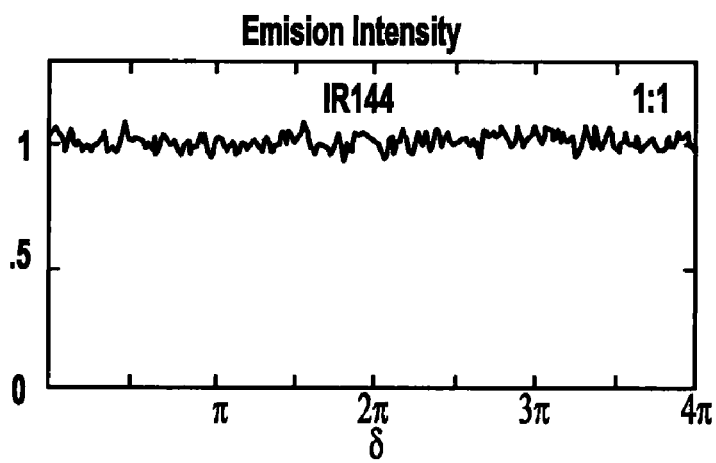
FIGS. 4A-4G are experimental results obtained with the system for two and three photon induced fluorescence.
Figure 4B:
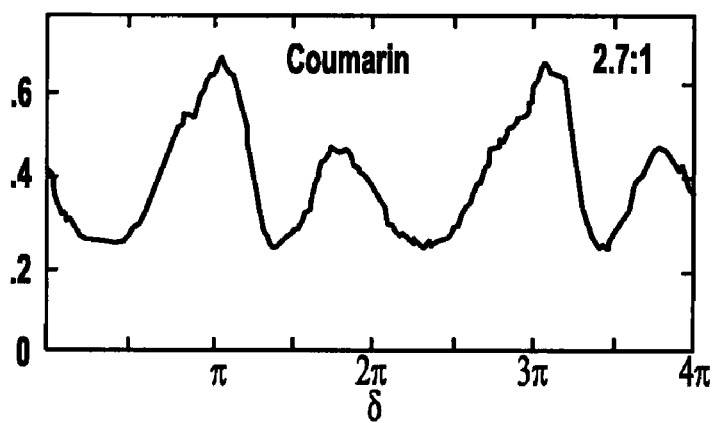
Figure 4C:
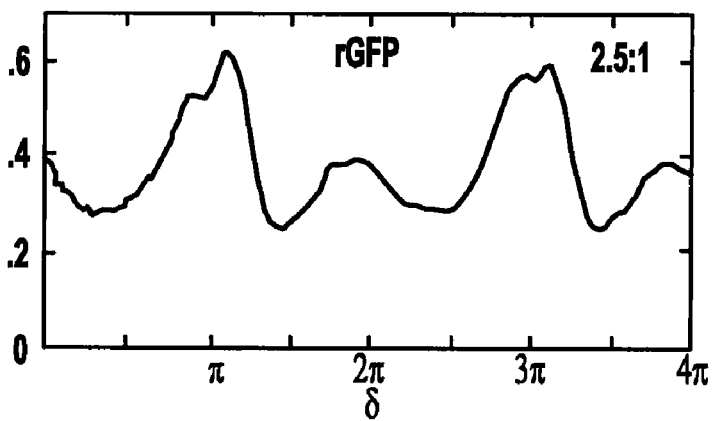
Figure 4D:
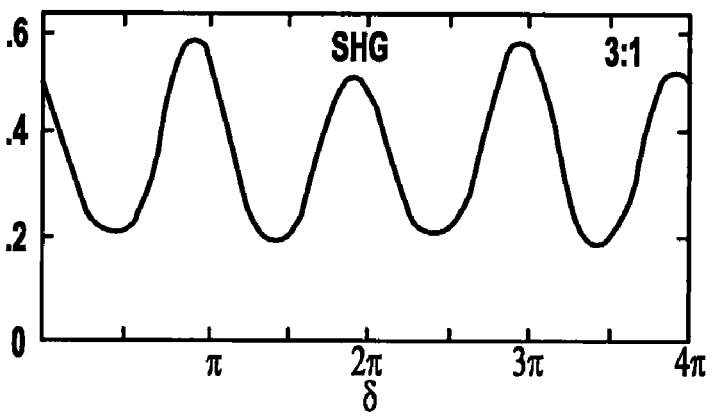

Experimental results for various samples obtained with a full-period sinusoidal phase mask are shown in FIGS. 4A-4G. FIG. 4A shows one photon laser induced fluorescence (hereinafter "1PLIF") of IR144 observed at 842 nm as a function of phase mask position. This measurement was made with 0.3 nJ/pulse to avoid nonlinear processes at the specimen. It is noteworthy that one photon process in the weak field regime show no dependence on phase shaping. FIG. 4B shows results for the two photon laser induced fluorescence (hereinafter "2PLIF") from Coumarin collected at 500 nm. The data in FIG. 4C shows the dependence of 2PLIF in recombinant green fluorescent protein (hereinafter "rGFP") detected at 505 nm. The data in FIG. 4D corresponds to the intensity of the second harmonic generation (hereinafter "SHG") signal at 405 nm from a 0.3 mm β-barium borate crystal. The maximum and minimum signal for SHG coincides with that observed for 2PLIF but is not identical.

Figure 4E:
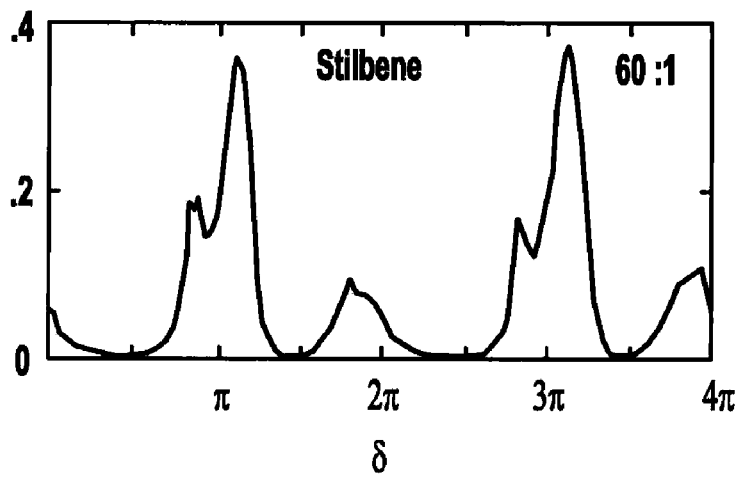
Figure 4F:
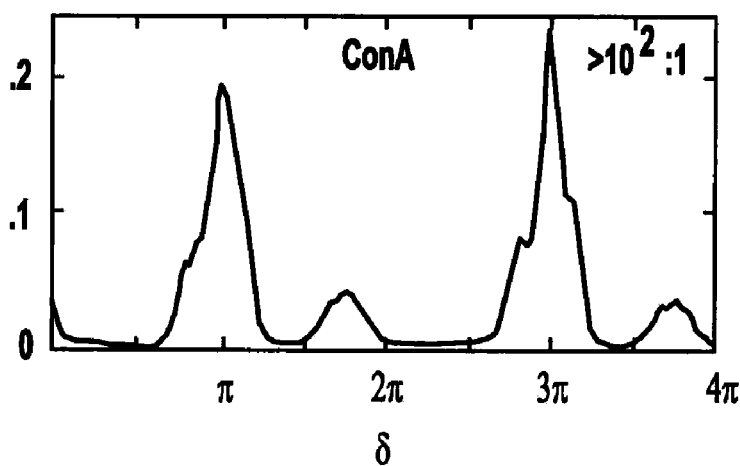
Figure 4G:
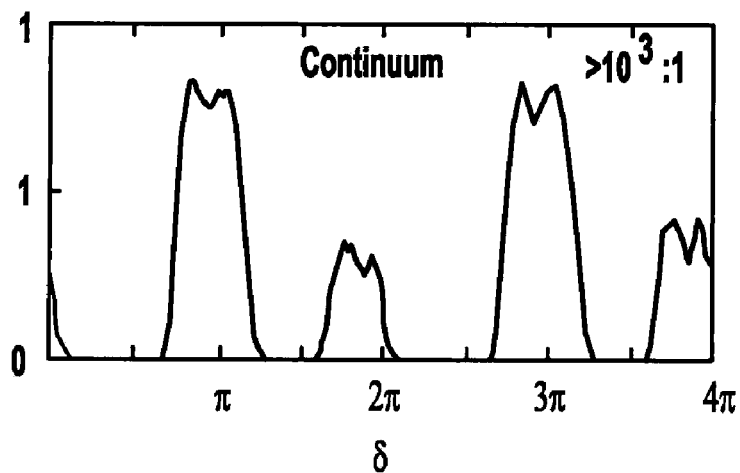

With reference to FIG. 4E, the dependence of three photon laser induced fluorescence (hereinafter "3PLIF") from Trans-Stilbene is illustrated. The signal was collected at 350 nm as a function of δ. In this case, the maximum contrast (max:min) is measured to be 60:1. The data in FIG. 4F corresponds to the 3PLIF from Tryptophan residues in Con A, collected at 350 nm. In 3PLIF the maximum fluorescence signal is less than that obtained for transform limited pulses (when all the phases in the mask are set equal to zero), but the overall contrast ratio over the three-photon excitation is excellent, approaching two orders of magnitude. The data in FIG. 4G corresponds to the continuum generation response (a nonlinear self-frequency modulation process yielding white light pulses) from a 3 mm slab of quartz detected at 600 nm.

More specifically, FIGS. 4A-4G demonstrate the experimental measurements of one and multi-photon emission obtained as a function of phase mask position δ. In all cases, the phase mask is a full period sine function. The signal measured with transform limited pulses is unity. The contrast ratio (max:min) is given in the upper right corner of each of the experimental plots. Here we find that the higher the order of the optical nonlinearity, the greater the contrast that we observe, therefore discrimination among different order processes is possible. In other words, the higher the order, the greater the photons, which makes it easier for photon cancellation. Also, the greater the contrast ratio, the more the background noise is filtered out.

Example 3

Figure 5A:
FIGS. 5A-5F are sets of pie charts and laser beam pulse shape graphs showing contrast ratios obtained with the system.
Figure 5B:
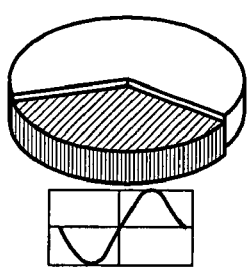
Figure 5C:
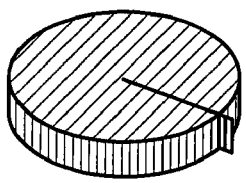
Figure 5D:
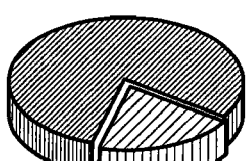

FIG. 5A presents the maximum discrimination between linear and nonlinear response observed for intense pulses (0.5 µJ/pulse). Separate detectors simultaneously collected the 1PLIF from IR144 solution and a portion of the continuum output. Maximum and minimum contrast ratios of $>10^3:1$ and 1:0.6 were obtained for one photon process versus continuum, respectively, as shown in FIGS. 5A and 5B. This control is extremely valuable when one is interested in linear processes under high-flux conditions, like in laser microscopy or in optical fiber communications. Using the simple phase function discussed earlier, particular windows of opportunity to control second versus higher order processes can be employed as demonstrated in FIGS. 5C and 5D. For certain values of δ, continuum generation even for relatively high intensity laser pulses (~1 µJ/pulse) can be completely suppressed. FIGS. 5C and 5D show that maximum and minimum contrast ratios of $>10^3:1$ and 1:4 were obtained for 2PLIF versus continuum, respectively.

Figure 5E:
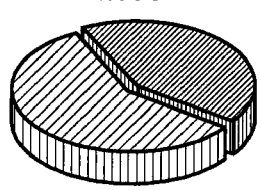
Figure 5F:
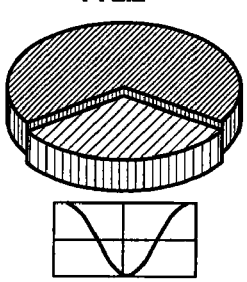

Two photon transitions can be achieved while suppressing three photon processes for use in two photon microscopy or in two photon PDT. This type of control is much more difficult because once multiphoton transitions take place it is very difficult to stop at a particular order. A mixture of Coumarin and Fluoranthene were prepared to explore control of 2PLIF versus 3PLIF. Because fluorescence from these two molecules overlaps the same spectral region, the separation between the two signals was achieved by temporal gating. Coumarin fluorescence was detected at 495 nm during the first 20 ns, while fluoranthene fluorescence was detected at 460 nm with a gate that opened 40 ns after the initial rise and extended for 120 ns. Maximum and minimum contrast ratios of 1.4:1 and 1:2.2 were obtained for 2PLIF versus 3PLIF, respectively, as presented in FIGS. 5E and 5F. The contrast data presented in FIGS. 5A-5F were obtained when transform limited pulses yielded equal intensities for the processes. Better contrast can be obtained using additional pulse shaping as described in the following section, especially as the multiphoton processes are detuned from resonance.

Predetermined Pulse Shaping and Phase Control of Multiphoton Processes

The present invention takes maximum advantage of the phenomenon described as "Multiphoton Intrapulse Interference" as optimized for large molecules, proteins, and other condensed phase materials, through a combination of: (a) a chirped mask pulse shaper; and (b) a smooth function of phase versus frequency for the mask pulse shaper. The following formulas provide a predictive advantage for finding appropriate phase masks. The probability of two photon transitions can be calculated as follows for any given pulse shape: For an electric field with a carrier frequency $\omega_0$ and a slow amplitude $E_0(t)$, $$E(t) = E_0(t)e^{-i\omega_0 t} \text{ and } E_0(t) = \frac{1}{\sqrt{2\pi}} \int_{-\infty}^{\infty} F_0(\Omega)e^{-i\Omega t} d\Omega \quad [6]$$

where the Fourier image $F_0(\Omega)$ around carrier frequency $\Omega = \omega - \omega_0$ can be written as:

$$F_0(\Omega) = \frac{1}{\sqrt{2\pi}} \int_{-\infty}^{\infty} E_0(t)e^{i\Omega t} dt, \quad [7]$$

the amplitude of two photon transition at resonance frequency $\omega$ is:

$$A_2(\omega) \propto \int_{-\infty}^{\infty} E(t)^2 e^{i\omega t} dt = \int_{-\infty}^{\infty} E_0(t)^2 e^{i(\omega - 2\omega_0)t} dt = \int_{-\infty}^{\infty} E_0(t)^2 e^{i\Delta t} dt, \quad [8]$$

where detuning $\Delta = \omega - 2\omega_0$, the probability of two photon transition is:

$$P_2(\omega) = |A_2(\omega)|^2. \quad [9]$$

Furthermore, the Fourier image of convolution is the product between Fourier images $$T(f*g) = (Tf)(Tg) \quad [10]$$

where convolution (*, function from $\Delta$) of two functions (f) and (g) is:

$$f*g = \frac{1}{\sqrt{2\pi}} \int_{-\infty}^{\infty} f(\Omega)g(\Delta - \Omega) d\Omega. \quad [11]$$

Direct (T, function from $\Omega$) and inverse ($T^{-1}$, function from t) Fourier images are $$T(f) = \frac{1}{\sqrt{2\pi}} \int_{-\infty}^{\infty} f(t)e^{i\Omega t} dt \text{ and} \quad [12]$$

$$T^{-1}(f) = \frac{1}{\sqrt{2\pi}} \int_{-\infty}^{\infty} f(\Omega)e^{-i\Omega t} d\Omega.$$

Additionally, the relation between direct and reverse transforms is:

$$T^{-1}T(f) = TT^{-1}(f) = f. \quad [13]$$

Thus, using the inverse transform, the formula can be written as:

$$f*g = T^{-1}T(f*g) = T^{-1}[(Tf)(Tg)] \text{ or} \quad [14]$$

formula [14] in integral form is as follows:

$$\int_{-\infty}^{\infty} f(\Omega)g(\Delta - \Omega) d\Omega = \quad [15]$$
$$\int_{-\infty}^{\infty} e^{i\Delta t} \left[ \left( \frac{1}{\sqrt{2\pi}} \int_{-\infty}^{\infty} f(\Omega)e^{-i\Omega t} d\Omega \right) \left( \frac{1}{\sqrt{2\pi}} \int_{-\infty}^{\infty} g(\Omega)e^{-i\Omega t} d\Omega \right) \right] dt.$$

The time-frequency transformation can be calculated. Using the spectral presentation of formula [7] and convolution theorem of formula [15], formula [8] can be rewritten to obtain the formula for two photon transitions as follows:

$$A_2(\Delta) \propto \int_{-\infty}^{\infty} E_0(t)^2 e^{i\Delta t} dt \propto \int_{-\infty}^{\infty} F_0(\Omega) F_0(\Delta - \Omega) d\Omega \quad [16]$$

This expression provides the two photon absorption amplitude given the spectrum of the laser pulse $F_0(\Omega)$ and the detuned spectrum of the $F_0(\Delta - \Omega)$ that depends on the absorption spectrum of the sample.

The probability of three photon transitions can be subsequently calculated. The complex amplitude of transition is:

$$A_3(\omega) \propto \int_{-\infty}^{\infty} E(t)^3 e^{i\omega t} dt = \int_{-\infty}^{\infty} E_0(t)^3 e^{i\Delta t} dt, \quad [17]$$

where detuning $\Delta = \omega - 3\omega_0$. Using the reverse Fourier presentation for the fields of formula [6], formula [17] can be rewritten as:

$$A_3(\omega) \propto \int_{-\infty}^{\infty} e^{i\Delta t} \quad [18]$$
$$\left[ \int_{-\infty}^{\infty} F_0(\Omega)e^{-i\Omega t} d\Omega \int_{-\infty}^{\infty} F_0(\Omega)e^{-i\Omega t} d\Omega \int_{-\infty}^{\infty} F_0(\Omega)e^{-i\Omega t} d\Omega \right] dt$$

Next, equation [18] can be rewritten using a new function $G(\Omega)$ $$A_3(\omega) \propto \int_{-\infty}^{\infty} e^{i\Delta t} \left[ \int_{-\infty}^{\infty} F_0(\Omega_1)e^{-i\Omega_1 t} d\Omega_1 \int_{-\infty}^{\infty} G(\Omega_1)e^{-i\Omega_1 t} d\Omega \right] dt, \quad [19]$$

where $G(\Omega_1)$ is defined as the kernel of the integral $$\int_{-\infty}^{\infty} G(\Omega_1)e^{-i\Omega_1 t} d\Omega_1 = \quad [20]$$
$$\int_{-\infty}^{\infty} F_0(\Omega_1)e^{-i\Omega_1 t} d\Omega_1 \int_{-\infty}^{\infty} F_0(\Omega_1)e^{-i\Omega_1 t} d\Omega_1, \text{ and}$$

using the convolution formula [15], the following formula is obtained:

$$A_3(\omega) \propto \int_{-\infty}^{\infty} F_0(\Omega_1) G(\Delta - \Omega_1) d\Omega_1. \quad [21]$$

The Fourier image of the Reverse Fourier image of equation [20] defines the intermediate function using relationship of equation [13] and the integral form of the convolution theorem expressed in formula [15] as:

$$G(\Delta - \Omega_1) \propto \quad [22]$$

$$\int_{-\infty}^{\infty} e^{i(\Delta-\Omega_1)t} \left[ \int_{-\infty}^{\infty} F_0(\Omega_2) e^{-i\Omega_2 t} d\Omega_2 \int_{-\infty}^{\infty} F_0(\Omega_2) e^{-i\Omega_2 t} d\Omega_2 \right] dt =$$

$$\int_{-\infty}^{\infty} F_0(\Omega_2) F_0(\Delta - \Omega_1 - \Omega_2) d\Omega_2$$

The final formula for the detuned $\Delta = \omega - 3\omega_0$ three photon transition is obtained by using equations [21] and [22] after changing the order of integration:

$$A_3(\Delta) \propto \int_{-\infty}^{\infty} E_0(t)^3 e^{i\Delta t} dt = \quad [23]$$

$$\int_{-\infty}^{\infty} \cdots \int_{-\infty}^{\infty} F_0(\Omega_1) F_0(\Omega_2) F_0(\Delta - \Omega_1 - \Omega_2) d\Omega_1 d\Omega_2$$

such that the probability is:

$$P_3(\omega) = |A_3(\omega)|^2. \quad [24]$$

The method described above gave the formula for the n-photon transition by recurrence:

$$A_n(\Delta) \propto \int_{-\infty}^{\infty} E_0(t)^n e^{i\Delta t} dt \propto \int_{-\infty}^{\infty} \cdots \quad [25]$$

$$\int_{-\infty}^{\infty} F_0(\Omega_1) \ldots F_0(\Omega_{n-1}) F_0(\Delta - \Omega_1 \ldots - \Omega_{n-1}) d\Omega_1 \ldots d\Omega_{n-1}$$

where detuning is $\Delta = \omega - n\omega_0$. Thus, $$P_n(\omega) \propto |A_n(\omega)|^2. \quad [26]$$

It is also desirable to take into account inhomogeneous broadening (as encountered in solutions and condensed phase materials). The integrated probability for the n-photon transition in molecules with spectral a density $g_n(\omega)$ with amplitude defined by formula [25] is proportional to the weighed average (1)

$$P_n = \int_{-\infty}^{\infty} g_n(\omega) |A_n(\omega)|^2 d\omega. \quad [27]$$

Normalization for the case of transform limited laser pulse is $N_n$ and $$N_n = \int_{-\infty}^{\infty} g_n(\omega) |A_{TLn}(\omega)|^2 d\omega, \quad [28]$$

where $$A_{TLn}(\omega) = \ldots \int_{-\infty}^{\infty} |F_0(\Omega_1)| \ldots \quad [29]$$

$$|F_0(\Omega_{n-1})||F_0(\Delta - \Omega_1 \ldots - \Omega_{n-1})| d\Omega_1 \ldots d\Omega_{n-1}.$$

Figure 7C:
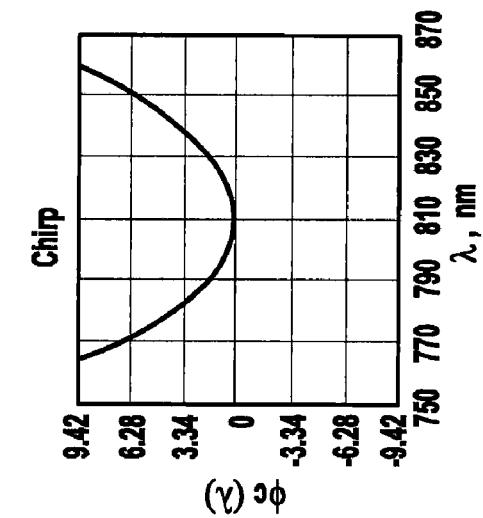
FIGS. 7A-7C are graphs showing the laser beam pulse spectrum, phase, and chirp employed with the system.
Figure 7B:
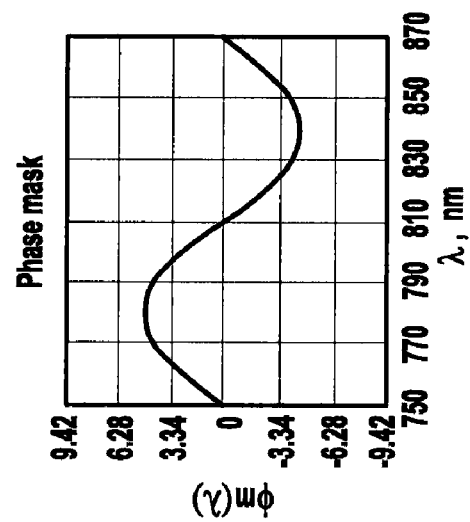
Figure 7A:
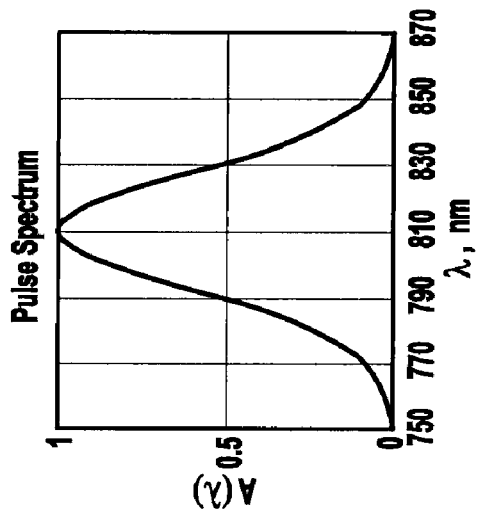

The preceding formulas [6]-[29] give the general result. The following parameters must be defined, however, for a user to define a phase mask that would minimize or maximize a particular multiphoton process. First, the laser pulse spectrum of FIG. 7A must be defined. The shorter the pulses (broader spectrum), the better the control. 45 fs pulses have been satisfactorily used but 20 or 10 fs would lead to even better results. The carrier frequency (or center wavelength) must also be defined by availability. Tuning the wavelength of the pulse could enhance certain processes but is not typically required. Secondly, the phase modulator (or alternately, the SLM, deformable mirror, chirped mirror, etc.) should cover the entire pulse spectrum and must be defined. Thirdly, a phase mask definition should be introduced. The simple sine function of FIG. 7B works remarkably well, yet other functions that can become symmetric and antisymmetric as a function of their position are also suitable. Fourthly, the addition of positive or negative linear chirp φ further enhances the observed control, as expressed in FIG. 7C, and should be defined. The phase mask used in the examples presented herein is defined by $$\phi_m(\lambda, \delta) = \phi_a \sin\left(\frac{\lambda - \lambda_{min}}{\lambda_{max} - \lambda_{min}} \cdot 2\pi N - \delta\right) \quad [30]$$

where δ is the position of the sine function (centering) across the spectrum, $\phi_a$ is the maximum phase delay, and $N_{pixel}$ is the number of pixels in the SLM, as illustrated in FIG. 7B.

When chirp is added, it can be defined by $$\phi_c(\Omega) = \tfrac{1}{2} \phi'' \Omega^2 \quad [31]$$

where β is the amount of linear chirp expressed in FIG. 7C. Thus, the complete phase mask with chirp is:

$$\phi(\lambda) = \phi_m(\lambda, \delta) + \phi_c(\lambda). \quad [32]$$

Figure 8B:
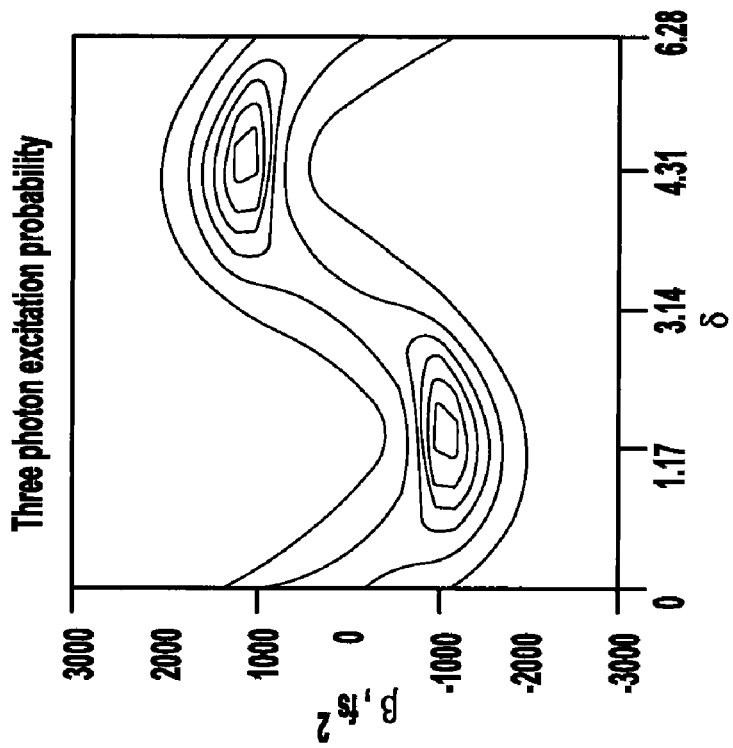
FIGS. 8A and 8B are graphs showing the calculated two and three photon absorption probability obtained with the system.
Figure 8A:
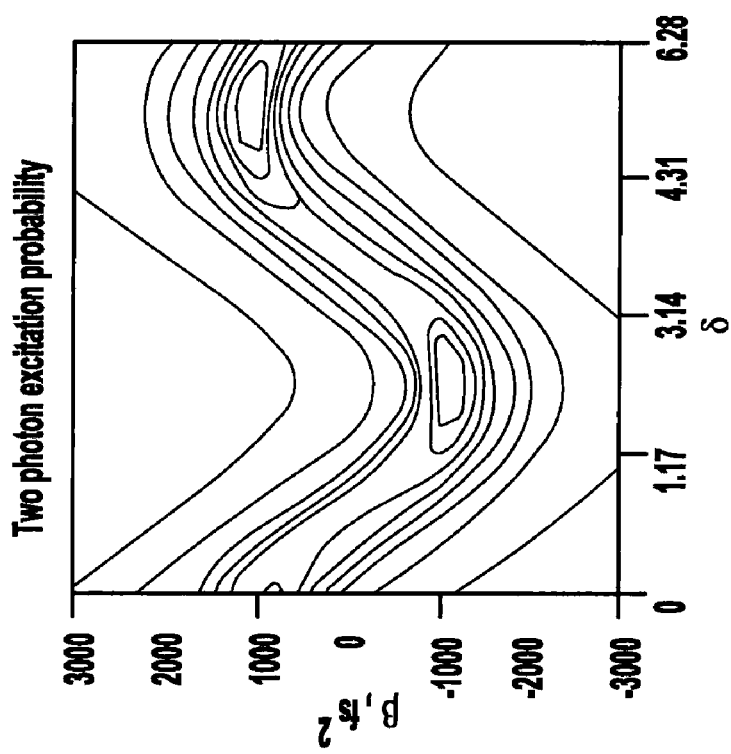
Figure 9B:
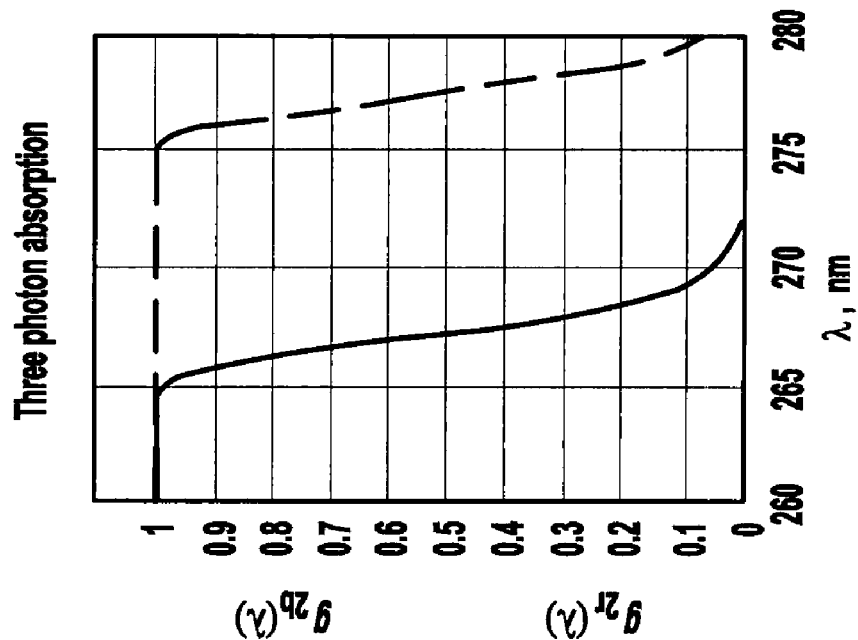
FIGS. 9A-9C are graphs showing the calculated two and three photon absorption probability employed with the system.
Figure 9A:
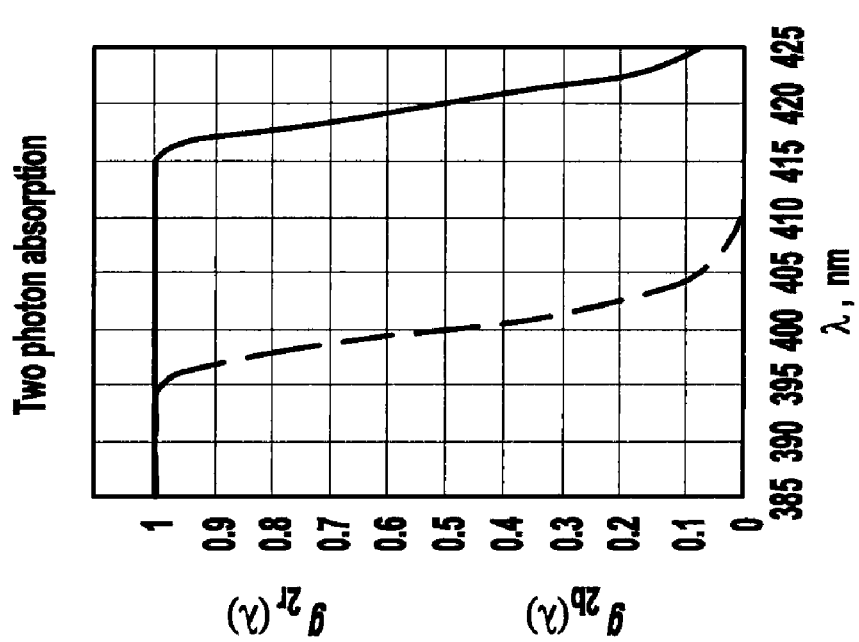
Figure 9C:
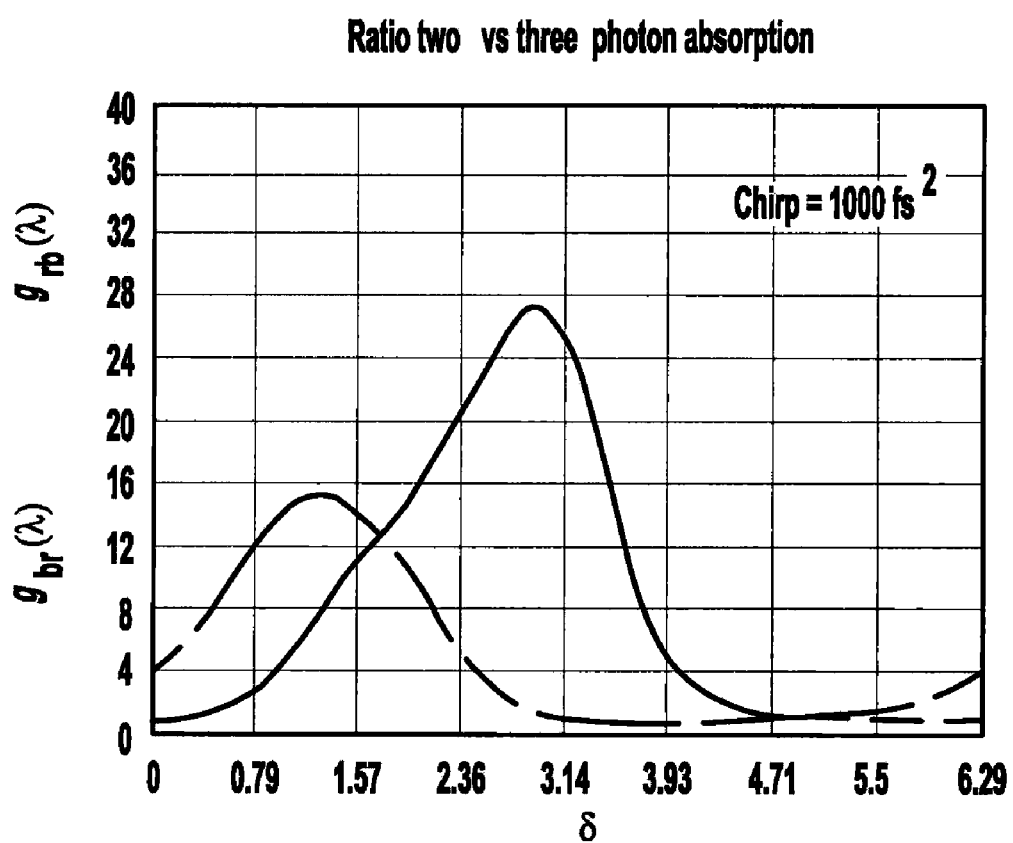

FIGS. 8A and 8B show the calculated two and three photon absorption probability using the equation presented and the absorption spectra as calculated by the dotted lines in FIGS. 9A-9C. FIG. 9C shows the calculated ration two:three photon absorption for the two different combinations of absorption spectra given in FIGS. 9A and 9B. Accordingly, robust control of multiphoton processes in molecules, proteins and nonlinear optical materials can be achieved through either adaptive, active and self optimizing learning programs and control systems, or through calculated, predetermined or fixed, passive laser beam pulse shaping devices. Therefore, inexpensive fixed phase masks can be designed before the experiment, and even without computer controlled shapers and learning programs, to control the order of multiphoton processes for large, complex molecules, proteins in photodynamic therapy, optical tomography, surgery (such as laser cutting by five or greater photon wave conveyance to maximize nonlinear energy), and photochemistry control of, for example: (a) photopolymerization (by photon pair switching to seed the process), (b) charge transfer, (c) radical reaction, (d) nucleophelic attack and (e) electrophylic attack.

Communications

Figure 10:
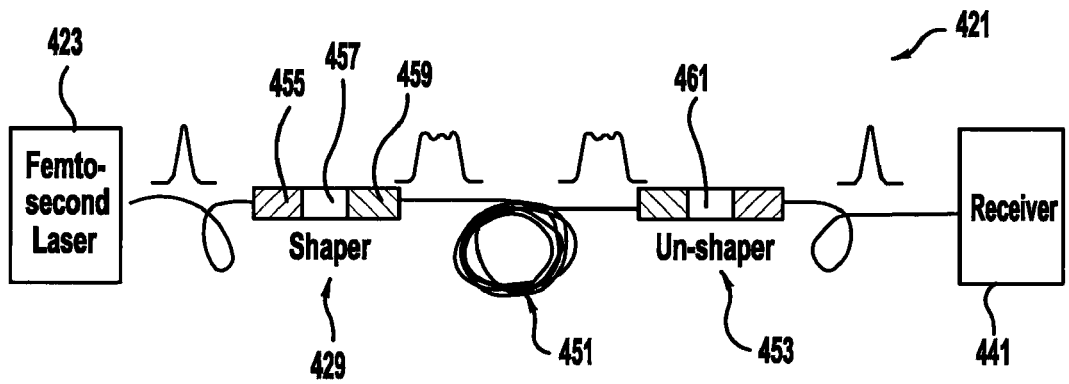
FIG. 10 is a diagrammatic view showing an alternate embodiment of the present invention system applied to fiber optic communications.

With reference to FIG. 10, an alternate embodiment of a laser excitation system 421 of the present invention employs a femtosecond laser 423, an optical fiber 451, a laser beam pulse shaper device 429, a laser beam pulse un-shaper device 453, and a receiver 441 which includes an optical switch or sensor and the related circuitry and electrical control unit. Laser 423 emits a series of laser beam pulses, each shorter than 1 ps, into the connected fiber 451. Pulse shaper device 429 is of a predetermined mask type with a fixed pulse characteristic varying shape (such as with calculated sine wave surface shapes) and has three elements connected to fiber 451: a dispersive element 455 such as a fiber that incorporates a diffraction grating; a phase mask element 457 that can be made using a doped glass or polymer sheet; and a dispersive element 459, like element 455 but reversed, for accepting spectrally dispersed light and coupling it back to fiber 451.

The shaped laser beam pulse is capable of traveling long distances through fiber 451 without suffering nonlinear distortion because of the unique phase function imprinted or formed on shaper device 429. For example, the red color spectrum may be advanced in front of the blue color spectrum in a precise sine manner. Un-shaper device 453 subsequently reverses the phase changes introduced by shaper device 429. It is constructed the same as the shaper device but with a different phase mask element 461 that compensates for the pulse characteristic changes made by mask element 457. Alternately, an acousto-optic modulator or transient grating can be used for optical switching through constructive or destructive reference of waves. Shaping and unshaping can also be accomplished by means of a chirped mirror or spectral masks.

Thus, the present invention's ability to precisely control the laser beam pulse shape or other characteristic, especially for nonlinear or multiphoton emissions, significantly improves the quality of the communication transmission while minimizing self-focusing, self phase modulation and possible destruction of the fiber. The pulse characteristic control of ultrafast laser beam pulses, as described in all of the embodiments herein, should minimize, if not prevent, multiplicative noise effect disruption of nonlinear propagation channels in fiber optic lines, as discussed in Mitra, et al., "Nonlinear Limits to the Information Capacity of Optical Fibre Communications," *Nature*, vol. 411, pp. 1027-1030 (Jun. 28, 2001). It is further envisioned that this type of pulse shaping system can be employed within salt water oceans for submarine-to-submarine communications using short laser pulses of 1 ps or less. This type of pulse shaping can be used to induce solution formation to achieve minimally distorting pulses for communications. Moreover, MIIPS can be used to measure the distance of a fs laser emitter by determining the magnitude of the acquired second order phase modulation as the laser pulse transmits through air or water. This method does not require echo or reflection. In water longer pulses (1 ps) are desired because of the much greater dispersion. Depending on the transmission medium, air or water, and the distances expected different pulses are required. For air, short pulses with durations between 10-20 fs will be preferred. For water, pulses with much longer durations will be preferred, for example for 100 m distance 100 ps pulses would be preferred.

Figure 11:
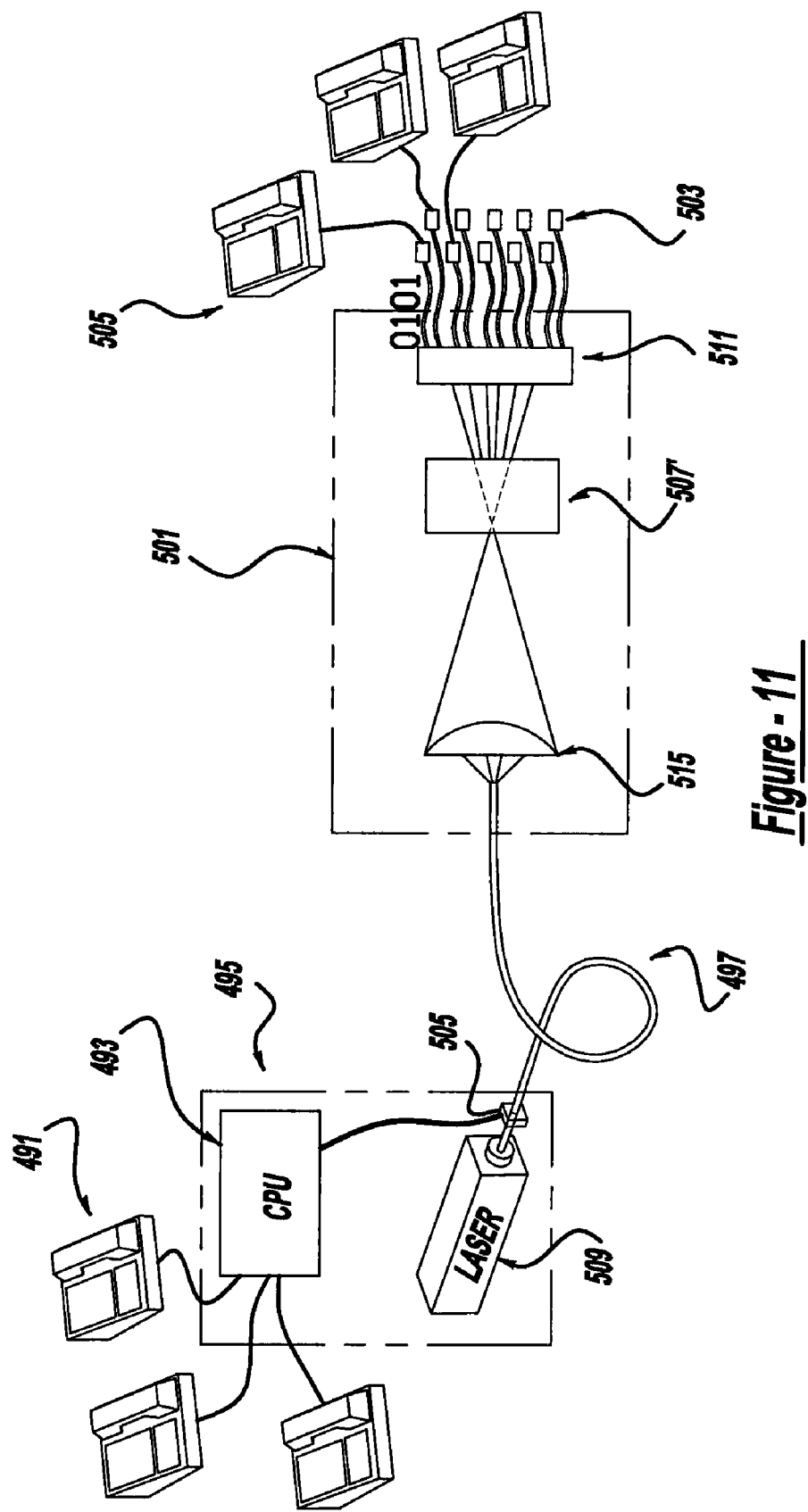
FIG. 11 is a diagrammatic view showing a fourth preferred embodiment of the present invention system applied to fiber optic communications.
Figure 12A:
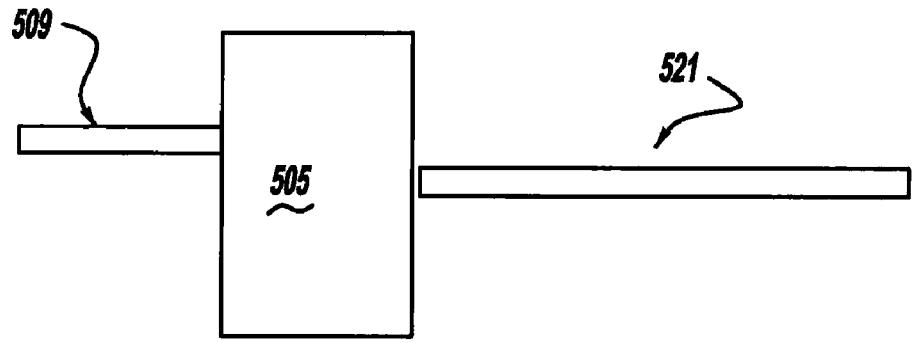
FIGS. 12A and 12B are diagrammatic views showing components employed in the fourth preferred embodiment system.
Figure 12B:
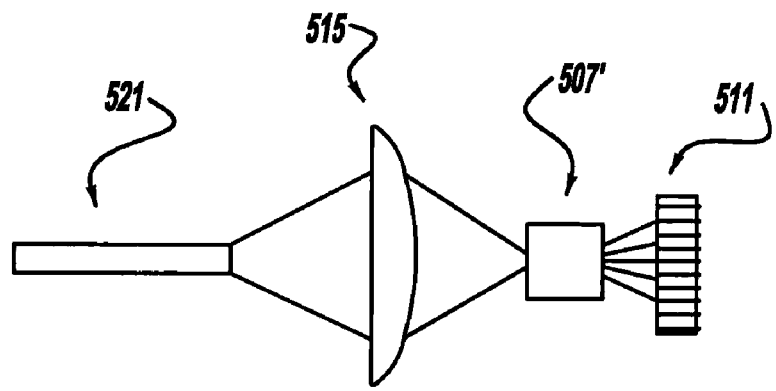

Referring to FIGS. 11, 12A and 12B, a fourth preferred embodiment of the system of the present invention is used for fiber optic communications. Multiple transmission users who are each sending a communications message or signal are using a communications device such as a telephone 491, personal computer, facsimile machine or the like, at remote locations from each other. These remote transmitters are connected to a "smart" main transmitter assembly which includes a computerized, central processing unit 493 through electric wires, fiber optic cables, microwave signals or the like. A phase modulated pulse shaper 505 is actively controlled by CPU 493. Laser 509 and shaper 505 are also contained as part of the main transmitter assembly. Laser 509 emits an ultrashort laser pulse which is carried within a fiber optic cable 497 after shaping. The ultrashort laser beam pulses have a duration of about 100 femtoseconds based on currently available fiber optic cable limitations but pulse durations of less than 50 femtoseconds would be preferred and those of 10 or less femtoseconds would be the most desired if fiber optics allow for such in the future. For example, photonic band gap materials such as optical fibers with holes therein may allow for use of approximately 10 femtosecond pulses.

Pulse shaper/phase mask 505 causes each laser beam pulse phase to tune the second and third order harmonics of each peak and to cause multiple peaks, by way of example, but not limitation, in each pulse frequency. This allows encoding of routing addresses and the associated communications information to be encoded within each laser beam pulse based on CPU control of the laser beam emissions in combination with actively varied shaping of each emitted pulse.

A "dumb" central receiver 501, one that does not require an additional laser or complex computational capabilities, is connected to the downstream end of fiber optic cable 497. Receiver 501 includes a focusing lens 515, a thick SHG crystal 507' and a detector 511. Each laser beam pulse transmitted through fiber optic cable 497 is dispersed onto lens 515 which serves to focus and direct each pulse, in a converging angular manner, onto crystal 507'. A thick optical crystal 507' is defined herein as one having a transmissive path thickness of greater than about 0.5 millimeters while a thin optical crystal 507 (see FIG. 15) is defined herein as having a transmissive path thickness less than about 0.5 millimeters. The preferred thickness for the thick crystal is approximately 3.0 millimeters for 50 femtosecond or less pulse duration and 5.0 millimeters for a 50 to 200 femtosecond pulse duration. Thick crystal 507' creates a second order harmonic and second order spectrum within each pulse as previously shaped by the pulse shaper. In other words, the thick crystal disperses essentially the entire color spectrum without use of a separate spectrometer because of the phase matching angle requirement.

Each separated color frequency angularly dispersed from the thick crystal is encoded by the pulse shaper to contain individual communication routing addresses and the actual communications information, which is then detected by a multiplexer-type of detector 511 such as a CCD camera employing a linear array. Alternately, detector 511 is a two-dimensional array that can be used to achieve higher data densities by adding one more dimension. It is also alternately envisioned that detector 511 is an array of optical fibers that are connected to remote controllers/sub-detectors. The data can be read asynchronously using only the transmission pulse containing the information and not additional reference pulse. A single detector 511 is operable to digitize the detected signals carried in each pulse as separated through the spectrum and transmit them through wires, fiberoptics, microwaves or the like to individual decoding microprocessor controllers 503 within or external to receiver 501. A set of prestored variables or decryption information or key is located within memory of each controller 503 in order to decode each corresponding digitized communication signal received by detector 511 without requiring synchronous communication transmissions (in other words, a second laser pulse that provides a complimentary phase) from transmitter 495. The decoded communications are then sent to the end users who receive such by telephones 505, personal computers, facsimile machines or the like at the identified routing addresses desired. Alternately, controllers 503 can be replaced by simple light detection devices such as photodiodes which can be employed in a digitized on/off self-switching mode based on the signal detected by detector 511 to control or send information to remote destinations. It is significant that interferometry and synchronous laser pulses are not required for decoding the transmitted information with the presently preferred communications embodiment of the present invention. It is also noteworthy that pulse shaper 505 can encode each pulse by use of second harmonic generation or any other non-linear mixing method including, but not being limited to, frequency mixing, difference frequency mixing, and four wave mixing.

The present invention should be contrasted to a prior experiment which employed a difficult and a synchronous reference pulse at the decoder for supplying a complimentary phase to control the emission of a single specific wavelength. This is disclosed in Z. Zheng and A. Weiner, "Coherent Control of Second Harmonic Generation Using Spectrally Phase Coded Femtosecond Waveforms," *Chemical Physics* 267, p. 161 (2001); this prior approach, however, required pulses which overlap in time and space, which is difficult to control, and only for a single pulse frequency.

Multiphoton Intrapulse Interference Phase Scan

A multiphoton intrapulse interference phase scan (hereinafter "MIIPS") system and method of the present invention characterize the spectral phase of femtosecond laser pulses. This single beam method is capable of retrieving the magnitude and sign of second and third order phase modulation (in other words, linear and quadratic chirp) directly, without iteration or inversion procedures. MIIPS achieves accurate phase retrieval from chirped ultrashort pulses. For MIIPS, no synchronous autocorrelation, beam splitting, or time delays are required because the second harmonic spectrum depends on the relative phases of all frequencies within the pulse. The amplitude of the pulse is obtained directly from a spectrometer in a communications receiver. In order to precisely determine of the phase of all frequency components in a pulse from a fs laser 123 (see FIG. 15), a pulse shaper, such as the one described in A. M. Weiner, "Femtosecond pulse shaping using spatial light modulators," Rev. Sci. Instrum. 71, pp. 1929-1960 (2000), is employed to introduce a reference phase function designed to yield this information directly, as further described hereinafter. The shaped pulses are frequency doubled by a thin SHG crystal 507 (see FIG. 15) and the output is directed to spectrometer 503.

The system and method of the present invention are aimed primarily at decoding the phase as a function of frequency of an ultrafast laser pulse. The measurement requires determination of the intensity of the second order electric field of the laser pulse. This property can be measured by measuring the spectrum of the laser after it has been frequency doubled. A comparison of the spectrum of the pulse and the spectrum of its second harmonic is enough to decode phase distortions. This simple approach works well in all asymmetric phase functions. For symmetric phase functions there are potential ambiguities. For example, quadratic chirp only leads to attenuation of the second harmonic spectrum; from this attenuation alone, it would be impossible to determine the sign of the chirp. A setup that compares the SHG spectrum from a pulse that has been additionally shaped by a known phase function would solve those ambiguities. The resulting data then contains enough information to determine the spectral phase of the ultrafast pulse, including sign.

As a communications device, the above system can use the phase introduced in ultra-short pulses, taking advantage of multiphoton intrapulse interference to tune the nonlinear optical conversion, for example second harmonic generation spectrum, to decode phase encoded data transmissions. The encoder can be used to encode information that upon nonlinear optical conversion, for example second harmonic generation, yields a specific set of peak heights at specific wavelengths. This encoder can use sine or cosine functions to create a peak in the second order spectrum. Conversely, the encoder can create a number of peaks on the second order spectrum thereby achieving a greater number of communication bits. Fast encoding and almost instantaneous decoding of shaped pulse phases using phase functions as discussed herein can be achieved with the present invention.

When thin doubling crystals are used, a dispersive spectrometer 503 (see FIG. 15), such as a grating, prism or similar device, is required to detect the resulting wavelength tuning caused by the phase modulation. Different wavelengths will travel to different locations, however, if the signal beam is focused tightly on a thick second harmonic generation crystal 507' (see FIG. 12B). Tight focusing, for example f/1, ensures that the incident light samples a number of phase matching angles instead of only one. As the phase-matched beam enters the crystal 507' one direction will be preferred based on the phase that was imprinted on the message. The phase imprinted on the pulse can therefore be used for the message to "route itself." These applications are related but different than others in which a long SHG crystal is used with minimal or no focusing, therefore having a narrow frequency conversion range limited by the phase matching angle. In those cases only two outputs are possible emission or no emission. In the present invention emission at multiple wavelengths is possible thereby providing great multiplicity.

Figure 14:
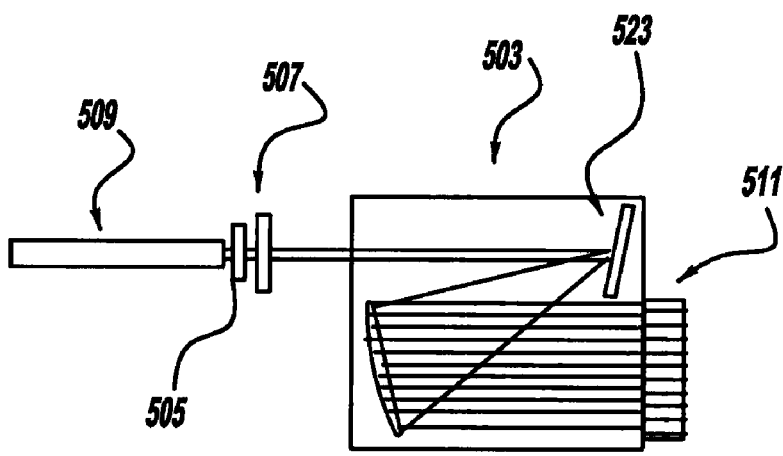
FIG. 14 is a diagrammatic view showing the fifth preferred embodiment system.

It is noteworthy that when the present invention is used for pulse characterization a reference or known phase function is superimposed to the unknown phase using a pulse shaper 129 (see FIG. 15) or alternately, 505 (see FIG. 14). A two-dimensional preset, fixed pulse shaping mask (such as that shown in FIG. 20) can be employed to allow a one shot method for phase determination and characterization or even for encoding and decoding in communications. With this one shot approach, the phase mask pulse shaper generates pulses that contain a complex two-dimensional phase. Such pulse after nonlinear optical conversion yields hundreds of spectra from one pulse rather than the many pulses otherwise required with more conventional pulse shapers. A two-dimensional CCD camera is used to collect and detect the nonlinear optical signal and retrieve all the information. This single shot system and method factor out instabilities between multiple pulses and are considerably faster than conventional approaches. Furthermore, the two dimensional CCD detector 511 does not require a movable or deformable pulse shaping mask and does not require the conventional need for considerable calculations within computer 531 in order to convert the single dimensional measurements to the more desirable two-dimensional measurements as shown in the phase scanned graphs. In addition to laboratory testing and specimen optic distortion analysis, the MIIPS system and method employing this single shot construction can also be applied to some communication situations in order to add considerably more encoded information into each pulse phase to supply additional encoding variables.

The MIIPS method is based on the principle that second harmonic generation, as well as other nonlinear optical processes, depend on the phase function $\phi(\Omega)$ across the spectrum of the laser pulse. The phase function can be expanded in a Taylor series around carrier frequency $\Omega=\omega-\omega_0$ as follows:

$$\phi(\omega)=\phi(\omega_0)+\phi'(\omega_0)\Omega+\tfrac{1}{2}\phi''(\omega_0)\omega^2+\tfrac{1}{6}\phi'''(\omega_0)\Omega^3+\ldots, \quad [33]$$

where the first two terms provide only the relative (common) phase and a time delay, respectively. Only the third and higher terms are responsible for phase distortion. These higher terms are retrieved in MIIPS by superimposing a reference phase function on the pulse to obtain, $$\phi(\Omega)=\alpha\cos(\gamma\Omega-\delta)+\phi(\Omega) \quad [34]$$

where the first term is the reference phase function introduced by the shaper with maximum phase amplitude $\alpha$, period $\gamma$ and the absolute position in the spectral window $\delta$. $\phi(\Omega)$ is given by Equation 33.

The maximum SHG signal as a function of $\Omega$ is obtained when $d^2\phi(\Omega)/d\Omega^2=0$. A parameter in the reference phase function can be varied to obtain a plot from which the phase distortions ($\phi''$, $\phi'''$, ...) can be obtained in the laser pulse. The maximum signal in a (wavelength, $\delta$) MIIPS trace describes a series of lines given by $$\delta_{max}=\delta_0+(\lambda_{max}-\pi c/\omega_0)\omega_0^2/(\pi c)\{\gamma-\phi'''/(\alpha\gamma^2\sin\delta_0)\}, \quad [35]$$

where $\delta_{max}$ is the position where maximum SHG signal is obtained, $\delta_0=\arccos[\phi''/(\alpha\gamma^2)]$, and $\lambda_{max}$ is the position of the maximum SHG signal.

A complete data set, from which a phase function can be retrieved, consists of a series of spectra obtained as a function of the parameter $\delta$. The resulting experimental MIIPS trace shown in FIG. 16, contains the required information to extract $\phi''$, $\phi'''$ and higher order terms as follows. First the data is fit to a series of lines which follow $\lambda_{max}(\delta_{max})$ as expected from Equation 35. The quadratic phase modulation (responsible for linear chirp) is determined directly from the distances $x_1$ and $x_2$ between the SHG maxima (see FIG. 16), according to $$\phi''=\alpha\gamma^2\arcsin[(x_1-x_2)/4]. \quad [36]$$

Note that the magnitude and sign of $\phi''$ are obtained directly from the MIIPS trace. Furthermore, the accuracy of the measurement can be improved for small phase distortion by decreasing the reference phase function parameters $\alpha\gamma^2$.

Figure 16:
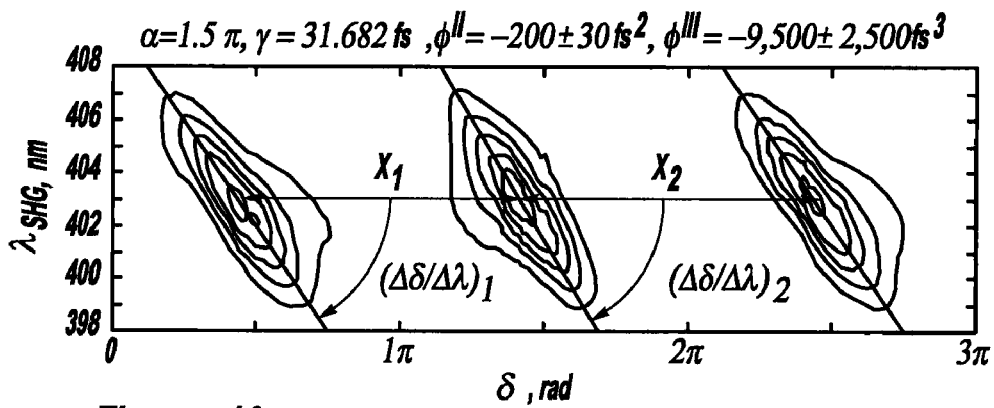
FIG. 16 is a graph showing phase scans created by use of the fifth and sixth preferred embodiment system.

The cubic phase modulation (quadratic chirp) is determined by the slope $\Delta\delta/\Delta\lambda$ that the maximum SHG features make in the $\lambda\,\delta$ plane. Analytically, cubic phase modulation is given by $$\phi'''=0.5\alpha\gamma^2\pi c/\omega_0^2\cos[(x_1-x_2)/4]\{(\Delta\delta/\Delta\lambda)_1-(\Delta\delta/\Delta\lambda)_2\}, \quad [37]$$

where the slopes are measured in $nm^{-1}$ (see FIG. 16). Higher order phase distortions, such as self-phase modulation and quadratic phase components can be obtained from the curvature of the line defined by the maximum SHG response. These higher order terms are not always essential and are left for a more elaborate presentation of the theory behind MIIPS. The fit to the experimental data shown in FIG. 16-17C is given by Equation 35, and the phase parameters are extracted with Equations 36 and 37.

The version of MIIPS illustrated in FIG. 15 uses a thin SHG crystal 507, spectrometer 503, pulse shaper 129 and a femtosecond laser 123. A fs laser pulse is preferred but, for test data disclosed herein, 50 fs pulses from a regeneratively amplified Ti:Sapphire laser were employed wherein the pulse energy was attenuated down to ~5 μJ. For the test data herein, A 0.3 mm βBBO type I crystal was used for SHG 507 and the output was attenuated and directed to spectrometer 503 with a cooled CCD detector 511. System 121 further has a redirecting mirror 513, two quartz cylindrical lenses 515 (200 mm focal length, the upstream one for focusing and the downstream one for collimating). For the tests, a spatial light modulator was used for pulse shaper 129 consisting of two 128 LCD elements (which can be obtained from CRI Inc. as model number SLM-256). For the test, the pulse shaper was carefully calibrated to provide accurate phase delays (better than one degree) with no changes to polarization or amplitude. The phase distortions used to obtain the data were generated at the pulse compressor after regenerative amplification.

Figure 17A:
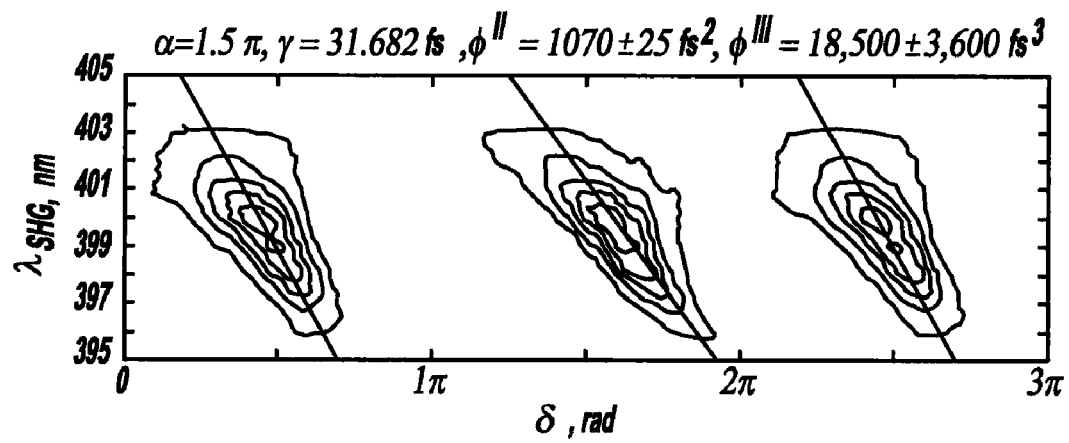
FIGS. 17A-17C are graphs showing phase scans created by use of the sixth preferred embodiment system.
Figure 17B:
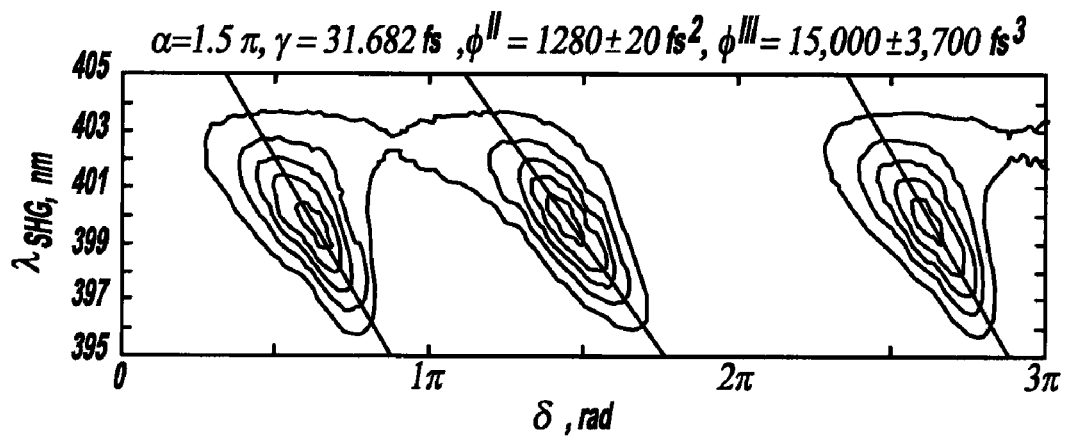

The experimental results in FIG. 16 correspond to laser pulses that are close to transform limited. Analysis of the data indicates a residual phase distortion with quadratic and cubic components. The SHG intensity as a function of phase mask position d is given by the contours. The diagonal lines are fits to the experimental data using Equation 35 and 36, using the spacing between the features and the angles that these make. FIGS. 17A and 17B present data obtained for positive and negative linear chirp. Changes in the spacing of the SHG signals are shown. In both cases there is some quadratic chirp. In contrast, FIG. 17C shows data obtained for heavy quadratic chirp. In this case, the angles of the SHG features are visibly different. This data has a relatively small amount of linear chirp. In other word, in FIGS. 17A-17C experimental data is for pulses with greater phase distortion. The MIIPS data of FIGS. 17A and 17B show positive and negative quadratic phase distortion in addition to a substantial cubic component. The difference in the distance between the features can be used to obtain the sign and magnitude of $\phi''$ using Equation 36. The ability to determine quadratic phase modulation by inspection is very valuable given that it results from normal dispersion, when ultrashort pulses propagate through any optical medium.

Figure 17C:
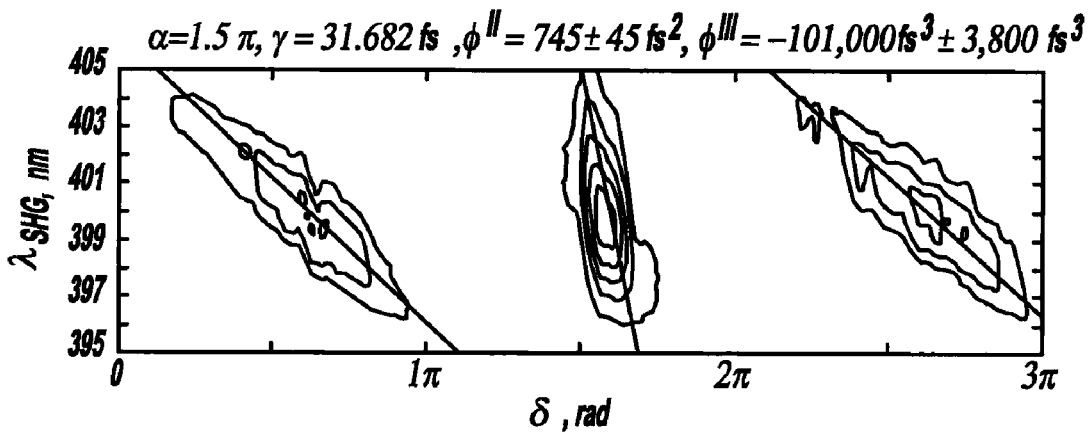

The MIIPS trace obtained for pulses with significant cubic phase modulation is illustrated in FIG. 17C. The difference in the angle between the features indicates the presence of cubic phase modulation, which is determined quantitatively using Equation 37. A number of additional measurements have been made using the MIIPS method with the following advantages. The setup is as simple as adding an SHG crystal and sending the output to a spectrometer. For low intensity lasers (<0.1 nJ) one can simply focus the laser on the SHG crystal to increase the conversion efficiency.

Because the resolution and range of the MIIPS method are directly proportional to the reference function parameters, it is simple to adjust them as needed. The range is given by $|\phi''|<\alpha\gamma^2$ and $|\phi'''|<\alpha\gamma^3$. The resolution is determined by the shaper resolution and, here, was found to be less than one percent of the full range for both $\phi''$ and $\phi'''$. For example, $\phi''$ values can be determined in the range of 10 to $10^5$ $fs^2$ for 10-100 fs pulses. The simplicity and accuracy of this method make it practical for the evaluation laser pulses close to transform limit and for the evaluation of phase distortion from optical elements.

Figure 13:
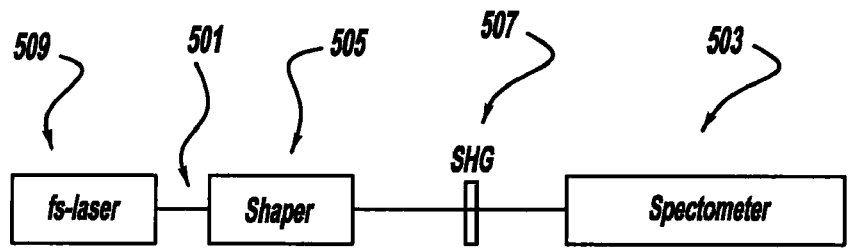
FIG. 13 is a diagrammatic view showing a fifth preferred embodiment of the system of the present invention for use with pulse characterization or communications.

Referring now to FIGS. 13 and 14, self-ultrafast switching is based on pulse phase modulation in pulse shaper 505, a thin SHG crystal 507 causing multiphoton intrapulse interference, dispersive optics 523, and CCD camera detector 511.

Figure 18:
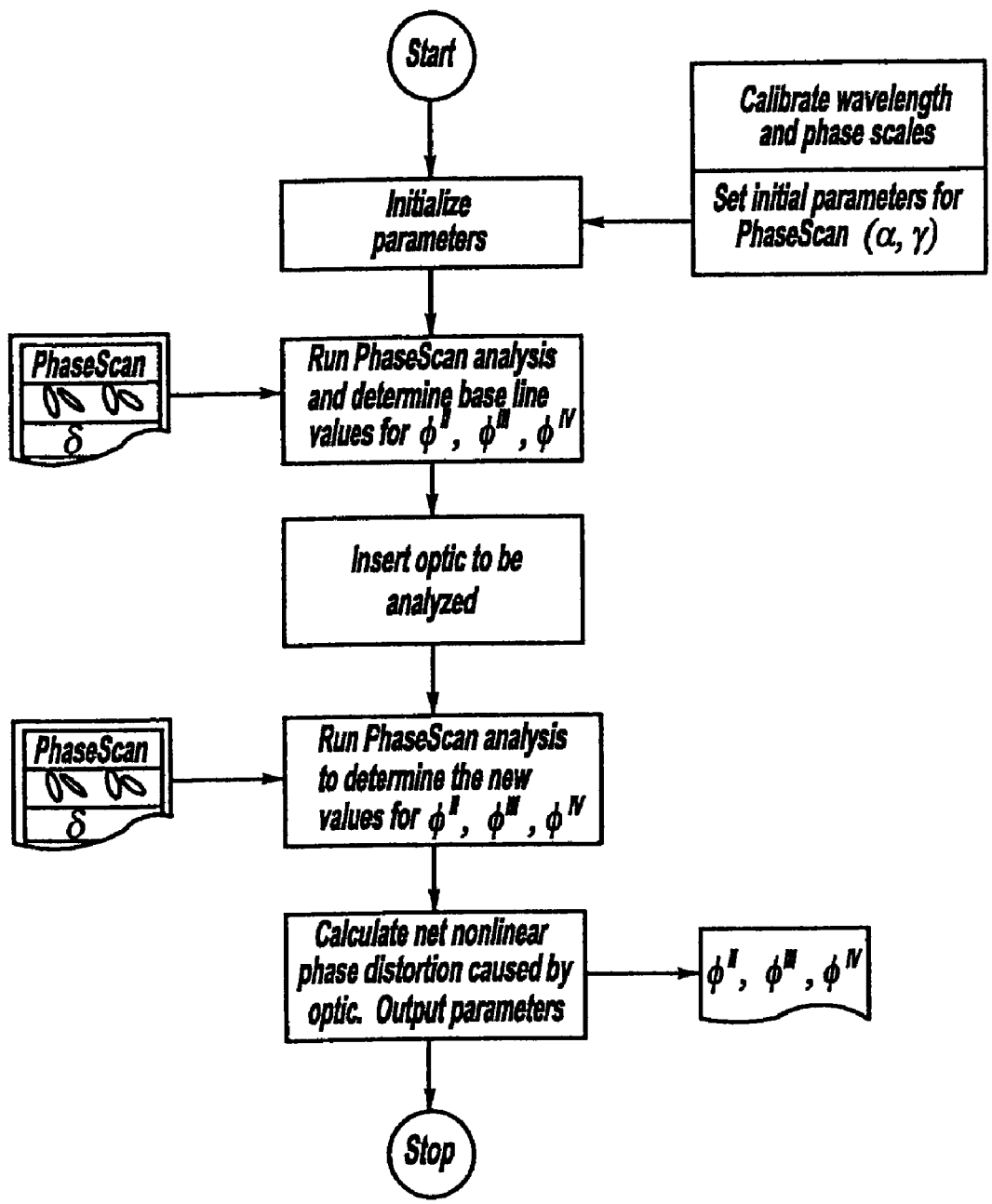
FIGS. 18 and 19 are flowcharts of computer software employed in the sixth preferred embodiment system.
Figure 19:
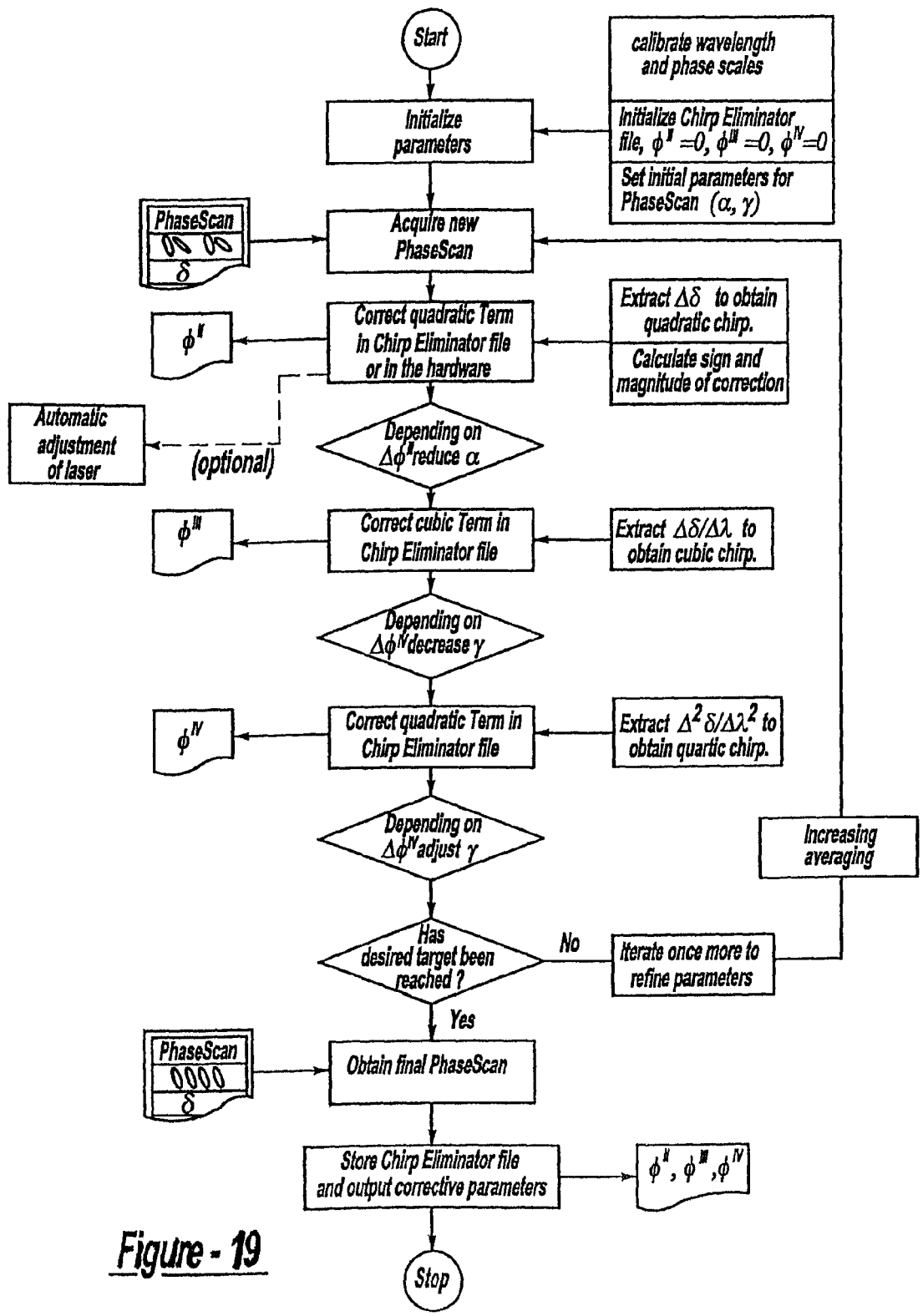

FIG. 18 illustrates the software logic flow used in the microprocessor control unit of the personal computer 531, shown in FIG. 15. This software is stored on a medium, such as a memory chip of the computer, and determines nonlinear phase distortion for an analysis of optics. This method is based on the use of pulse determination by the phase scan and the measurements can be done for different laser pulse intensities. The software logic flowchart for the automated pulse chirp determination is shown in FIG. 19. This software is also stored in the computer's memory and can adjust parameters in the pulse compressor to obtain distortion and to optionally adjust the laser components for chirp. This method is based on the use of a pulse shaper and obtaining a phase scan, which is the spectrum of the SHG as a function of phase parameter $\delta$ using the reference phase function:

$$\phi(\omega)=\alpha\cos(\gamma\omega+\delta) \quad [38]$$

This method is non-iterative and directly obtains the desired values without learning algorithms. Therefore, this method is very stable and does not depend on overlap between two pulses in space and time. The pulse in the single laser beam analyzes itself in a thin SHG crystal.

In summary, the present invention provides a system and method to characterize the spectral phase of femtosecond pulses. This single beam method is capable of retrieving the magnitude and sign of linear and quadratic chirp with high resolution. Pulse retrieval is based on analytical expressions that yield the phase distortion, without iteration or inversion procedures. Linear and quadratic chirp values, and to some extent cubic chirp values, are important because there are knobs on the laser that can be used to correct for this distortion by mechanically adjusting the grating spacing in the laser beam amplifier compressor. The method can be used with very short pulses. This adjustment can be automatically controlled with the computer controlled software as disclosed in FIG. 19. The method is very versatile, and can be used with high or very low intensity pulses for any wavelength for which low cost, off-the-shelf SHG crystals exist. MIIPS can also be used by obtaining third or higher order harmonics in gases. The maximum signal will also agree with Equation 35, making the method useful for the characterization of pulses in wavelength regions for which SHG crystals are not available. In summary, uses of MII and MIIPS are as follows:

- MII can be used to make self-switching pulses as long as they undergo one non-linear optical process, such as SHG, sum frequency generation, difference frequency generation or four-wave mixing;
- MIIPS can be used to allow automated laser optimization, specifically quadratic and cubic phase distortions;
- MIIPS can be used for pulse characterization;
- MIIPS can be used to measure the phase modulation induced by optical elements and similarly it can be used to measure the thickness of a substrate;
- MIIPS can be used for decoding information (address and/or message) stored in the phase;
- Shapers operating to optimize the MII phenomenon can encode self-decoding messages;
- MII can be used to prevent three photon damage of DNA from fs pulses; and
- MII can be used to optimize the activation of PDT agents specifically at a particular depth.

The following references disclose two-photon photopolymer initiators:
(1) "New Photopolymers based on Two-Photon Absorbing Chromophores and Application to Three-Dimensional Microfabrication and Optical Storage," B. H. Cumpston, J. E. Ehrlich, L. L. Erskine, A. A. Heikal, Z.-Y. Hu, I.-Y. S. Lee, M. D. Levin, S. R. Marder, D. J. McCord, J. W. Perry, H. Röckel, and X.-L. Wu, Mat. Res. Soc. Symp. Proc., Vol. 488, "Electrical, Optical, and Magnetic Properties of Organic Solid-State Materials IV," (MRS, Warrendale, 1998) p. 217; and
(2) "Two-Photon Polymerisation Initiators for Three-Dimensional Optical Data Storage and Microfabrication," B. H. Cumpston, S. Ananthavel, S. Barlow, D. L. Dyer, J, E. Ehrlich, L. L. Erskine, A. A. Heikal, S. M. Kuebler, I.-Y. Sandy Lee, D. McCord-Maughon, J. Qin, H. Röckel, M. Rumi, X.-L. Wu, S. R. Marder and J. W. Perry, Nature, in press. It is envisioned that multiphoton intrapulse interference can be advantageously used to enhance this non-linear photopolymerization.

While the preferred embodiment of the control system and system of the present invention have been disclosed, it should be appreciated that various modifications can be made without departing from the spirit of the present invention. For example, other laser beam pulse characteristics can be varied and employed with the present invention beyond the pulse shaping, wavelength and duration characteristics preferably described. Furthermore, additional software subroutines and statistical analyses can be employed. Moreover, other optical and pulse shaping components can be used in place of those described. Finally, analog, solid state and fiber optic electrical control circuits can be substituted for or used in addition to a microprocessor and other computer circuitry. Various optics, including lenses and mirrors, can be used to achieve reflecting, collimation or focusing. Additionally, dispersive optics, such as gratings and prisms, can be interchanged. Detection of the laser induced processes may use various spectroscopic methods including laser induced fluorescence, Raman spectroscopy, nuclear magnetic resonance, gas chromatography, mass spectrometry and absorption spectroscopy. While various materials, specimens and components have been disclosed, it should be appreciated that various other materials, specimens and components can be employed. It is intended by the following claims to cover these and any other departures from the disclosed embodiments which fall within the true spirit of this invention.

The invention claimed is:

1. A laser beam pulse shaping system comprising:
a laser beam pulse; and
a permanently fixed pulse shaper including multiple repeating and predetermined shaping patterns;
the fixed pulse shaper operably changing a phase characteristic of the pulse without computer control of the shaper;
wherein the patterns are offset as a function of a wave phase; and
wherein the fixed pulse shaper introduces multiphoton intrapulse interference in the pulse without computer control of the pulse shaper.

2. The pulse shaping system of claim 1, further comprising a communications device operably receiving the pulse shaped by the fixed pulse shaper.

3. The pulse shaping system of claim 2, wherein the shaper encodes a communications signal onto the pulse for use by the communications device.

4. The pulse shaping system of claim 1, further comprising a two-dimensional CCD camera operably collecting and detecting the spectrum of a nonlinear optical signal, and retrieving information from the shaped pulse.

5. The pulse shaping system of claim 1, wherein the substrate is polymeric.

6. The pulse shaping system of claim 1, wherein the substrate and wave patterns are of an injection molded material.

7. The pulse shaping system of claim 1, wherein the wave pattern is a sine wave which repeats across the substrate with adjacent rows of the pattern being offset from each other.

8. The pulse shaping system of claim 1, wherein the patterns operably generate multiple phases from a single laser beam pulse.

9. The pulse shaping system of claim 1, wherein the pattern is configured for a laser beam pulse of less than about 11 femtosecond duration.

10. The pulse shaping system of claim 1, further comprising using the fixed pulse shaper to determine and characterize the phase of the pulse.

11. A laser beam pulse shaping system comprising a mirror including a preset shaping pattern thereon, and a phase of a laser pulse being tailored with the mirror, wherein the preset mirror introduces multiphoton intrapulse interference in the pulse without computer control of the mirror.

12. The pulse shaping system of claim 11, further comprising multiple dichroic layers on the mirror.

13. The pulse shaping system of claim 11, wherein the mirror is chirped.

14. The pulse shaping system of claim 11, wherein the mirror has a fixed two-dimensional wave pattern.

15. The pulse shaping system of claim 11, further comprising using the mirror to assist in determining and characterizing the phase of the pulse.

16. The pulse shaping system of claim 11, wherein multiple preset, shaping patterns on the mirror are offset as a function of the phase.

17. The pulse shaping system of claim 11, wherein the mirror includes a polymeric substrate.

18. A laser beam pulse shaping system comprising a mirror including a preset shaping pattern thereon, and a phase of a laser pulse being tailored with the mirror, wherein the pattern includes a sine wave which repeats across the mirror with adjacent rows of the pattern being offset from each other, and wherein the preset mirror introduces multiphoton intrapulse interference in the pulse without computer control of the mirror.

19. The pulse shaping system of claim 18, wherein the pulse has a duration of less than 11 femtoseconds.

20. A laser beam pulse shaping system comprising a mirror including a fixed two-dimensional wave pattern, and the mirror acting as a pulse shaper to introduce multiphoton intrapulse interference in a laser pulse in a preset manner free of computer control of the mirror pattern.

21. The pulse shaping system of claim 20, further comprising multiple dichroic layers on the mirror.

22. The pulse shaping system of claim 20, wherein the mirror is chirped.

23. The pulse shaping system of claim 20, further comprising using the mirror to assist in determining and characterizing a phase of the pulse.

24. The pulse shaping system of claim 20, wherein multiple shaping patterns are offset as a function of phase of the pulse.

25. The pulse shaping system of claim 20, wherein the mirror includes a polymeric substrate.

26. The pulse shaping system of claim 20, wherein the pattern is a sine wave which repeats across the mirror with adjacent rows of the pattern being offset from each other.

27. The pulse shaping system of claim 20, wherein the pulse has a duration of less than 11 femtoseconds.

28. A laser beam pulse shaper system comprising a laser beam pulse and a device including a predetermined and fixed pulse shaping pattern, the device shaping the pulse to reduce undesired nonlinear optical distortions in the pulse, wherein the device introduces multiphoton intrapulse interference in the pulse without computer control of the device.

29. The pulse shaping system of claim 28, wherein the pattern is based on a quadratic function.

30. The pulse shaping system of claim 28, wherein the pattern is based on a sine wave.

31. The pulse shaping system of claim 28, wherein the device includes a fixed optical substrate containing the pattern.

32. The pulse shaping system of claim 28, wherein the device is a pulse shaping mirror.

33. The pulse shaping system of claim 31, further comprising a reflective coating on the substrate.

34. The pulse shaping system of claim 28, wherein the device assists in characterizing a phase of the pulse, having a duration of less than 51 femtoseconds, in a calculated manner without a learning algorithm.

35. The pulse shaping system of claim 20, wherein the shaper assists in characterizing a phase of the pulse, having a duration of less than 51 femtoseconds, in a calculated manner without a learning algorithm.

* * * * *